(12) United States Patent
Walzman

(10) Patent No.: US 12,138,149 B2
(45) Date of Patent: Nov. 12, 2024

(54) ENDOVASCULAR DEVICES AND METHODS WITH FILTERING ELEMENTS

(71) Applicant: Daniel Ezra Walzman, Bergenfield, NJ (US)

(72) Inventor: Daniel Ezra Walzman, Bergenfield, NJ (US)

(*) Notice: Subject to any disclaimer, the term of this patent is extended or adjusted under 35 U.S.C. 154(b) by 890 days.

(21) Appl. No.: 17/210,778

(22) Filed: Mar. 24, 2021

(65) Prior Publication Data
US 2021/0236257 A1    Aug. 5, 2021

Related U.S. Application Data

(63) Continuation-in-part of application No. 16/501,806, filed on Jun. 10, 2019, now Pat. No. 11,259,820, (Continued)

(51) Int. Cl.
A61F 2/01       (2006.01)
A61B 17/22      (2006.01)
(Continued)

(52) U.S. Cl.
CPC .......... A61F 2/011 (2020.05); A61B 17/22 (2013.01); A61B 17/32002 (2013.01); (Continued)

(58) Field of Classification Search
CPC ........ A61F 2/011; A61F 2/0105; A61F 2/013; A61F 2/2436; A61F 2230/0067; (Continued)

(56) References Cited

U.S. PATENT DOCUMENTS 3,874,388 A    4/1975   King et al.
4,282,875 A    8/1981   Serbinenko et al.
(Continued)

FOREIGN PATENT DOCUMENTS

AU  2011/35359312/2011    12/2011
WO           WO            5/2011
    2011/05700205/2011
WO           WO            9/2019
    2019/17347509/2019

OTHER PUBLICATIONS

Aggarwal S., et al., "Abdominal aortic aneurysm: A comprehensive review", Exp Clin Cardiol, 2011, vol. 16, pp. 11-15.
(Continued)

Primary Examiner — Phong Son H Dang
(74) Attorney, Agent, or Firm — Neil D. Gershon

(57) ABSTRACT

Methods for removing blockages and preventing thromboembolic injuries, by advancing to a blockage a first tubular, endovascular device receiving irrigating fluid through a proximal opening, having a circumferential wall, lumen, at least one distal side hole oriented angularly to a distal opening; ejecting fluid from the side hole(s) to irrigate a blockage; introducing a second catheter for aspiration, comprising a circumferential wall having a proximal and distal opening, a flared, semi-permeable filter at the distal end for removal of emboli through the second lumen; advancing the second device to a blood vessel receiving blood from the blocked vessel, aspirating the blockage, axially rotating the first endovascular device having at least one half-loop to macerate an obstruction, capturing and removing emboli from the blockage through the second endovascular device which prevents emboli from causing further blockage of blood vessels. Variants of said method including a third rotatable device.

16 Claims, 32 Drawing Sheets

Related U.S. Application Data which is a continuation-in-part of application No. 16/125,691, filed on Sep. 8, 2018, now Pat. No. 10,307,242, which is a continuation-in-part of application No. 15/731,478, filed on Jun. 16, 2017, now Pat. No. 10,314,684, which is a continuation-in-part of application No. 15/530,898, filed on Mar. 20, 2017, now Pat. No. 10,299,824, which is a continuation-in-part of application No. 15/258,877, filed on Sep. 7, 2016, now abandoned.

(51) Int. Cl.
*A61B 17/32* (2006.01)
*A61F 2/24* (2006.01)

(52) U.S. Cl.
CPC ............ *A61F 2/0105* (2020.05); *A61F 2/013* (2013.01); *A61F 2/2436* (2013.01); *A61B 2017/22079* (2013.01); *A61B 2017/320024* (2013.01); *A61B 2217/007* (2013.01); *A61F 2230/0067* (2013.01)

(58) Field of Classification Search
CPC .............. A61B 17/22; A61B 17/32002; A61B 2017/22079; A61B 2217/007
See application file for complete search history.

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Nielsen et al. |
| 4,675,361 A | 6/1987 | Ward |
| 5,165,421 A | 11/1992 | Fleischacker et al. |
| 5,263,963 A | 11/1993 | Garrison et al. |
| 5,325,619 A | 7/1994 | Paul |
| 5,334,210 A | 8/1994 | Gianturco |
| 5,354,310 A | 10/1994 | Garnic |
| 5,375,612 A | 12/1994 | Cottenceau |
| 5,376,100 A | 12/1994 | Lefebvre |
| 5,662,671 A | 9/1997 | Barbut |
| 5,733,294 A | 3/1998 | Forber et al. |
| 5,833,650 A | 11/1998 | Imran |
| 5,907,893 A | 6/1999 | Zadno-Azzizi et al. |
| 5,941,896 A | 8/1999 | Kerr |
| 6,135,991 A | 10/2000 | Muni |
| 6,161,547 A | 12/2000 | Barbut |
| 6,221,006 B1 | 4/2001 | Dubrul |
| 6,221,086 B1 | 4/2001 | Forber |
| 6,235,044 B1 | 5/2001 | Root |
| 6,290,710 B1 | 9/2001 | Cryer |
| 6,306,163 B1 | 10/2001 | Fitz |
| 6,361,545 B1 | 3/2002 | Macoviak |
| 6,375,670 B1 | 4/2002 | Greenhalgh |
| 6,383,206 B1 | 5/2002 | Gillick |
| 6,454,775 B1 | 9/2002 | Demarais et al. |
| 6,605,074 B2 | 8/2003 | Zadno-Azizi |
| 6,605,102 B1 | 8/2003 | Mazzocci et al. |
| 6,610,077 B1 | 8/2003 | Hancock |
| 6,620,148 B1 | 9/2003 | Tsugita |
| 6,673,090 B2 | 1/2004 | Root |
| 6,676,682 B1 | 1/2004 | Tsugita |
| 6,706,055 B2 | 3/2004 | Douk |
| 7,575,582 B2 | 8/2009 | Gandhi et al. |
| 7,918,820 B2 | 4/2011 | Stalker |
| 8,038,674 B2 | 10/2011 | Schmaltz |
| 8,221,446 B2 | 7/2012 | Pal |
| 8,361,095 B2 | 1/2013 | Osborne |
| 8,377,092 B2 | 2/2013 | Magnuson |
| 8,784,434 B2 | 7/2014 | Rosenbluth et al. |
| 9,271,818 B2 | 3/2016 | Urbanski |
| 9,579,116 B1 | 2/2017 | Nguyen |
| 9,788,825 B2 | 10/2017 | Whittaker |
| 9,848,975 B2 | 12/2017 | Hauser |
| 9,968,740 B2 | 5/2018 | Pinchuk |
| 9,987,027 B2 | 6/2018 | Ben-Ami |
| 10,016,266 B2 | 7/2018 | Hauser |
| 10,390,817 B2 | 8/2019 | Bonutti |
| 10,500,038 B1 | 12/2019 | Orlov |
| 11,090,460 B2 | 8/2021 | Jaroch |
| 11,103,263 B2 | 8/2021 | Long |
| 2001/0039411 A1 | 11/2001 | Johansson |
| 2002/0062119 A1 | 5/2002 | Zadno-Azizi |
| 2002/0065507 A1 | 5/2002 | Zadno-Azizi |
| 2002/0095171 A1 | 7/2002 | Belef |
| 2002/0169472 A1 | 11/2002 | Douk |
| 2002/0177800 A1 | 11/2002 | Bagaoisan |
| 2003/0104073 A1 | 6/2003 | Johansson |
| 2003/0150821 A1 | 8/2003 | Bates |
| 2003/0187475 A1 | 10/2003 | Tsugita |
| 2005/0004594 A1 | 1/2005 | Nool |
| 2005/0080356 A1 | 4/2005 | Dapolito |
| 2005/0245894 A1 | 11/2005 | Zadno-Azizi |
| 2005/0277976 A1 | 12/2005 | Galdonik |
| 2006/0184194 A1 | 8/2006 | Pal |
| 2006/0200191 A1 | 9/2006 | Zadno-Azizi |
| 2006/0253145 A1 | 11/2006 | Lucas |
| 2006/0271060 A1 | 11/2006 | Gordon |
| 2007/0112374 A1 | 5/2007 | Paul |
| 2007/0156170 A1 | 7/2007 | Hancock |
| 2007/0198028 A1 | 8/2007 | Miloslavski |
| 2007/0208370 A1 | 9/2007 | Hauser |
| 2008/0033341 A1 | 2/2008 | Grad |
| 2008/0033460 A1 | 2/2008 | Ziniti |
| 2008/0195145 A1 | 8/2008 | Bonutti |
| 2008/0208317 A1 | 8/2008 | Jang et al. |
| 2009/0099640 A1 | 4/2009 | Weng |
| 2009/0149881 A1 | 6/2009 | Vale |
| 2009/0326562 A1 | 12/2009 | White |
| 2010/0069948 A1 | 3/2010 | Veznedaroglu et al. |
| 2010/0211087 A1 | 8/2010 | Osborne |
| 2010/0324665 A1 | 12/2010 | Shaw et al. |
| 2011/0098738 A1 | 4/2011 | Hunt |
| 2012/0041538 A1 | 2/2012 | White |
| 2012/0283811 A1 | 11/2012 | Neilan |
| 2013/0030461 A1 | 1/2013 | Marks |
| 2013/0035628 A1 | 2/2013 | Garrison |
| 2013/0072960 A1 | 3/2013 | Schneider |
| 2013/0204278 A1 | 8/2013 | Cully |
| 2013/0253571 A1 | 9/2013 | Bates |
| 2013/0281788 A1 | 10/2013 | Garrison |
| 2013/0345617 A1 | 12/2013 | Wallace |
| 2014/0005540 A1 | 1/2014 | Merhi |
| 2014/0142598 A1 | 5/2014 | Fulton, III |
| 2014/0243878 A1 | 8/2014 | Urbanski |
| 2014/0276403 A1 | 9/2014 | Follmer |
| 2015/0157443 A1 | 6/2015 | Hauser |
| 2015/0164523 A1 | 6/2015 | Brady |
| 2015/0313732 A1 | 11/2015 | Fulton, III |
| 2015/0366649 A1 | 12/2015 | Tafti |
| 2016/0151112 A1 | 6/2016 | Ku et al. |
| 2016/0220265 A1 | 8/2016 | Pokorney |
| 2016/0220741 A1 | 8/2016 | Garrison |
| 2016/0235515 A1 | 8/2016 | Merhi |
| 2016/0249978 A1 | 9/2016 | Lee |
| 2016/0296315 A1 | 10/2016 | Yachia |
| 2016/0317288 A1 | 11/2016 | Rogers |
| 2017/0035445 A1 | 2/2017 | Nguyen |
| 2017/0056169 A1 | 3/2017 | Johnson |
| 2017/0112514 A1 | 4/2017 | Marchand |
| 2017/0238950 A1 | 8/2017 | Yang |
| 2017/0239447 A1 | 8/2017 | Yang |
| 2017/0259042 A1 | 9/2017 | Nguyen |
| 2018/0256177 A1 | 9/2018 | Cooper |
| 2019/0029692 A1 | 1/2019 | Ferrera |
| 2019/0125514 A1 | 5/2019 | Amone |
| 2019/0125534 A1 | 5/2019 | Arcaro |
| 2022/0023073 A1 | 1/2022 | Shirahama |

(56) References Cited

U.S. PATENT DOCUMENTS

2022/0280753 A1    9/2022   Garrison
2023/0277199 A1    9/2023   Duffy

OTHER PUBLICATIONS

Alvarez-Tostado J.A., et al., "The brachial artery: A critical access for endovascular procedures", Journal of Vascular Surgery, 2009, vol. 49, pp. 378-385.
Brekenfeld C., et al., "Impact of retrievable stents on acute ischemic stroke treatment", AJNR Am J Neuroradiol, 2011, vol. 32, pp. 1269-1273.
Brekenfeld C., et al., "Mechanical thromoembolectomy for acute ischemic stroke: Comparison of the catch thrombectomy device and the merci retriever in vivo", Stroke, 2008, vol. 39, pp. 1213-1219, American Heart Association.
Choi S.W., et al., "Low power ultrasound delivered through a PTCA-Like guidewire: Preclinical feasibility and safety of a novel technology for intracoronary thrombolysis", Journal of Interventional Cardiology, 2006, vol. 19, pp. 87-92.
Cousins T.R., et al., "Arterial cannulation: A critical review", AANA Journal, 2004, vol. 72, pp. 267-271.
Di Mario C. Techniques to enhance guide catheter support. Catheter Cardiovasc Interv 2008;72:505-512.
Fitzsimmons B .- F.M., et al., "Rapid stent-supported revascularization in acute ischemic stroke", AJNR 2006, vol. 27, pp. 1132-1134.
Fry D.L., "Acute vascular endothelial changes associated with increased blood velocity gradients", Circulation Research, 1968, vol. 22, pp. 165-197.
Fujita S, Tamai H, Kyo E, et al. New technique for superior guiding catheter support during advancement of a balloon in coronary angioplasty: The anchor technique. Catheter Cardiovasc Interv 2003; 59:482-488.
Gobin Y.P., et al., "In vitro study of hemodynamics in a giant saccular aneurysm model: influence of flow dynamics in the parent vessel and effects of coil embolization", Neuroradiology, 1994, vol. 36, pp. 530-536.
Gralla J., et al., "Mechanical thrombectomy for acute ischemic stroke: Thrombous-device interaction, efficiency, and complications in vivo", Stroke, 2006, vol. 37, pp. 3019-3024.
Graves V.B., et al., "Intracranial arteriovenous malformations: Current imaging and treatment", Investigative Radiology, 1990, vol. 25, pp. 952-960.
Hademenos G., et al., "A biomathematical model of intracranial arteriovenous malformations based on electrical network analysis: Theory and Hemodynamics", Neurosurgery, 1996, vol. 38, pp. 1005-1015.
Hademenos G.J., et al., "The Physics of Cerebral Aneurysms", Physics Today, 1995, pp. 24-30, American Institute of Physics.
Hademenos G.J., et al., "Biophysical mechanisms of stroke", Stroke, 1997, vol. 28, pp. 2067-2077.
Hademenos G.J., et al., "The biophysics of stroke", The Scientific Research Society, 1997, pp. 1-14.
Mahmood, A. Applications of the Distal Anchoring Technique in Coronary and Peripheral Interventions Cath Lab Digest Oct. 2011 vol. 19—Issue 10.
Hart R.G., et al., "Hematologic disorders and ischemic stroke: A selective review", Stroke, 1990, vol. 21, pp. 1111-1121.
Hoffman M., et al., "A cell-based model of hemostasis", Thromb Haemost, 2001, vol. 85, pp. 958-965, Schattauer GmbH, Stuttgart.

Kalyanasundaram A., et al., "Comparison of revascularization procedures in coronary artery disease", Medscape, 2011, http://emedicine.medscape.com/article/164682.
Wilkins R.H., "Cerebral vasospasm", Contemporary Neurosurgery, 1988, vol. 10, pp. 1-6.
Yamada S., et al., "Total blood flow to arteriovenous malformations", Neurological Research, 1993, vol. 15 pp. 383-389.
Zaidat O.O., et al., "Interventional acute ischemic stroke therapy with intracranial self-expanding stent", Stroke, 2008, vol. 39, pp. 2392-2395.
Krajcer Z., et al., "Update on endovascular treatment of peripheral vascular disease", Texas Heart Institute Journal, 2000, pp. 369-385.
Levy E., et al., "Stent-assisted intracranial recanalization for acute stroke: Early Results", Neurosurgery, 2006, vol. 58, pp. 459-463.
Manchola I., et al., "Arteriovenous malformation hemodynamics: A transcranial doppler study", Neurosurgery, 1993, vol. 33, pp. 556-562.
Mehta R., et al., "Race/ethnic differences in the risk of hemorrhagic complications among patients with ischemic stroke receiving thrombolytic therapy", Stroke, 2014, vol. 45, pp. 2263-2269.
Meyers P., et al., "Current status of endovascular stroke treatment", Circulation, 2011, vol. 123, pp. 2591-2601.
Monroe D., et al., "Platelets and thrombin generation", Arteriosclerosis, Thrombosis, and Vascular Biology, Journal of the American Heart Association, 2002, vol. 22, pp. 1381-1389.
Mordasini P., et al., "In vivo evaluation of the first dedicated combined flow-restoration and mechanical thrombectomy device in a swine model of acute vessel occlusion", AJNR, 2011, vol. 32, pp. 294-300.
Mordasini P., et al., "Experimental evaluation of immediate recanalization effect and recanalization efficacy of a new thrombus retriever for acute stroke treatment in vivo", ANJR AM J Neuroradiol, 2013, vol. 354, pp. 153-158.
Mustard J.J., et al., "Factors influencing thrombus formation in vivo", American Journal of Medicine, 1962, vol. 33, pp. 621-647.
Nogueira R.G., et al., "Endovascular approaches to acute stroke, Part 1: Drugs, Devices, and Data", AJNR AM J Neuroradiol, 2009, vol. 30, pp. 649-661.
Nogueira R.G., et al., "Endovascular approaches to acute stroke, Part 2: A comprehensive review of studies and trials", AJNR AM J Neuroradiol, 2009, vol. 30, pp. 859-875.
Nogueira R.G., et al., "Trevo versus merci retrievers for thrombectomy revascularization of large vessel occlusions in acute ischemic stroke (TREVO 2): a randomized trial", Lancet, 2012, vol. 380, pp. 1231-1240.
Ouriel K., "A history of thrombolytic therapy", Ednovasc Ther, 2004, vol. 11, pp. 128-133.
Samaniego E.A., et al., "Stenting in the treatment of acute ischemic stroke: Literature review", Frontiers in Neurology, 2011, vol. 2, pp. 1-7.
Silverberg E., et al., Cancer Statistics, 1990, vol. 40, pp. 9-26.
Singh P., et al., "Endovascular treatment of acute ischemic stroke", Journal of Neurosciences in Rural Practice, 2013, vol. 4, pp. 298-303.
Smith W.S., et al. "Safety and efficacy of mechanical embolectomy in acute ischemic stroke", Stroke, 2005, vol. 36, pp. 1432-1440.
Stein P. D., et al., "Measured turbulence and its effect on thrombus formation" Circulation Research, 1974, vol. 35, pp. 608-614.
Stone G.W., et al., "Safety and efficacy of sirolimus and paclitaxel-eluting coronary stents", The New England Journal of Medicine, 2007, vol. 356, pp. 998-1008.
"The Penumbra Pivotal Stroke", Stroke, 2009, http://stroke.ahajournals.org/content.40/8/2761.full, Crossmark.
Wilkins R.H., "Natural history of intracranial vascular malformations: A review", Neurosurgery, 1985, vol. 16, pp. 421-430.

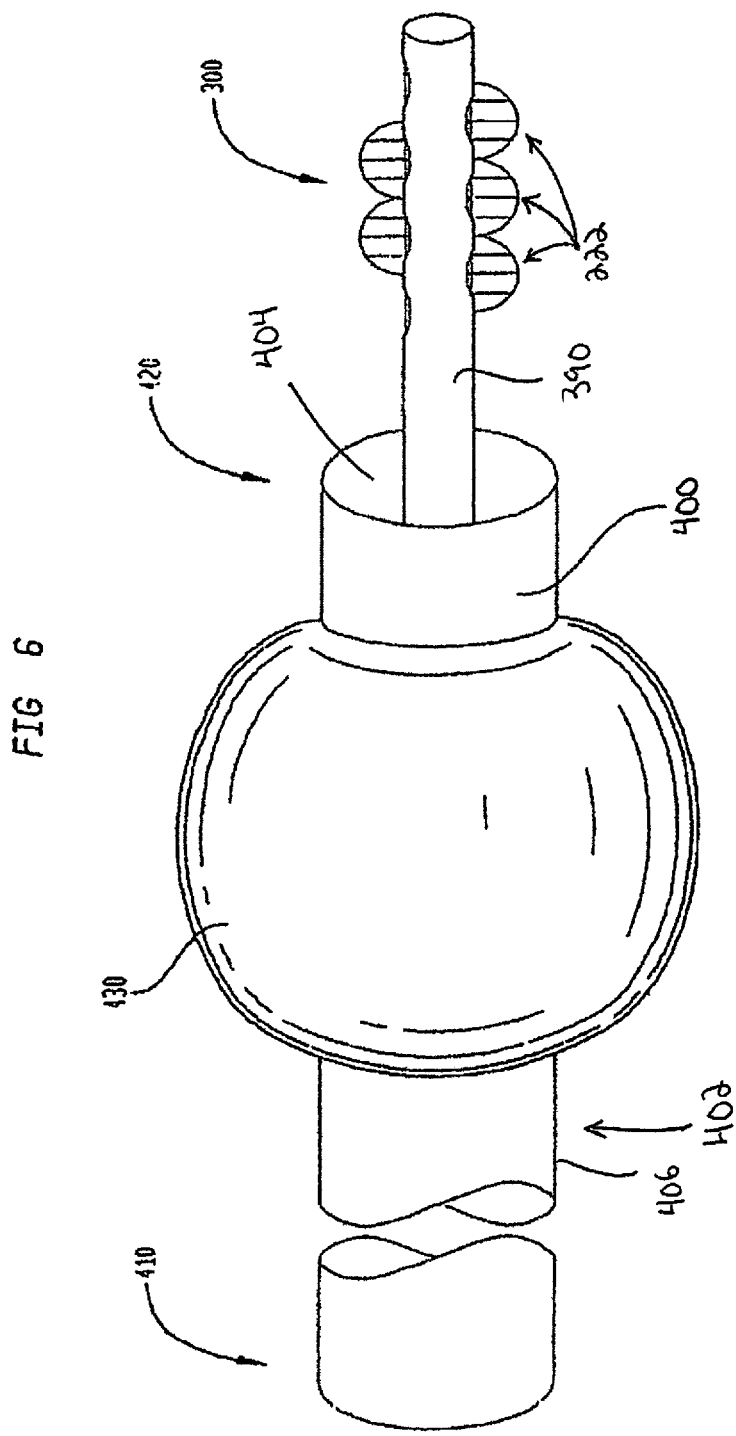

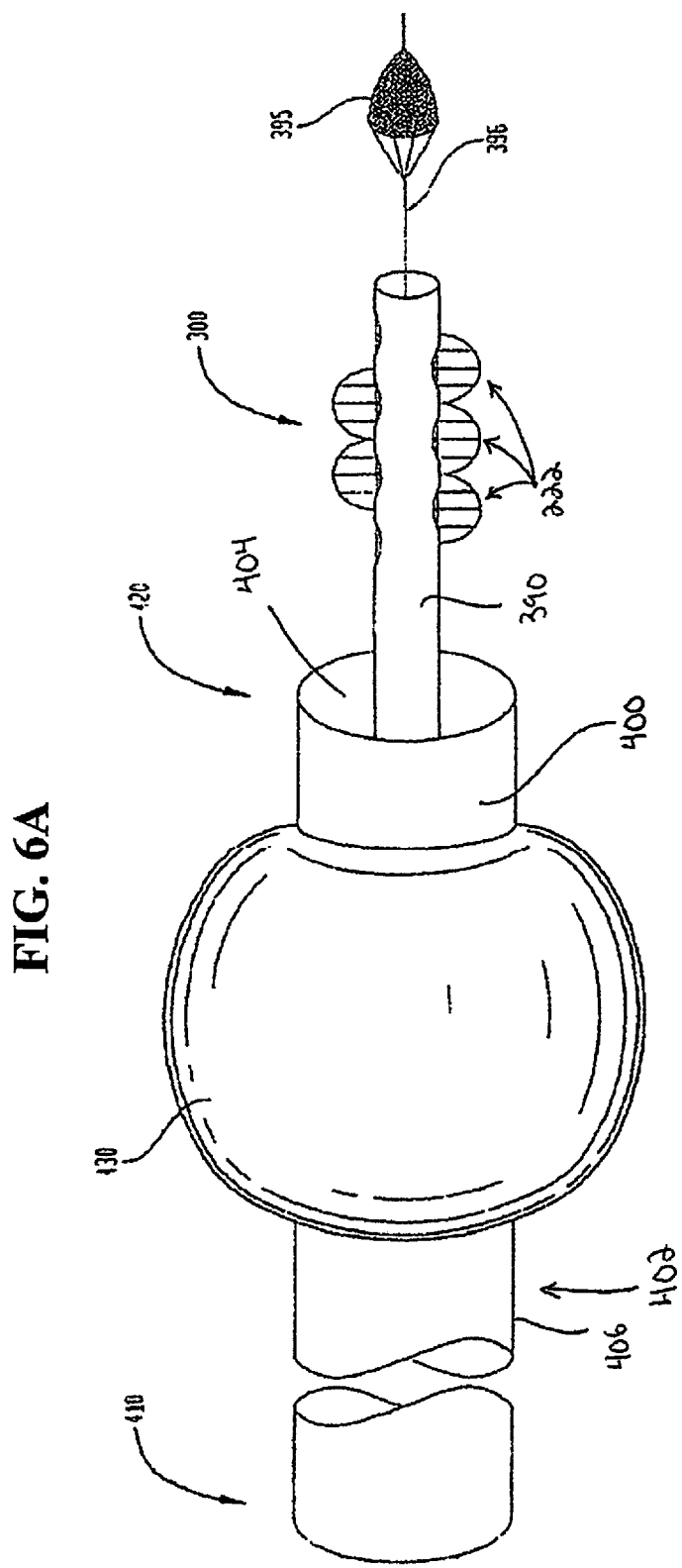

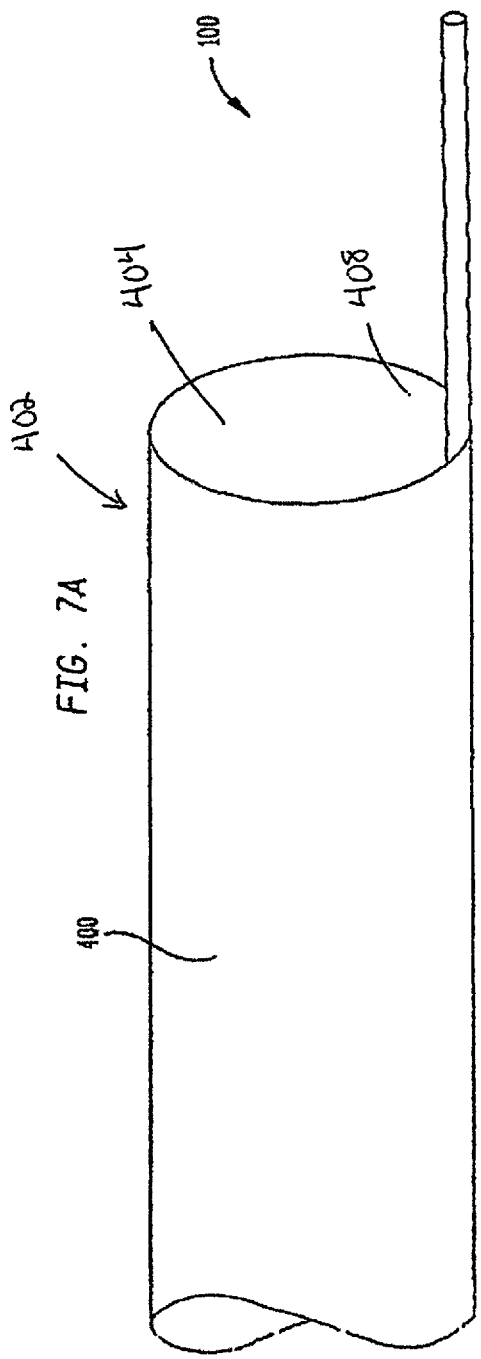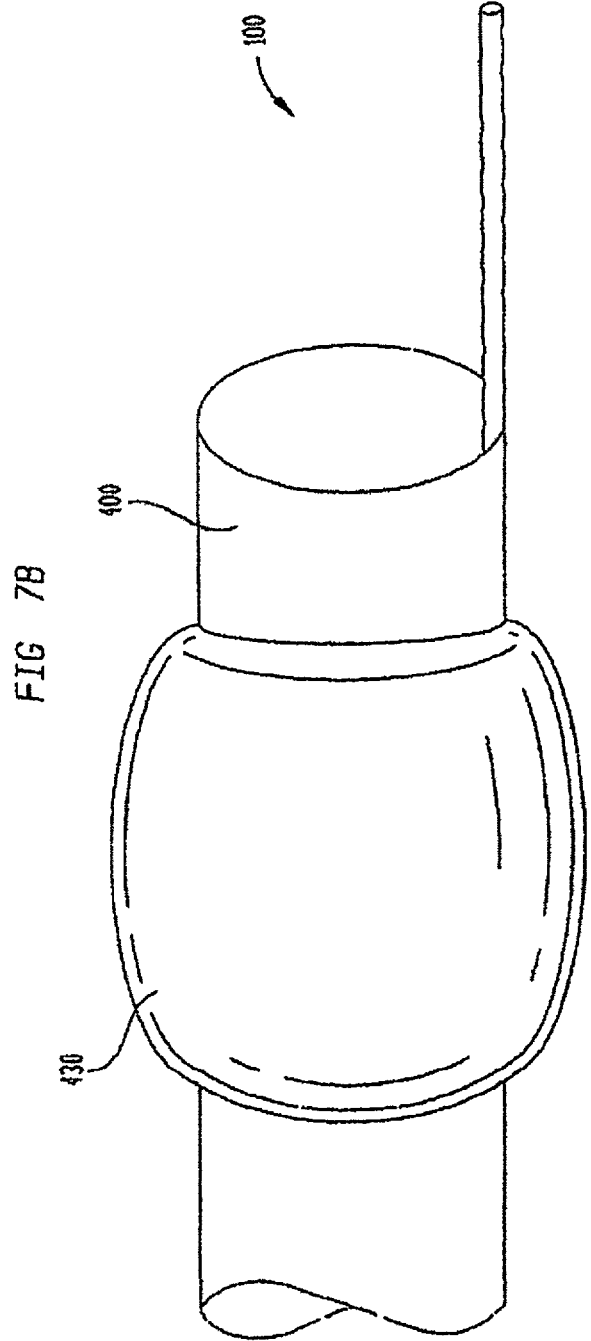

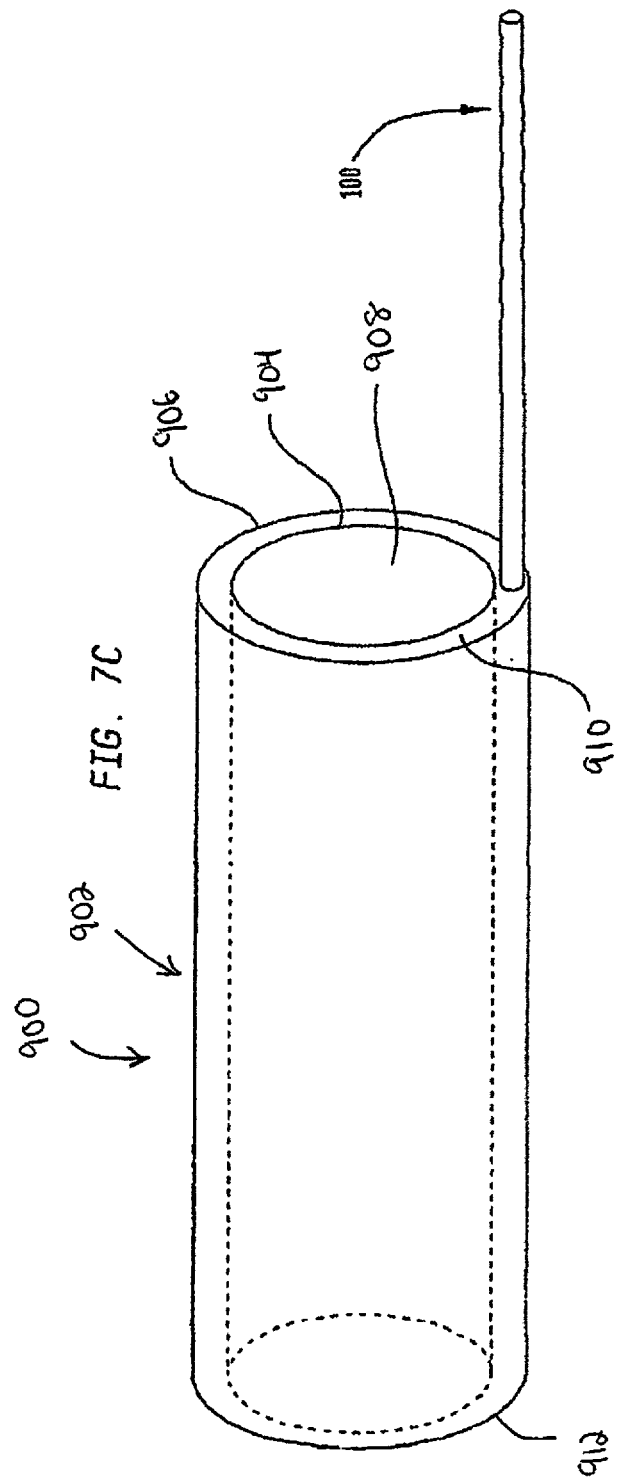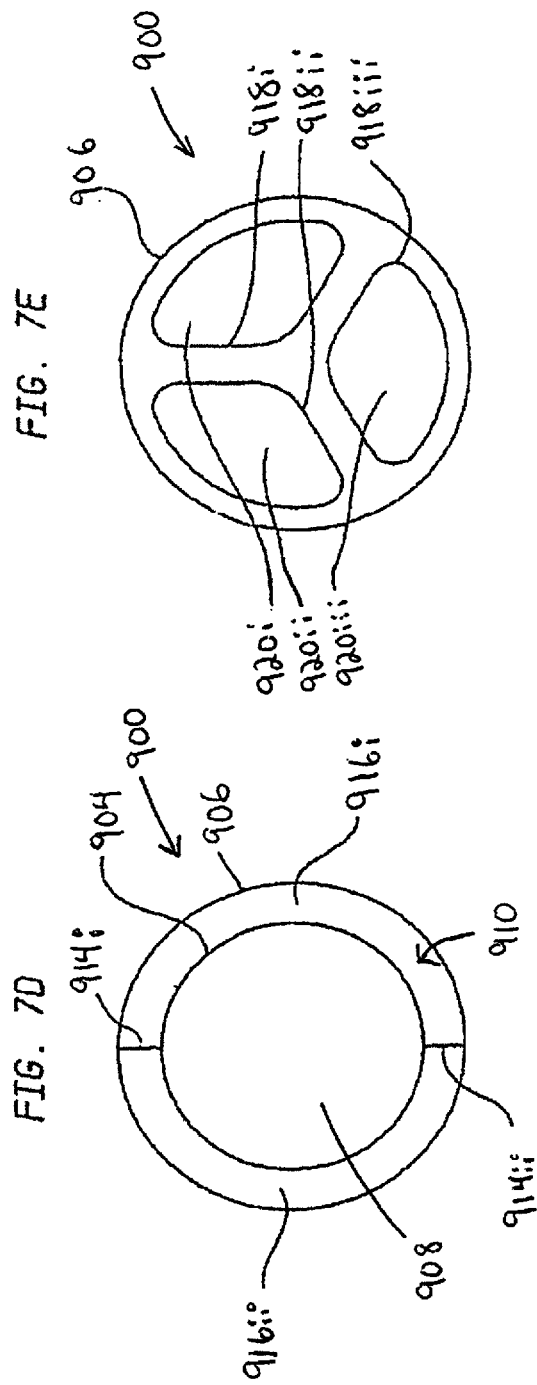

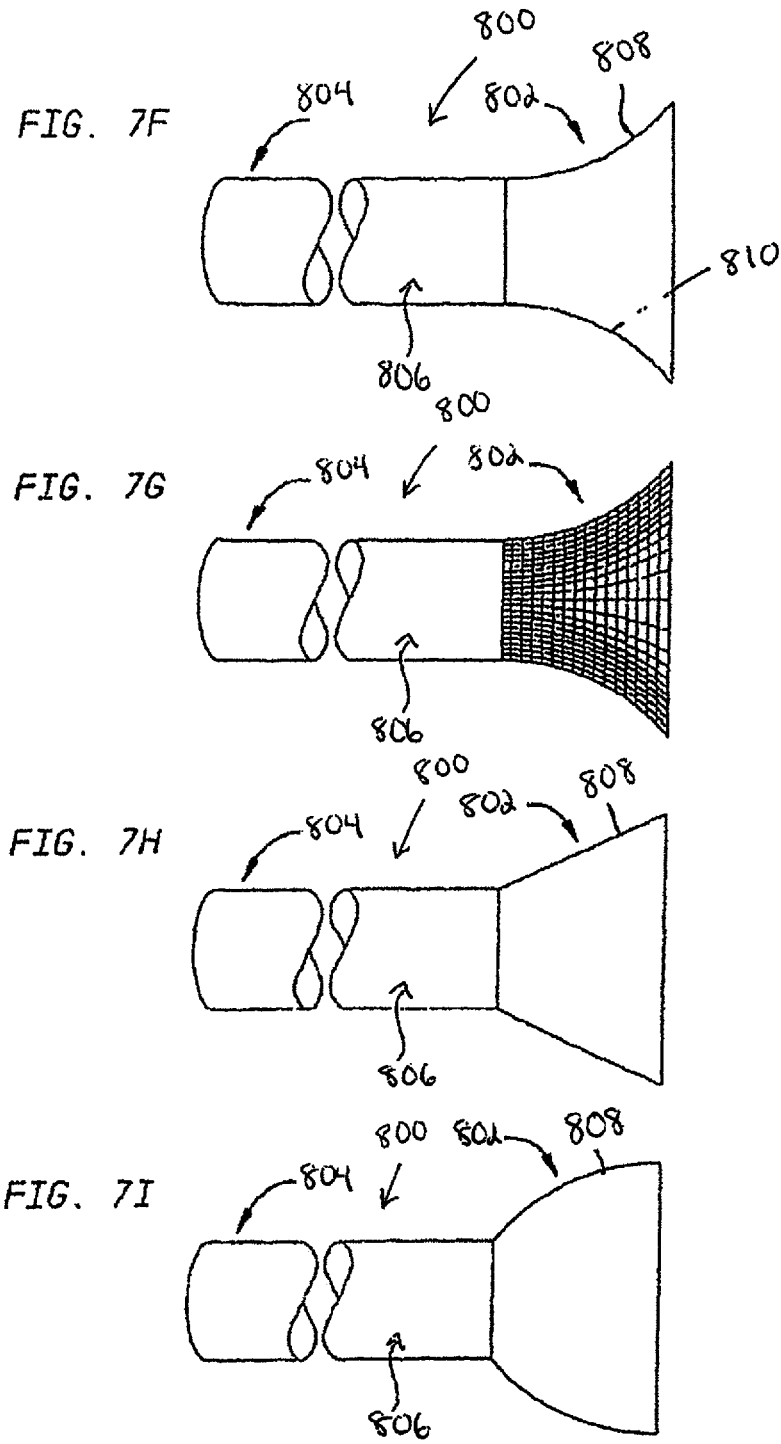

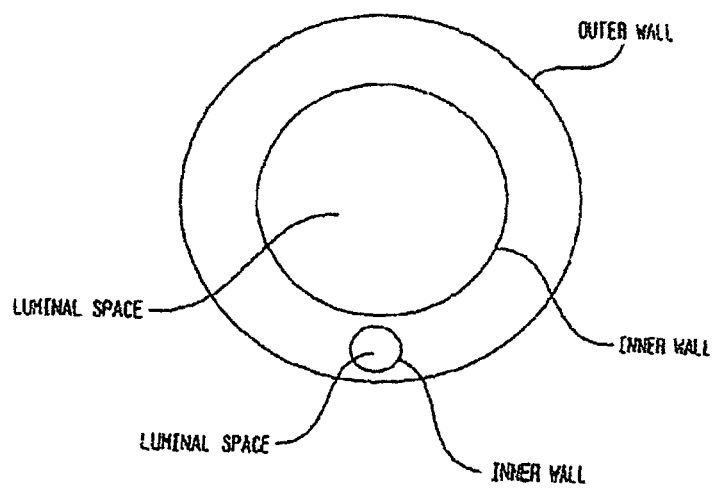
FIG. 7J
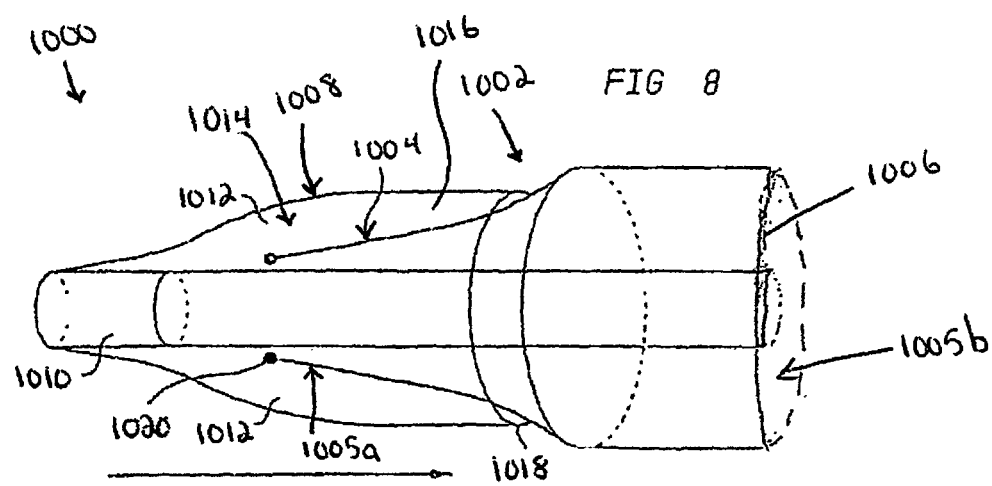
FIG 8
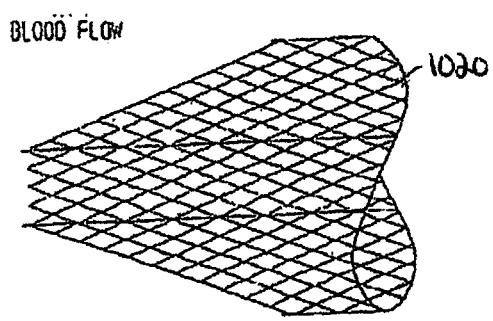

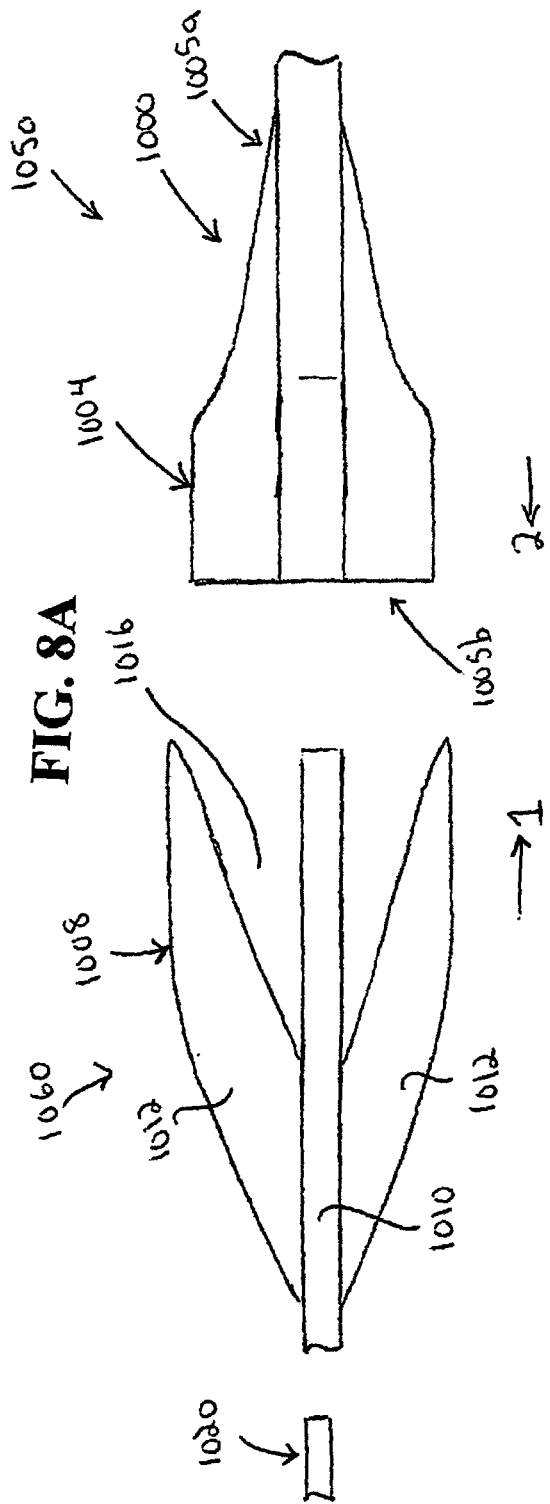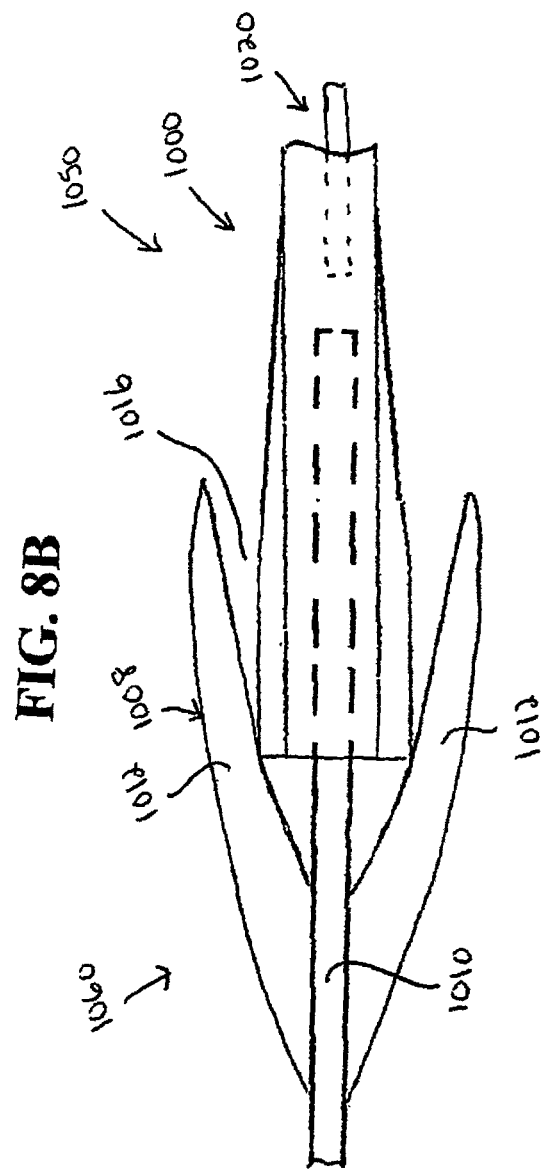
FIG. 8A
FIG. 8B

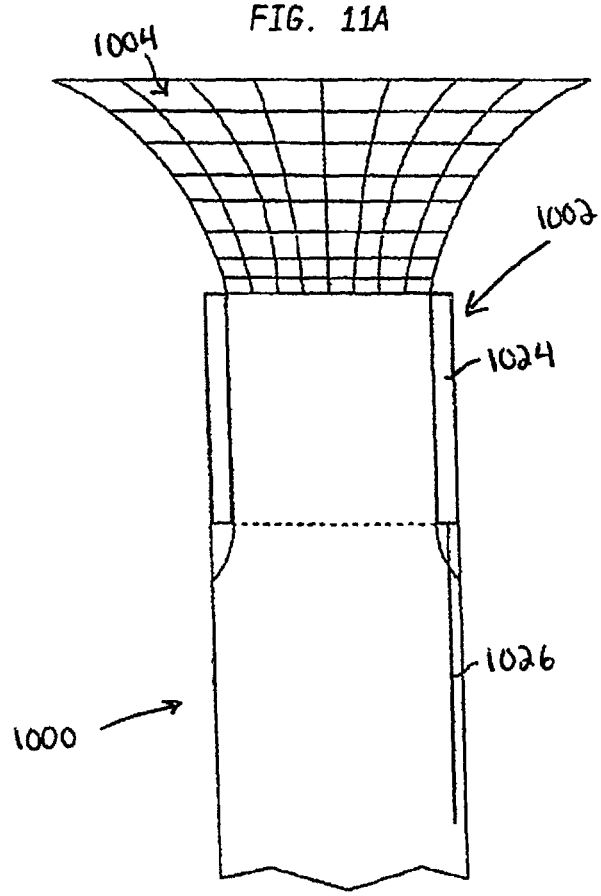
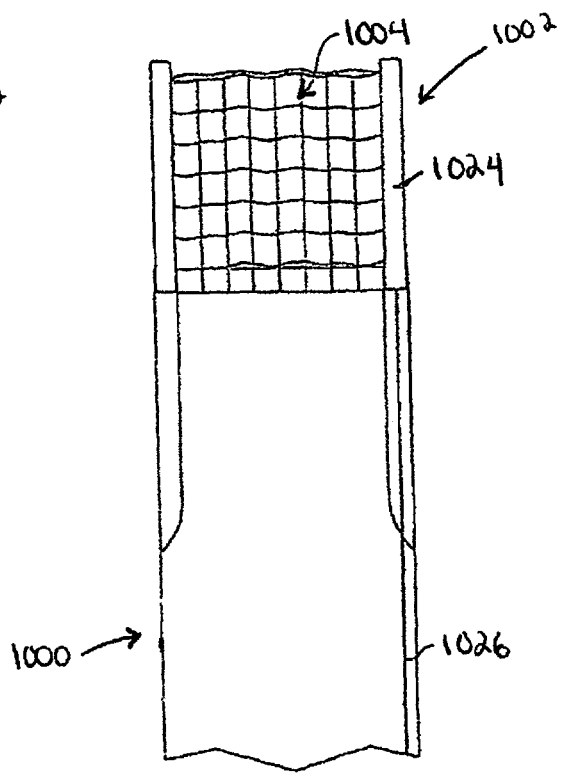

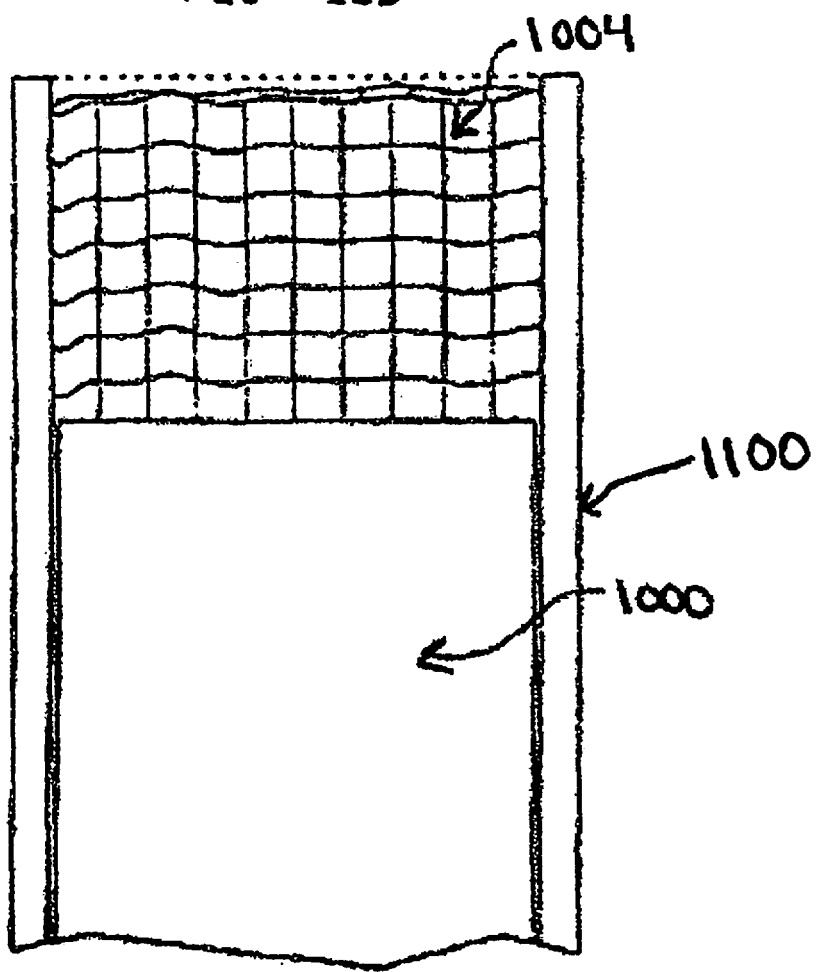

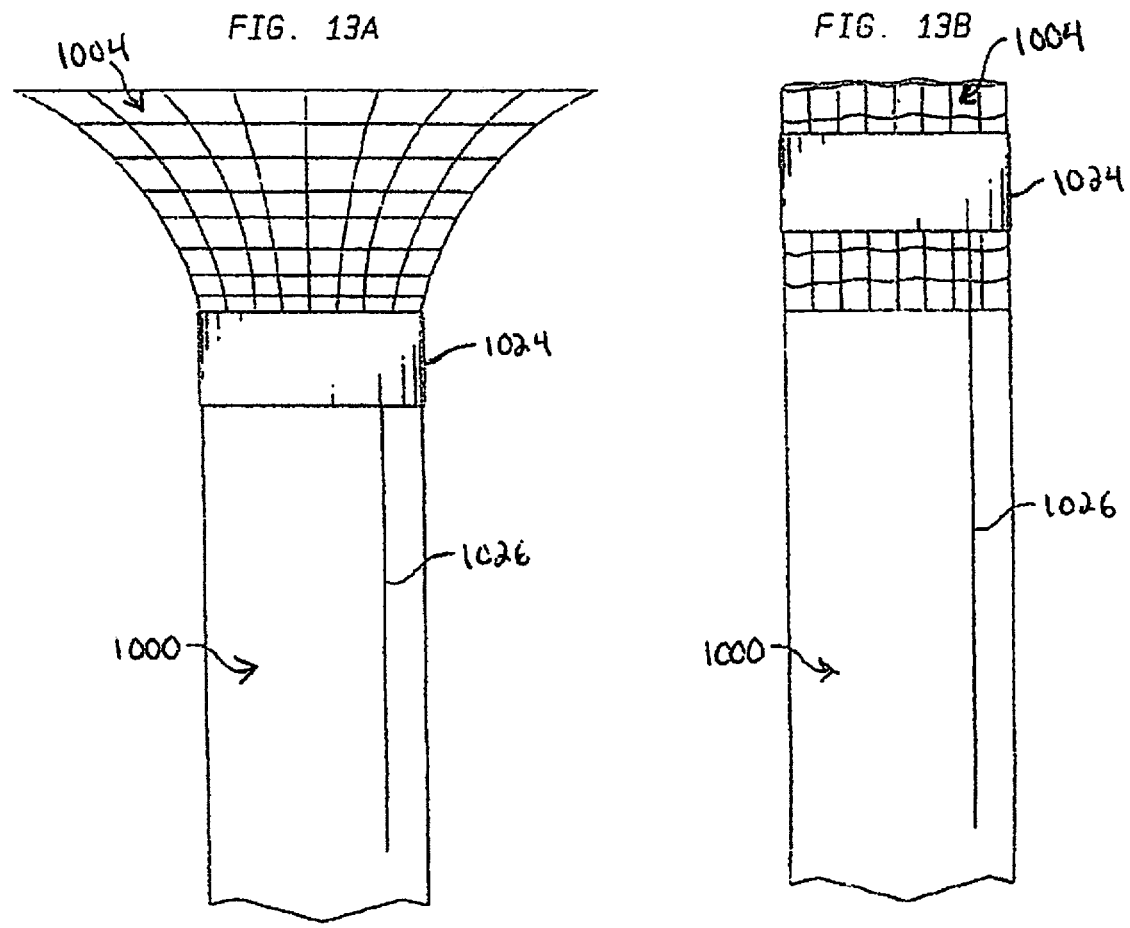
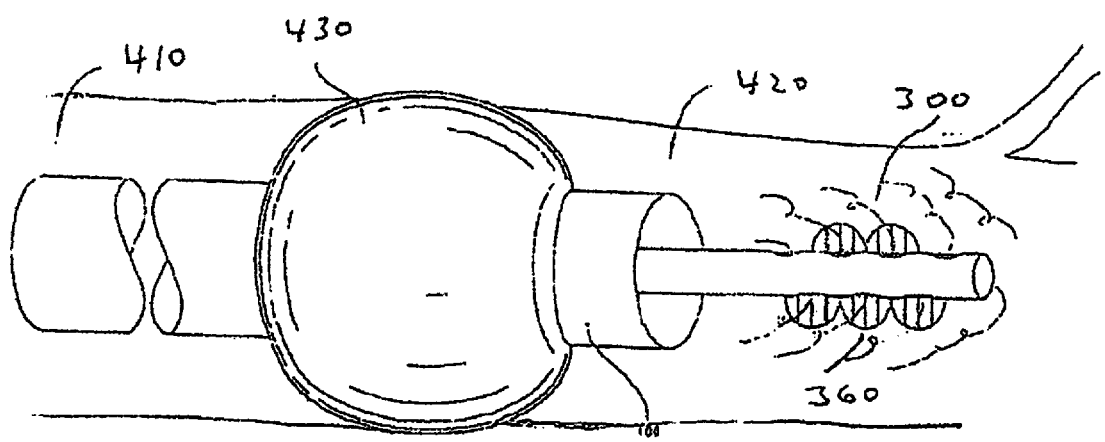

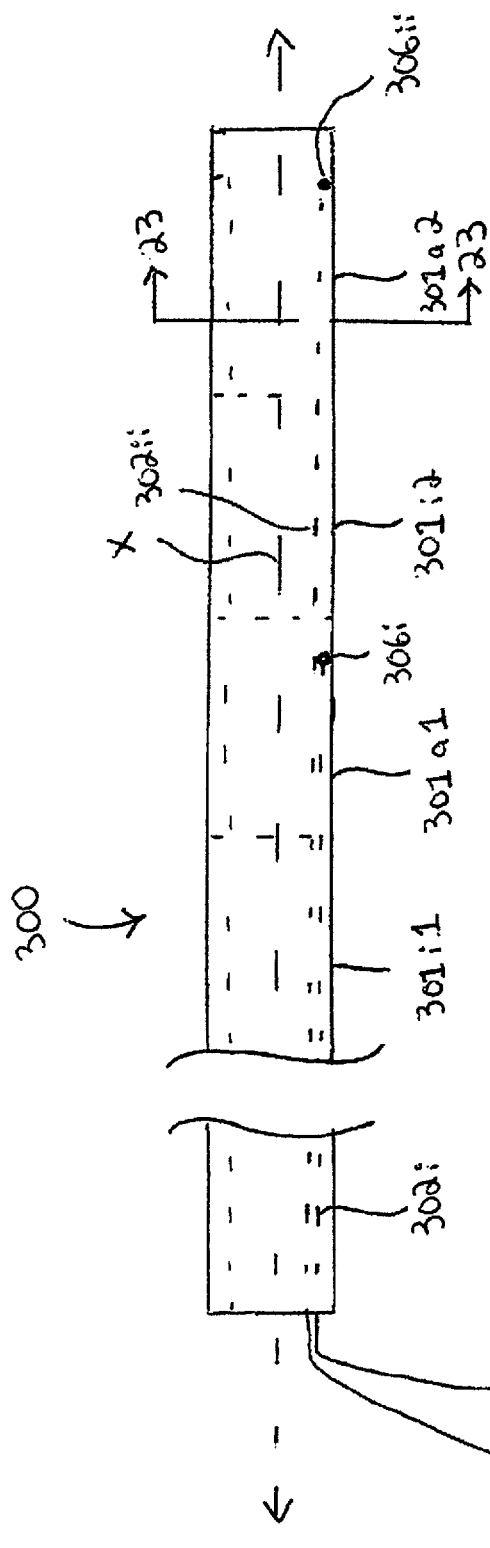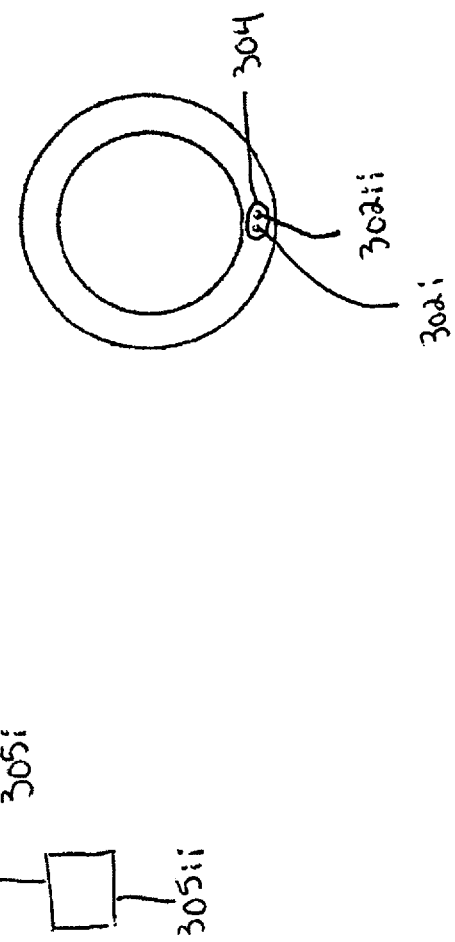
FIG. 22
FIG. 23

ENDOVASCULAR DEVICES AND METHODS WITH FILTERING ELEMENTS

CROSS-REFERENCE TO RELATED APPLICATION(S)

This application is a continuation-in-part of U.S. application Ser. No. 16/501,806, filed on Jun. 10, 2019, which is a continuation-in-part of, U.S. application Ser. No. 16/125,691, filed on Sep. 8, 2018, now U.S. Pat. No. 10,307,242, which is a continuation-in-part of U.S. application Ser. No. 15/731,478, filed on Jun. 16, 2017, now U.S. Pat. No. 10,314,684, which is a continuation-in-part of U.S. application Ser. No. 15/530,898, filed on Mar. 20, 2017, now U.S. Pat. No. 10,299,824, which is a continuation-in-part of U.S. application Ser. No. 15/258,877, filed on Sep. 7, 2016, the entire contents of each of the above-identified applications being hereby incorporated by reference in their entirety.

FIELD OF THE INVENTION

The present disclosure provides methods for one or more medical devices during the course of a vascular procedure, which may be employed individually or in combination with each other, that are adapted for endovascular placement in a minimally invasive (e.g., percutaneous) manner.

For example, the present disclosure envisions a first medical device that is configured for irrigation, aspiration, and/or maceration to safely and effectively perform a thrombectomy procedure (or the like). The second device that is configured as a bypass catheter (e.g., to ameliorate ischemic injury).

BACKGROUND OF THE INVENTION

Prior Art

The prior art is replete with documentation as to the direct and indirect adverse health effects associated with the presence of solid matter within an individual's vascular system. One common example of said matter is a thrombus. A wide variety of techniques are known for removing said mater from a vascular system. Said techniques often use, independently, both electrical and mechanical thrombus maceration devices, irrigation devices or aspiration devices. Typically, said techniques attempt to dislodge said solid matter from the contours of the vascular system, if necessary, and then remove said solid matter from the vascular system by means of suction or the like or retrieval devices.

For purposes of thrombectomy some skilled persons (usually doctors) use one or more tools such as mechanical thrombus maceration devices, irrigation devices, clot retrieval devices and aspiration devices.

The application of irrigation alone into a blockage (e.g., a clot) would tend to propagate any loose pieces, whether they are existing loose pieces or lose pieces created by maceration. In particular, in the context of arterial blockages, irrigation alone would tend to propagate the loose pieces distally into the smaller arteries and capillary beds. Once they get that far distal, they will clog the capillary beds, cannot be retrieved, and will cause permanent ischemic injury to the tissues. By applying simultaneous proximal aspiration, while occluding the blood vessel with a wedged occlusive size catheter, a catheter with a balloon inflated on the tip, or another device or method, flow at the site of the blockage and the artery beyond will be reversed, and loose pieces will flow retrograde into the aspiration catheter and out of the body, rather than traveling downstream and making matters worse. With the flow reversed for safety the irrigation will prevent an empty vacuum where nothing will flow which can occur when there is no collateral flow into a vessel to which aspiration is applied, and will prevent collapse of the artery from the vacuum that also would not allow flow.

In the context of venous blockages, the same principles apply. Specifically, that the user must prevent the showering of debris (e.g., loose pieces of a blockage, clot, or other such emboli) to the capillary beds of the at-risk tissue, but the at-risk tissue is different, based on the direction of flow. In venous blockages, the at-risk tissue is in the heart and lungs, as the venous flow takes the blood back to the right side of the heart and then the lungs. So, in most venous cases the key is to capture debris before reaching the heart or lungs. Venous cases have a further disadvantage that the blood vessels with thrombus are typically much larger, so if continuous simultaneous aspiration was applied, the patient could have massive blood loss. On the other hand, venous cases have the advantage, in most cases, that they can be approached easily from either side of the blockage, from below and above (further from the heart and closer to the heart). For example (non-limiting), an iliac blockage can be approached with an irrigating macerator, or a plain macerator, from below via the femoral vein, or from above. A novel filter aspirator described by the current disclosure can then be introduced into the internal jugular vein in the neck, advanced over a wire down through the right atrium of the heart and deployed in the inferior vena cava, above the blockage, so all showered pieces end up in the filter, and not in the capillary beds of the heart and lungs (small pieces) or in the main pulmonary arteries (larger pieces), which can cause life threatening hemodynamic instability (a classic large pulmonary embolus). In some cases, the macerator can be introduced directly through the novel filter aspirator as well. The aspiration on the filter aspirator could only be turned on intermittently, to clear out the blockage accumulating at the filter, so as to avoid the massive blood loss that could otherwise occur if the aspiration was on continuously in these cases. In an alternative setup the macerating tool could also be introduced through the filter aspirator. A similar application of this novel filter aspirator could be used to capture and remove emboli during a procedure in which a blockage is removed from an obstructed dialysis arterio venous graft fistula. In this case the filter aspirator would more often be introduced via a distant vein such as the femoral vein (or other entry veins), and deployed in the axillary vein or the Subclavian vein. The method here is in contrast to the arterial example above, where blood flow to that arterial territory is intentionally occluded, so very little blood is aspirated (e.g., such that the majority of material removed is comprised of irrigation fluid and debris). Rather, normal blood component are allowed to continue to flow through the semi-permeable filter, while the filter captures clot and debris. Furthermore, in most arterial applications, even when there is back bleeding from collateral flow, the blood vessels are often much smaller, so flow rate of blood that can be lost is much lower. Additionally, the aspiration of the arterial device is performed with proximal vessel occlusion, which would limit blood flow, and hence blood aspiration and blood loss, even in larger vessels.

In venous thrombectomy cases the described technique is currently not done because a similar filter aspirator does not exist.

If it did exist and aspiration was applied continuously, in many of these cases there could be massive, often life-threatening, blood loss.

In arterial thrombectomy cases irrigation is not used with the aspiration because in smaller arteries there is a technical/engineering challenges of making a device small enough to effectively irrigate through and macerate, while not functionally obstructing the aspiration catheter. If the device fills too much of the aspiration catheter, the effective diameter of the aspiration catheter is reduced tremendously. Flow is inversely proportional to the fourth power of diameter $$R = \frac{8L\eta}{\pi r^4}$$

where r=inside radius of the blood vessel, L=blood vessel length, and n=blood viscosity. It is important to note that a small change in blood vessel radius will have a very large influence (4th power) on its resistance to flow; e.g., decreasing blood vessel diameter by 50% will increase its resistance to flow by approximately 16-fold. More particularly, if one combines the preceding two equations into one expression, which is commonly known as the Poiseuille equation, it can be used to better approximate the factors that influence flow through a cylindrical blood vessel:

$$Q = \frac{\Delta P \pi r^4}{8L\eta}$$

In arterial thrombectomy cases without irrigation aspiration may lead to the collapse of a blood vessel.

Additionally, the art would lead a skilled person away from the present disclosure's simultaneous combination because the simultaneous use of an irrigation device and aspiration device are counter synergistic (i.e. they would cancel out each other's intended benefit). Consequently, the prior art teaches the use of the serial use of an irrigation device and then an aspiration device.

Accordingly, it would be desirable to provide a means of applying a simultaneous combination of irrigation, aspiration and maceration to a thrombus or similar material in many arterial clot cases. In many venous clot cases combinations of maceration, irrigation, and aspiration via the described novel devices can be applied simultaneously or in alternating fashions, as well as sometimes intermittently Blood Vessel Structure and Function Blood vessels are dynamic structures that constrict, relax, pulsate, and proliferate. Within the body, blood vessels form a closed delivery system that begins and ends at the heart. There are three major types of blood vessels: (i) arteries; (ii) capillaries and (iii) veins. As the heart contracts, it forces blood into the large arteries leaving the ventricles. Blood then moves into smaller arteries successively, until finally reaching the smallest branches, the arterioles, which feed into the capillary beds of organs and tissues. Blood drains from the capillaries into venules, the smallest veins, and then into larger veins that merge and ultimately empty into the heart.

Arteries carry blood away from the heart and "branch" as they form smaller and smaller divisions. In contrast, veins carry blood toward the heart and "merge" into larger and larger blood vessels approaching the heart. In the systemic circulation, arteries carry oxygenated blood and veins carry oxygen-poor blood. In the pulmonary circulation, the opposite is true. The arteries (still defined as the blood vessels leading away from the heart), carry oxygen-poor blood to the lungs, and the veins carry oxygen-rich blood from the lungs to the heart.

The only blood vessels that have intimate contact with tissue cells in the human body are capillaries. In this way, capillaries help serve cellular needs. Exchanges between the blood and tissue cells occur primarily through the thin capillary walls.

The walls of most large blood vessels (an exception being the smallest blood vessels, e.g., venules), have three layers, or tunics, that surround a central blood-containing space called the blood vessel lumen.

The innermost tunic (layer) is the tunica intima. The tunica intima contains the endothelium, the simple squamous epithelium that lines the lumen of all blood vessels. The endothelium is continuous with the endocardial lining of the heart, and its flat cells fit closely together, forming a slippery surface that minimizes friction so blood moves smoothly through the lumen. In blood vessels larger than 1 mm in diameter, a sub-endothelial layer, consisting of a basement membrane and loose connective tissue, supports the endothelium.

The middle tunic (layer), the tunica media, is mostly circularly arranged smooth muscle cells and sheets of elastin. The activity of the smooth muscle is regulated by sympathetic vasomotor nerve fibers of the autonomic nervous system. Depending on the body's needs at any given time, regulation causes either vasoconstriction (lumen diameter decreases) or vasodilation (lumen diameter increases). The activities of the tunica media are critical in regulating the circulatory system because small changes in blood vessel diameter greatly influence blood flow and blood pressure. Generally, the tunica media is the bulkiest layer in arteries, which bear the chief responsibility for maintaining blood pressure and proper circulation.

The outer layer of a blood vessel wall, the tunica externa, is primarily composed of collagen fibers that protect the blood vessel, reinforce the blood vessel, and anchor the blood vessel to surrounding structures. The tunica externa contains nerve fibers, lymphatic vessels, and elastic fibers (e.g., in large veins). In large blood vessels, the tunica externa contains a structure known as the vasa vasorum, which literally means "vessels of vessels". The vasa vasorum nourishes external tissues of the blood vessel wall. Interior layers of blood vessels receive nutrients directly from blood in the lumen (See, e.g., The Cardiovascular System at a Glance, 4th Edition, Philip I. Aaronson, Jeremy P. T. Ward, Michelle J. Connolly, November 2012, 2012, Wiley-Blackwell, Hoboken, N.J.).

Cerebral Arteries

FIGS. 1 and 2 show schematic illustrations of the brain's blood vessels. Each cerebral hemisphere is supplied by an internal carotid artery, which arises from a common carotid artery beneath the angle of the jaw, enters the cranium through the carotid foramen, traverses the cavernous sinus, penetrates the dura and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it gives off the ophthalmic artery, which supplies the eye, and it also gives off the anterior choroidal artery, which supplies the anterior hippocampus and, at a caudal level, the posterior limb of the internal capsule. Each vertebral artery typically arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, pp. 854-56 (1985)).

Interconnections between blood vessels (anastomoses) protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

Hemorrhage

Blood vessels are typically structurally adept to withstand the dynamic quantities required to maintain circulatory function. For reasons that are not entirely understood, the blood vessel wall can become fatigued and abnormally weak and possibly rupture. With blood vessel rupture, hemorrhage (meaning the escape of blood from a ruptured blood vessel) occurs with blood seeping into the surrounding brain tissue. As the blood accumulates within the brain, the displaced volume causes the blood, now often thrombosed (blocked, clotted), to ultimately compress the surrounding blood vessels. The compression of blood vessels can translate into a reduced blood vessel diameter and a corresponding reduction in flow to surrounding tissue, thereby enlarging the insult (See, e.g., Hademenos G. J. and Massoud T. F. Stroke 1997; 28:2067-2077).

In the brain, hemorrhage may occur at the brain surface (extraparenchymal), for example, from the rupture of aneurysms at the circle of Willis, causing subarachnoid hemorrhage (SAH). Hemorrhage also may be intraparenchymal, for example, from rupture of blood vessels damaged by long-standing hypertension, and may cause a blood clot or an intracerebral hematoma within the cerebral hemispheres, in the brain stem, or in the cerebellum. Hemorrhage may be accompanied by ischemia or infarction. The mass effect of an intracerebral hematoma may compromise the blood supply of adjacent brain tissue; or SAH may cause reactive vasospasm of cerebral surface blood vessels, leading to further ischemic brain damage. Infarcted tissue may also become secondarily hemorrhagic. Among the vascular lesions that can lead to hemorrhagic strokes are aneurysms and arteriovenous malformations (AVMs) (See, e.g., Hademenos G. J. and Massoud T. F. Stroke 1997; 28:2067-2077).

Coagulation

Hemostasis is the cessation of blood loss from a damaged (injured) blood vessel. Platelets first adhere to macromolecules in the subendothelial regions of the injured blood vessel; they then aggregate to form a primary hemostatic plug. Platelets stimulate local activation of plasma coagulation factors, leading to the generation of a fibrin blockage that reinforces the platelet aggregate. Later, as wound healing occurs, the platelet aggregate and the fibrin blockage are degraded as wound healing, ensues (Goodman & Gilman's The Pharmacological Basis of Therapeutics, Joel G. Hardman and Lee E. Limbird, Eds, McGraw-Hill, 2001, p. 1519-20).

Coagulation involves a series of zymogen activation reactions. At each stage, a precursor protein, or zymogen, is converted to an active protease by cleavage of one or more peptide bonds in the precursor molecule. The components that can be involved at each stage include a protease from the preceding stage, a zymogen, a non-enzymatic protein cofactor, calcium ions, and an organizing surface that is provided by the damaged blood vessel and platelets in vivo. The final protease to be generated is thrombin (factor IIa).

Fibrinogen is a 330,000 dalton protein that consists of three pairs of polypeptide chains (designated .alpha., .beta. and .gamma.) covalently linked by disulfide bonds. Thrombin converts fibrinogen to fibrin monomers (Factor IA) by cleaving fibrinopeptides A (16 amino acid residues) and B (14 amino acid residues) from the amino-terminal ends of the .alpha. and .beta. chains respectively. Removal of the fibrinopeptides allows the fibrin monomers to form a gel. Initially, the fibrin monomers are bound to each other non-covalently. Subsequently, factor XIIIa catalyzes an interchain trans-glutamination reaction that cross-links adjacent fibrin monomers.

Fibrin participates in both the activation of Factor XIII by thrombin and activation of plasminogen activator (t-PA). It specifically binds the activated coagulation factors factor Xa and thrombin and entraps them in the network of fibers, thus functioning as a temporary inhibitor of these enzymes which stay active and can be released during fibrinolysis. Recent research comprises shown that fibrin plays a key role in the inflammatory response.

The protease zymogens involved in coagulation include factors II (prothrombin), VII, IX, X, XI, XII, and prekallikrein. Factors V and VIII are homologous 350,000 dalton proteins. Factor VIII circulates in plasma bound to von Willebrand factor, while factor V is present both free in plasma and as a component of platelets. Thrombin cleaves V and VIII to yield activated factors (Va and VIIIa) that have at least 50 times the coagulant activity of the precursor forms. Factors Va and VIIIa have no enzymatic activity themselves, but serve as cofactors that increase the proteolytic efficiency of Xa and IXa, respectively. Tissue factor (TF) is a non-enzymatic lipoprotein cofactor that greatly increases the proteolytic efficiency of VIIa. It is present on the surface of cells that are not normally in contact with blood and plasma (e.g. fibroblasts and smooth muscle cells) since they are abluminal to (meaning on the outer surface of a body part with an internal cavity or channel) the endothelium. TF is a key factor that initiates coagulation outside a broken blood vessel.

Two pathways of coagulation are recognized: the intrinsic coagulation pathway, so called because all of the components are intrinsic to plasma, and an extrinsic coagulation pathway. The extrinsic and intrinsic systems converge to activate the final common pathways causing fibrin formation. It generally is recognized that these systems are somewhat artificial distinctions and do not reflect accurately the coagulation cascades that occur in vivo. Hoffman, M., and Monroe, D. M. III, "A Cell-based Model of Hemostasis," Thromb. Haemost. 85:958-65 (2001). Tissue factor exposed by tissue injury, either traumatically, by disease or surgery, can activate sufficient factors X, IX and thrombin (II) to initiate coagulation.

The extrinsic system (tissue factor (TF) pathway) generates a thrombin burst and is initiated when tissue thromboplastin activates Factor VII. Upon blood vessel injury, TF is exposed to the blood and enzyme coagulation Factor VII (proconvertin) circulating in the blood. Once bound to TF, Factor VII is activated to Factor VIIa by different proteases, including thrombin (Factor IIa), Factor Xa, Factor IXa, Factor XIIa and the Factor VIIa-TF complex itself. The Factor VIIa-TF complex activates Factors IX and X. The activation of Factor Xa by Factor VIIa-TF almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including Factor V and Factor VIII (which activates Factor XI, which, in turn, activates Factor IX), and activates and releases Factor VIII from being bound to vWF (von Willebrand Factor). Factor VIIa and Factor IXa together they form the "tenase" complex, which activates Factor X, and so the cycle continues.

The intrinsic system (contact activation pathway) is initiated when blood contacts any surface except normal endothelial and blood cells. The intrinsic system begins with formation of the primary complex on collagen by high-molecular weight kininogen (HMWK), prekallikrein, and FXII (Hageman factor). Prekallikrein is converted to kallikrein and Factor XII becomes Factor XIIa. Factor XIIa converts Factor XI into Factor XIa. Factor XIa activates Factor IX, which, with its co-factor Factor VIIIa form the tenase complex, which activates Factor X to Factor Xa.

The prevailing view of hemostasis remains that the protein coagulation factors direct and control the process with cells serving primarily to provide a phosphatidylserine containing surface on which the procoagulant complexes are assembled. In contrast, a model in which coagulation is regulated by properties of cell surfaces, which emphasized the importance of specific cellular receptors for the coagulation proteins, comprises been proposed. Hoffman, M., and Monroe, D. M. III, "A Cell-based Model of Hemostasis," Thromb. Haemost. 85:958-65 (2001). Thus, cells with similar phosphatidylserine content can play very different roles in hemostasis depending on their complement of surface receptors. These authors propose that coagulation occurs not as a "cascade", but in three overlapping stages: 1) initiation, which occurs on a tissue factor bearing cell; 2) amplification, in which platelets and cofactors are activated to set the stage for large scale thrombin generation; and 3) propagation, in which large amounts of thrombin are generated on the platelet surface. This cell-based model explains some aspects of hemostasis that a protein-centric model does not.

Modeling Hemostasis

As currently understood, coagulation in vivo is a 3-step process centered on cell surfaces (see Monroe Arterioscler Thromb Vasc Biol. 2002; 22:1381-1389). In the first step, coagulation begins primarily by initiation with tissue factor (TF), which is present on the subendothelium, tissues not normally exposed to blood, activated monocytes and endothelium when activated by inflammation. Factors VII and VIIa bind to TF and adjacent collagen. The factor VIIa, tissue factor complex activates factor X and IX. Factor Xa activates factor V, forming a prothrombinase complex (factor Xa, Va and calcium) on the TF-expressing cell. In the second step, coagulation is amplified as platelets adhere to the site of injury in the blood vessel. Thrombin is activated by platelet adherence and then acts to fully activate platelets, enhance their adhesion and to release factor V from the platelet granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin (also called the thrombin burst). Propagation, the third step, is a combination of activation of the prothrombinase complexes that allow large amounts of thrombin to be generated from prothrombin. More platelets can be recruited, as well as activation of fibrin polymers and factor XIII.

Natural Anticoagulant Mechanisms

Platelet activation and coagulation normally do not occur within an intact blood vessel. Thrombosis (meaning a pathological process in which a platelet aggregate and/or a fibrin blockage occludes a blood vessel) is prevented by several regulatory mechanisms that require a normal vascular endothelium. Prostacyclin (PGI2), a metabolite of arachidonic acid synthesized by endothelial cells, inhibits platelet aggregation and secretion. Antithrombin is a plasma protein that inhibits coagulation factors of the intrinsic and common pathways. Heparan sulfate proteoglycans synthesized by endothelial cells stimulate the activity of antithrombin. Protein C is a plasma zymogen homologous to Factors II, VII, IX, and X. Activated protein C in combination with its nonenzymatic cofactor (Protein S) degrades cofactors Va and VIIIa and thereby greatly diminishes the rate of activation of prothrombin and factor X. Protein C is activated by thrombin only in the presence of thrombomodulin, an integral membrane protein of endothelial cells. Like antithrombin, protein C appears to exert an anticoagulant effect in the vicinity of intact endothelial cells. Tissue factor pathway inhibitor (TFPI), which is found in the lipoprotein fraction of plasma, when bound to factor Xa, inhibits factor Xa and the factor VIIa-tissue factor complex.

Thrombosis

Thrombosis refers to the formation of a thrombus, (e.g., a blood clot or other such blockage) comprising platelets, fibrin, leukocytes, and red blood cells located within a vascular lumen (Rubin's Pathology, Raphael Rubin and David S. Strayer, ed., 5th Ed., Lippincott Williams & Wilkins: 2008, page 233). A thrombus can be distinct from a typical blood clot. While a blood clot results from activation of the coagulation cascade, a thrombus also involves adherence and aggregation of platelets, participation of cellular elements of the immune system, and active participation of endothelial cells of the blood vessel (Id.).

Before injury to a blood vessel, circulating platelets are in a nonadherent state. Injury activates platelet adhesiveness, after which platelets bind to one another to form an aggregate of activated platelets (platelet thrombus) (Id. at 394). These platelet aggregates occlude injured small blood vessels and prevent leakage of blood. Once platelets are stimulated to adhere to the blood vessel wall, their granular contents are released, in part by contraction of the platelet cytoskeleton. In turn, these granules promote aggregation of other platelets. Platelet adhesion is enhanced by release of subendothelial von Willebrand factor, which is adhesive for Gp1b platelet membrane protein and for fibrinogen. Activated platelets also release ADP and thromboxane A2, a product of arachidonic acid metabolism, which recruit additional platelets to the process. The platelet membrane protein complex GpIIb-IIIc binds to fibrinogen, thereby forming fibrinogen bridges between platelets, enhancing aggregation, and stabilizing the nascent thrombus. Activated platelets in turn release factors that initiate coagulation, thus forming a complex thrombus on the blood vessel wall. Thrombin itself stimulates further release of platelet granules and subsequent recruitment of new platelets.

Arterial Thrombosis

The coronary, cerebral, mesenteric, and renal arteries, and arteries of the lower extremities, are the blood vessels most commonly involved in an arterial thrombosis due to atherosclerosis. Arterial thrombosis may also occur, however, as a result of other disorders, including inflammation of arteries (arteritis), trauma, and blood diseases. Thrombi are also common in aneurysms (localized-dilations) of the aorta and its major branches, in which the distortion of blood flow, combined with intrinsic vascular disease, promotes thrombosis (Id. at 233). Stagnation of blood, as seen in other disorders such as atrial fibrillation, can also promote thrombus formation. In some cases, such thrombi can embolized as well.

Risk factors for thrombosis in the arterial system include, without limitation, immobilization after surgery or leg casting, obesity, advanced age, previous thrombosis, and cancer. The three factors that are commonly associated with development of thrombosis are: (1) damage to the endothelium, usually by atherosclerosis, which disturbs the anticoagulant properties of the blood vessel wall and serves as a site of origin for platelet aggregation and fibrin formation; (2) alteration in blood flow, whether from turbulence at the site of an aneurysm, sites of arterial bifurcation, or slowing of blood flow in narrowed arteries; and (3) increased coagulability of the blood.

Since most arterial thrombi occlude the blood vessel in which they occur, they often lead to ischemic necrosis of tissue supplied by that artery, i.e., an infarct. Infarction is the process by which coagulative necrosis develops in an area distal to the occlusion of an end-artery (Id. at 239). Thrombosis of a coronary or cerebral artery results in myocardial infarct (heart attack) or cerebral infarct (stroke), respectively (Id. at 234).

Myocardial infarcts can be transmural (through the entire wall) or subendocardial. While a transmural infarct results from complete occlusion of a major extramural coronary artery, a subendocardial infarction reflects prolonged ischemia caused by partially occluding lesions of the coronary arteries when the requirement for oxygen exceeds the supply (Id. at 241).

Thrombosis in the Heart

In a similar manner to the arterial system, thrombosis in the heart can develop on the endocardium. Endocardial injury and changes in blood flow in the heart may lead to a thrombus adhering to the underlying wall of the heart (mural thrombosis) (Id. at 234). Mural thrombosis may occur as a result of diseases such as myocardial infarction, atrial fibrillation, cardiomyopathy, and endocarditis. In myocardial infarction, adherent mural thrombi form in the left ventricular cavity over areas of myocardial infarction due to damaged endocardium and alterations in blood flow associated with a poorly functional or a dynamic segment of the myocardium. In atrial fibrillation, disordered atrial rhythm leads to slower blood flow and impaired left atrial contractility, which predisposes to formation of mural thrombi in atria. These are particularly prone to embolize, often to other arterial territories. In cardiomyopathy, primary myocardial diseases are associated with mural thrombi in the left ventricle, due to, e.g., endocardial injury and altered hemodynamics associated with poor myocardial contractility. In endocarditis, small thrombi may also develop on cardiac valves, usually mitral or aortic, that are damaged by a bacterial infection. Occasionally these small thrombi form in the absence of valve infections on a mitral or tricuspid valve (for example, injured by systemic lupus erythematosus, SLE). In chronic wasting states, large friable small thrombi may appear on cardiac valves, possibly reflecting a hypercoagulable state. A major complication of thrombosis in the heart occurs when fragments of the thrombus detach and become lodged in blood vessels at distant sites (embolization) (Id at 234).

Venous Thrombosis

Deep venous thrombosis, which occurs when a thrombus becomes lodged in one of the deep venous systems of the leg, often results from one or more of the same causative factors that favor arterial and cardiac thrombosis. Those factors are endothelial injury (e.g., trauma, surgery, childbirth), stasis (e.g., heart failure, chronic venous insufficiency, post-operative immobilization, prolonged bed rest) and a hypercoagulable state (e.g., oral contraceptives, late pregnancy, cancer, inherited thrombophilic disorders, advanced age, venous varicosities, phlebosclerosis) (Id. at 234-235).

Greater than 90% of venous thrombosis occur in deep veins of the legs, and have several potential fates. They may remain small and eventually become lysed, posing no further threat to health. Many become organized, whereby a small organization of venous thrombi may be incorporated into the blood vessel wall, and larger ones may undergo canalization, with partial restoration of venous drainage. Venous thrombi may also result in propagation, whereby they serve as a site of origination for further thrombosis and propagate proximally to involve the larger iliofemoral veins. Those venous thrombi that are large or those that have propagated proximally are a significant hazard to life, since they may dislodge and be carried to the lungs as pulmonary emboli (Id).

Thrombosis in the Brain

Thrombosis of a cerebral artery results in cerebral infarct, also referred to as a stroke. The most common type of cerebral infarct is the ischemic stroke, which may occur as a result of the blockage of an artery or vein (Gomes et al., Handbook of Clinical Nutrition and Stroke (2013) Chapter 2, page 17). Most arterial strokes are caused by emboli. The term "stroke in evolution" as used herein typically reflects a thrombus in the distal arteries arising from the carotid or basilar arteries, and describes the progression of neurologic symptoms while the patient is under observation. The term "completed stroke" as used herein refers to a stable neurologic deficit resulting from a cerebral infarct (Rubin's Pathology, Raphael Rubin and David S. Strayer, ed., 5th Ed., Lippincott Williams & Wilkins: 2008, page 1192).

The occlusion of different cerebral blood vessels results in diverse neurologic deficits caused by stroke. For example, occlusion or stenosis of an internal carotid artery affects the ipsilateral hemisphere, but this can be offset by the variable collateral circulation through the anterior and posterior communicating arteries. Most often, occlusion of a carotid artery produces infarcts restricted to all or some portion of the distribution of the middle cerebral artery. The consequences of occlusion of the various branches of the circle of Willis depend on the configuration of the circle. For example, occlusion at the trifurcation of the middle cerebral artery deprives the parietal cortex of circulation and produces motor and sensory deficits. When the dominant hemisphere is involved, these lesions are commonly accompanied by aphasia. An infarct of the lengthy and slender striate arteries, which originate from the proximal middle cerebral artery, often transects the internal capsule and produces hemiparesis or hemiplegia (Id.).

Infarction of the cerebral arteries may result from local ischemia or a generalized reduction in blood flow. The latter often results from systemic hypotension (e.g., shock), and produces infarction in the border zones between the distributions of the major cerebral arteries. If prolonged, severe hypotension can cause widespread brain necrosis. The occlusion of a single blood vessel in the brain (e.g., after an embolus comprises lodged) causes ischemia and necrosis in a well-defined area. The occlusion of a large artery produces a wide area of necrosis.

Cerebral Venous Sinus Thrombosis

The cerebral veins empty into large venous sinuses, the most prominent of which is the sagittal sinus which accommodates the venous drainage from the superior portions of the cerebral hemispheres. If a patient develops a blockage in a superficial or deep cerebral vein or venous sinus, hydrostatic pressure will increase upstream of the venous side of the capillary bed until ultimately water is forced through the capillary walls and into the interstitium of adjacent brain tissue reliant on the affected vein for normal fluid balance. This will eventually lead to hemorrhagic necrosis and vasogenic edema in the affected area. Venous sinus thrombosis in the brain is a potentially lethal complication of systemic dehydration, phlebitis, obstruction by a neoplasm, or sickle cell disease. Because venous obstruction causes stagnation upstream, abrupt thrombosis of the sagittal sinus results in bilateral hemorrhagic infarctions of the frontal lobe regions. A more indolent occlusion of the sinus (e.g., due to invasion by a meningioma) permits the recruitment of collateral circulation through the inferior sagittal sinus (Id. at 1194).

Fibrinolytic Agents

One method of treating a thrombosis is with a thrombolytic agent that breaks down the fibrinogen and fibrin comprising the thrombus. These fibrinolytic agents (also referred to as plasminogen activators) can be broadly classified into two groups: fibrin-specific agents; and non-fibrin specific agents. Fibrin-specific agents include drugs such as alteplase (tPA), reteplase (recombinant plasminogen activator; r-PA), and tenecteplase, which produce limited plasminogen conversion in the absence of fibrin (Ouriel K. A history of thrombolytic therapy. J Endovasc Ther. 2004 Dec. 11 Suppl 2:11128-133). Non-fibrin specific agents, including agents such as streptokinase, catalyze systemic fibrinolysis.

Fibrinolytic agents can be administered systemically or directly to the area of the thrombus. Treatment of acute myocardial infarction and acute ischemic stroke typically involves systemic delivery of the fibrinolytic agents (Hoffman R, Benz E J, Shattil S J, et al. Antithrombotic Drugs. In: Hematology: Basic Principles and Practice. 5th ed. Philadelphia, Pa.: Churchill Livingston Elsevier; 2008. chap 137).

Fibrinolytic agents can be used to treat several types of vascular obstruction conditions such as acute myocardial infarction, pulmonary embolism, deep vein thrombosis, acute ischemic stroke, and peripheral arterial disease. However, the use of fibrinolytic therapy comprises many drawbacks, including, without limitation, allergic reactions, embolism, stroke, and reperfusion arrhythmias, among others. One of the more serious complications is hemorrhage, such as intracranial hemorrhage (ICH) (See, Mehta R H, Cox M, Smith E, et al., Race/Ethnic differences in the risk of hemorrhagic complications among patients with ischemic stroke receiving thrombolytic therapy. Stroke. 2014 August 45 (8): 2263-9).

In addition, fibrinolytic agents have limited efficacy in certain conditions. For example, although tPA is an accepted treatment for treatment of acute ischemic stroke, the drug's ability to recanalize a blood vessel is poor in some cases. In proximal occlusions, for example, low recanalization rates are observed (8% recanalization in ICA occlusions), while in more distal occlusions higher rates of recanalization are observed (26% in M1 occlusions, 35% in M2 occlusions, and 40% in M3 occlusions) (Holodinsky, J. K. et al., Curr Neurol Neurosci Rep (2016) 16:42). Studies have shown that tPA is relatively ineffective for occlusions in the proximal anterior circulation, such as carotid T occlusions, carotid L occlusions, and M1/M2 occlusions of the MCA, which account for about one third of cases of acute ischemic stroke (Id.). Furthermore, the effectiveness of fibrinolytic agents, such as tPA, is dependent upon early administration. For example, a meta-analysis of several randomized trials of tPA administration after stroke onset revealed that a treatment delay of more than 4.5 hours resulted in no difference between tPA treatment and placebo treatment. This result may be due, in part, to a reduced chance of thrombus resolution as time passes and fibrin crosslinking occurs within the thrombus (Id.).

In some instances, fibrinolytic agents cannot be used at all. For example, the presence of active internal bleeding, recent intracranial or intraspinal trauma, a past or present bleeding disorder, uncontrolled hypertension, and pregnancy are all absolute contraindications of fibrinolytic agents.

Mechanical Endovascular Intervention

The current standard for therapeutic recanalization and reperfusion in many cases of vascular disease and acute stroke is to perform mechanical endovascular interventions via a percutaneous approach, often starting a catheter in the femoral artery at the groin, proceeding under x-ray guidance to the affected blood vessel.

Mechanical Endovascular Intervention in Coronary Artery Disease (CAD) Percutaneous Coronary Intervention (PCI)

Percutaneous coronary intervention (PCI) is a nonsurgical method for coronary artery revascularization. PCI methods include balloon angioplasty, coronary stenting, atherectomy (devices that ablate plaque), thrombectomy (devices that remove blockages from blood vessels) and embolic protection (devices that capture and remove embolic debris).

Balloon Angioplasty

Balloon angioplasty involves advancing a balloon-tipped catheter to an area of coronary narrowing, inflating the balloon, and then removing the catheter after deflation. Balloon angioplasty can reduce the severity of coronary stenosis, improve coronary flow, and diminish or eliminate objective and subjective manifestations of ischemia (Losordo D. W. et al. Circulation 1992 December 86 (6): 1845-58). The mechanism of balloon angioplasty action involves three events: plaque fracture, compression of the plaque, and stretching of the blood vessel wall. These lead to expansion of the external elastic lumina and axial plaque redistribution along the length of the blood vessel (Losordo D. W. et al. Circulation 1992 December 86 (6): 1845-58).

Coronary Stenting

Coronary stents are metallic scaffolds that are deployed within a diseased coronary artery segment to maintain wide luminal patency. They were devised as permanent endoluminal prostheses that could seal dissections, create a predictably large initial lumen, and prevent early recoil and late vascular remodeling (Krajcer Z. and Howell M. H. Tex Heart Inst J. 2000; 27 (4): 369-385).

Drug-eluting stents (DESs) elute medication to reduce restenosis (the recurrence of abnormal narrowing of a blood vessel) within the stents. Local release of rapamycin and its derivatives or of paclitaxel from a polymer matrix on the stent during the 30 days after implantation comprises been shown to reduce inflammation and smooth muscle cell proliferation within the stent, decreasing in-stent late loss of luminal diameter from the usual 1 mm to as little as 0.2 mm (Stone G. W. et al. N Engl J Med. 2007 Mar. 8. 356 (10): 998-1008). This dramatically lowers the restenosis rate after initial stent implantation or after secondary implantation of a DES for an in-stent restenosis (Stone G. W. et al. N Engl J Med. 2007 Mar. 8. 356 (10): 998-1008).

Coronary stents are used in about 90% of interventional procedures. Stent-assisted coronary intervention comprises replaced coronary artery bypass graft (CABG) as the most common revascularization procedure in patients with coronary artery disease (CAD) and is used in patients with multi-blood vessel disease and complex coronary anatomy (Kalyanasundaram A. et al. Medscape Dec. 16, 2014; article 164682; emedicine.medscape.com/article/164682-overview #a3).

Atherectomy

The directional coronary atherectomy (DCA) catheter was first used in human peripheral blood vessels in 1985 and in coronary arteries in 1986. In this procedure, a low-pressure positioning balloon presses a windowed steel housing against a lesion; any plaque that protrudes into the window is shaved from the lesion by a spinning cup-shaped cutter and trapped in the device's nose cone (Hinohara T. et al. Circulation 1990 March 81 (3 Suppl): IV79-91).

Rotational atherectomy uses a high-speed mechanical, rotational stainless-steel burr with a diamond chip-embedded surface. The burr is attached to a hollow flexible drive shaft that permits it to be advanced over a steerable guide wire with a platinum coil tip. The drive shaft is encased within a Teflon® sheath through which a flush solution is pumped to lubricate and cool the drive shaft and burr. A compressed air turbine rotates the drive shaft at 140,000-200,000 rpm during advancement across a lesion (Hinohara T. et al. Circulation 1990 March 81 (3 Suppl): IV79-91).

Laser Ablation

In laser ablation, an intense light beam travels via optical fibers within a catheter and enters the coronary lumen. After the target lesion is crossed with the guide wire, the laser catheter is advanced to the proximal end of the lesion. Blood and contrast medium are removed from the target blood vessel by flushing with saline before activating the laser (Kalyanasundaram A. et al. Medscape Dec. 16, 2014; article 164682; emedicine.medscape.com/article/164682-overview #a3).

Mechanical Thrombectomy

Intracoronary thrombi may be treated with mechanical thrombectomy devices. These include rheolytic, suction and ultrasonic thrombectomy devices.

In rheolytic thrombectomy, high-speed water jets create suction via the Bernoulli-Venturi effect. The jets exit orifices near the catheter tip and spray back into the mouth of the catheter, creating a low-pressure region and intense suction. This suction pulls surrounding blood, thrombus, and saline into the tip opening and propels particles proximally through the catheter lumen and out of the body (Kalyanasundaram A. et al. Medscape Dec. 16, 2014; article 164682; emedicine.medscape.com/article/164682-overview #a3).

The catheters used for suction thrombectomy act via manual aspiration. These catheters are advanced over a wire to the intracoronary thrombus then passed through the thrombus while suction is applied to a hole in the catheter tip. Large intact thrombus fragments can be removed by means of this technique (Kalyanasundaram A. et al. Medscape Dec. 16, 2014; article 164682; emedicine.medscape.com/article/164682-overview #a3).

Ultrasonic thrombectomy involves the use of ultrasonic vibration to induce cavitation that can fragment a thrombus into smaller components (Choi S. W. et al. J. Intery Cardiol. 2006 Feb. 19 (1): 87-92).

Embolization Protection

Embolization (the passage of an embolus, blood clot, or other such blockage within the blood stream) can be caused by the manipulation of guidewires, balloons, and stents across complex atherosclerotic carotid artery lesions (Krajcer Z. and Howell M. H. Tex Heart Inst J. 2000; 27 (4): 369-385). Several devices have been developed to trap such embolic material and remove it from the circulation.

The PercuSurge Guardwire is a device that consists of a 0.014- or 0.018-inch angioplasty guidewire constructed of a hollow nitinol hypotube. Incorporated into the distal wire segment is an inflatable balloon capable of occluding blood vessel flow. The proximal end of the wire incorporates a Microseal™ that allows inflation and deflation of the distal occlusion balloon. When the Microseal adapter is detached, the occlusion balloon remains inflated, at which time angioplasty and stenting are performed. An aspiration catheter can be advanced over the wire into the blood vessel, and manual suction is applied to retrieve particulate debris (Krajcer Z. and Howell M. H. Tex Heart The Medicorp device consists of a protection balloon and a dilation balloon that can be used over a 0.014-inch coronary guidewire. Occlusion above the lesion and below the lesion creates a dilation zone without a flow, which is aspirated and cleared of atherosclerotic debris (Krajcer Z. and Howell M. H. Tex Heart Inst J. 2000; 27 (4): 369-385). Various distal filters have been deployed as well.

Endovascular Treatment of Abdominal Aortic Aneurysms (AAA)

Two endoluminal AAA exclusion stent graft systems have received FDA approval: (i) the Ancure™ Endograft System (Guidant/EVT; Menlo Park, Calif.); and (ii) the AneuRx™ device (Medtronic AVE; Santa Rosa, Calif.) (Krajcer Z. and Howell M. H. Tex Heart Inst J. 2000; 27 (4): 369-385). Both are over-the-wire systems that require bilateral femoral artery access.

The Ancure™ stent graft is an unsupported, single piece of woven Dacron® fabric. The graft is bifurcated and comprises no intra-graft junctions. The main device is delivered through a 24-Fr introducer sheath; a 12-Fr sheath is required to facilitate the deployment of the contralateral iliac limb. The graft is attached via a series of hooks that are located at the proximal aortic end and at both iliac ends. The hooks are seated transmurally (passing through the blood vessel wall) in the aorta and the iliac arteries, initially by minimal radial force, and then affixed by low-pressure balloon dilation. Radiopaque markers are located on the body of the graft for correct alignment and positioning (Krajcer Z. and Howell M. H. Tex Heart Inst J. 2000; 27 (4): 369-385).

The AneuRx™ device is a modular 2-piece system composed of a main bifurcation segment and a contralateral iliac limb. The graft is made of thin-walled woven polyester that is fully supported by a self-expanding nitinol exoskeleton. Attachment is accomplished by radial force at the attachment sites, which causes a frictional seal. The main bifurcated body is delivered through a 21-Fr sheath, and the contralateral limb requires a 16-Fr sheath. The body of the graft comprises radiopaque markers that facilitate correct alignment and positioning (Krajcer Z. and Howell M. H. Tex Heart Inst J. 2000; 27 (4): 369-385).

Mechanical Endovascular Neurointervention

Mechanical Thrombectomy

Mechanical thrombectomy (e.g., the excision of a clot or other such blockage from a blood vessel) uses a treatment device to remove a blockage from the target blood vessel by a catheter. Subgroups include: (1) suction thrombectomy devices that remove occlusions from the cerebral blood vessels by aspiration (Proximal Thrombectomy) and (2) removal devices that physically seize cerebral thrombi and drag them out of the cerebral blood vessels (Distal Thrombectomy) (Gralla J. et al. Stroke 2006; 37:3019-24; Brekenfeld C. et al. Stroke 2008; 39:1213-9).

Proximal Endovascular Thrombectomy

Manual suction thrombectomy is performed by moving forward an aspiration catheter at the proximal surface of the thrombus (Singh P. et al. J Neurosci Rural Pract. 2013 July-September; 4 (3): 298-303). Manual aspiration is then carried out and the aspiration catheter is taken back under continuous negative pressure. The Penumbra System™ (Penumbra, Almeda, Calif. USA), a variation of the manual proximal aspiration method, comprises a dedicated reperfusion catheter attached to a pumping system applying constant aspiration. A second retriever device is similar to a stent and is utilized to take out the resistant blockage (Singh P. et al. J Neurosci Rural Pract. 2013 July-September; 4 (3): 298-303). The time window for neuroradiological intervention is 8 hours after stroke onset in patients not eligible for intravenous thrombolysis or in patients where intravenous thrombolysis was unsuccessful (Singh P. et al. J Neurosci Rural Pract. 2013 July-September; 4 (3): 298-303).

The Penumbra System™ comprises been examined in a number of clinical trials. The Penumbra Pivotal Stroke Trial was a prospective, single-arm, multicenter study that recruited 125 stroke patients (mean NIHSS 18) within 8 hours of symptom onset and was successful in 81.6% of treated blood vessels (Penumbra Pivotal Stroke Trial Investigators: The Penumbra pivotal stroke trial: Safety and effectiveness of a new generation of mechanical devices for blockage removal in intracranial large blood vessel occlusive disease. Stroke 2009; 40:2761-8). However, a good clinical outcome at 90 days was attained in only 25% of patients and in 29% of patients with successful recanalization (the process of restoring flow to or reuniting an interrupted channel such as a blood vessel) of the target blood vessel (Penumbra Pivotal Stroke Trial Investigators: The penumbra pivotal stroke trial: Safety and effectiveness of a new generation of mechanical devices for blockage removal in intracranial large blood vessel occlusive disease. Stroke. 2009; 40:2761-8). Poor clinical results occurred despite comparatively better recanalization rates as evidenced by a mortality rate of 32.8% and the occurrence of symptomatic intracerebral hemorrhage (ICH) in 11.2% (Penumbra Pivotal Stroke Trial Investigators: The penumbra pivotal stroke trial: Safety and effectiveness of a new generation of mechanical devices for blockage removal in intracranial large blood vessel occlusive disease. Stroke. 2009; 40:2761-8).

Distal Endovascular Thrombectomy

Distal thrombectomy is a technically difficult procedure (Singh P. et al. J Neurosci Rural Pract. 2013 July-September; 4 (3): 298-303). A number of clinical studies have been carried out using the MERCI (Mechanical Embolus Removal in Cerebral Ischemia) Retriever® device (Concentric Medical, Mountain View, USA), which was the earliest distal thrombectomy device approved by the United States Food and Drug Administration (FDA) (Singh P. et al. J Neurosci Rural Pract. 2013 July-September; 4 (3): 298-303). In the initial stage of the procedure, the occlusion site must be traversed with a microcatheter so as to deploy the device beyond the thrombus. The MERCI Retriever® device is pulled back into the thrombus and positioned within the blockage. Next, the MERCI Retriever® and the trapped blockage are withdrawn, initially into the positioning catheter and then out of the patient's body (Singh P. et al. J Neurosci Rural Pract. 2013 July-September; 4 (3): 298-303). Proximal balloon occlusion by means of a balloon guide catheter and aspiration during retrieval of the Merci device is done for the majority of cases in order to prevent thromboembolic complications (Nogueira R. G. et al. Am J Neuroradiol. 2009; 30:649-61; Nogueira R. G. et al. Am J Neuroradiol. 2009; 30:859-7). During in vivo experimental studies, the distal technique was shown to be more efficient than proximal manual aspiration (Gralla J. et al. Stroke 2006; 37:3019-24).

The MERCI Retriever® clinical trial was a 25-site, uncontrolled, technical efficacy trial (Smith W. S. et al. Stroke 2005; 36:1432-8). The trial incorporated 151 patients with occlusion of the internal carotid artery or vertebral and basilar arteries, who did not qualify for intra-arterial therapy (LAT) within 8 hours of symptom onset (Smith W. S. et al. Stroke 2005; 36:1432-8). Successful recanalization was accomplished in 46%, with excellent clinical outcome in 27.7% of patients (Smith W. S. et al. Stroke 2005; 36:1432-8). Successful recanalization was linked with distinctly better clinical outcomes. Average procedure time was 2.1 hours, with clinically noteworthy procedural complications occurring in 7.1% and a rate of symptomatic intracranial hemorrhage (ICH) occurring in 7.8% of patients (Smith W. S. et al. Stroke 2005; 36:1432-8). Despite good clinical outcome, limitations of this device include operator learning curve, the need to traverse the occluded artery to deploy the device distal to the occlusion, the duration required to perform multiple passes with the device, blockage fragmentation and passage of an embolus within the bloodstream (Meyers P. M. et al. Circulation 2011; 123:2591-2601).

Self-Expanding Stents

Until recently, intracranial stenting was restricted to off-label use of balloon-mounted stents intended for cardiac circulation (Singh P. et al. J Neurosci Rural Pract. 2013 July-September; 4 (3): 298-303). These stents are not ideal for treating intracranial disease due to their rigidity which makes navigation in the convoluted intracranial blood vessels difficult (Singh P. et al. J Neurosci Rural Pract. 2013 July-September; 4 (3): 298-303). Self-expanding intracranial stents permit stenting in acute stroke that is unmanageable with conventional treatment regimens. The blockage occluding the blood vessel is outwardly displaced by the side of the blood vessel wall and becomes trapped in the interstices of a self-expanding stent (SES). Wingspan™ (Stryker), Neuroform® (Stryker, Kalamazoo, Mich.), and Cordis Enterprise™ (Cordis Neurovascular, Fremont, Calif.) self-expanding stenting systems have improved steering, cause a reduced amount of vasospasm, and cause a reduced amount of side-branch occlusions as compared to balloon-inflated stents (Singh P. et al. J Neurosci Rural Pract. 2013 July-September; 4 (3): 298-303). Drawbacks of this method include delayed in-stent thrombosis, the use of platelet inhibitors which may cause intracerebral hemorrhage (ICH) and perforator occlusion from relocation of the thrombus after stent placement (Samaniego E. A. et al Front Neurol. 2011; 2:1-7; Fitzsimmons B. F. et al. Am J Neuroradiol. 2006; 27:1132-4; Levy E. I. et al. Neurosurgery 2006; 58:458-63; Zaidat O. O. et al. Stroke 2008; 39:2392-5).

Retrievable Thrombectomy Stents

Retrievable thrombectomy stents are self-expandable, re-sheathable, and re-constrainable stent-like thrombectomy devices which combine the advantages of intracranial stent deployment with immediate reperfusion and subsequent retrieval with definitive blockage removal from the occluded artery (Singh P. et al. J Neurosci Rural Pract. 2013 July-September; 4 (3): 298-303). Removal of the device circumvents the drawbacks associated with permanent stent implantation. These include the requirement for double anti-platelet medication, which potentially adds to the risk of hemorrhagic complications, and the risk of in-stent thrombosis or stenosis. The application of retrievable thrombectomy stents is analogous to that of intracranial stents. Under general anesthesia, using a transfemoral approach, a guide catheter is positioned in the proximal internal carotid artery. A guide wire is advanced coaxially over a microcatheter within the blocked intracranial blood vessel and navigated past the thrombus. The microcatheter is then advanced over the wire through the blockage, and the guide wire is substituted for the embolectomy device (Id.). The revascularization device is placed with the middle third of the device residing within the thrombus formation. The radial force of the stent retriever is able to create a channel by squeezing the thrombus and is able to partially restore blood flow to the distal territory in the majority of cases, producing a channel for a temporary bypass (Id). The device is usually left in place for an embedding time of up to 10 minutes, permitting entrapment of the thrombus within the stent struts. To extract the thrombus, the unfolded stent and the microcatheter are slowly dragged into the guide catheter with flow reversal by continuous aspiration with a 50-ml syringe from the guide catheter (Id.). The designs of these stents differ in terms of radial strength, design of the proximal and distal stent aperture, stent cell design, material and supplementary intraluminal struts (Mordasini P. et al. Am J Neuroradiol 2011; 32:294-300; Brekenfeld C. et al. Am J Neuroradiol. 201; 2:1269-73; Mordasini P. et al. Am J Neuroradiol. 2013; 34:153-8).

Blood Vessels Used for Mechanical Intervention Femoral Artery

The femoral artery is the main artery that provides oxygenated blood to the tissues of the leg. It passes through the deep tissues of the femoral (or thigh) region of the leg parallel to the femur.

The common femoral artery is the largest artery found in the femoral (thigh) region of the body. It begins as a continuation of the external iliac artery at the inguinal ligament which serves as the dividing line between the pelvis and the leg. From the inguinal ligament, the femoral artery follows the medial side of the head and neck of the femur inferiorly and laterally before splitting into the deep femoral artery and the superficial femoral artery.

The superficial femoral artery flexes to follow the femur inferiorly and medially. At its distal end, it flexes again and descends posterior to the femur before forming the popliteal artery of the posterior knee and continuing on into the lower leg and foot. Several smaller arteries branch off from the superficial femoral artery to provide blood to the skin and superficial muscles of the thigh.

The deep femoral artery follows the same path as the superficial branch, but follows a deeper path through the tissues of the thigh, closer to the femur. It branches off into the lateral and medial circumflex arteries and the perforating arteries that wrap around the femur and deliver blood to the femur and deep muscles of the thigh. Unlike the superficial femoral artery, none of the branches of the deep femoral artery continue into the lower leg or foot.

Like most blood vessels, the femoral artery is made of several distinct tissue layers that help it to deliver blood to the tissues of the leg. The innermost layer, known as the endothelium or tunica intima, is made of thin, simple squamous epithelium that holds the blood inside the hollow lumen of the blood vessel and prevents platelets from sticking to the surface and forming one or more blockages. Surrounding the tunica intima is a thicker middle layer of connective tissues known as the tunica media. The tunica media contains many elastic and collagen fibers that give the femoral artery its strength and elasticity to withstand the force of blood pressure inside the blood vessel. Visceral muscle in the tunica media may contract or relax to help regulate the amount of blood flow. Finally, the tunica externa is the outermost layer of the femoral artery that contains many collagen fibers to reinforce the artery and anchor it to the surrounding tissues so that it remains stationary.

The femoral artery is classified as an elastic artery, meaning that it contains many elastic fibers that allow it to stretch in response to blood pressure. Every contraction of the heart causes a sudden increase in the blood pressure in the femoral artery, and the artery wall expands to accommodate the blood. This property allows the femoral artery to be used to detect a person's pulse through the skin (See, e.g., The Cardiovascular System at a Glance, 4th Edition, Philip I. Aaronson, Jeremy P. T. Ward, Michelle J. Connolly, November 2012, @ 2012, Wiley-Blackwell, Hoboken, N.J.).

Use of the Femoral Artery for Endovascular Procedures

Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort (Alvarez-Tostado J. A. et al. Journal of Vascular Surgery 2009; 49 (2): 378-385). Femoral puncture also allows access to virtually all of the arterial territories and affords favorable ergonomics for the operator in most instances (Alvarez-Tostado J. A. et al. Journal of Vascular Surgery 2009; 49 (2): 378-385).

Brachial Artery

The brachial artery is a major blood vessel located in the upper arm and is the main supplier of blood to the arm and hand. It continues from the axillary artery at the shoulder and travels down the underside of the arm. Along with the medial cubital vein and bicep tendon, it forms the cubital fossa, a triangular pit on the inside of the elbow. Below the cubital fossa, the brachial artery divides into two arteries running down the forearm: the ulnar and the radial; the two main branches of the brachial artery. Other branches of the brachial artery include the inferior ulnar collateral, profunda brachii, and superior ulnar arteries (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N.J.). The radial artery has recently become a common access route for percutaneous endovascular procedures as well.

Use of the Brachial Artery for Endovascular Procedures

Brachial artery access is a critical component of complex endovascular procedures, especially in instances where femoral access is difficult or contraindicated, such as the absence of palpable femoral pulses, severe common femoral occlusive disease, recent femoral intervention or surgery or femoral aneurysms/pseudoaneurysms. It is a straightforward procedure with a high success rate for percutaneous cannulation (Alvarez-Tostado J. A. et al. Journal of Vascular Surgery 2009; 49 (2): 378-385). However, there is a general reluctance to puncture the right brachial artery due to the need to navigate through the innominate artery and arch and due to the risk for complications such as direct nerve trauma and ischemic occlusion resulting in long-term disability (Alvarez-Tostado J. A. et al. Journal of Vascular Surgery 2009; 49 (2): 378-385; Cousins T. R. and O'Donnell J. M. AANA Journal 2004; 72 (4): 267-271).

Need for New Endovascular Thrombectomy Devices

Mechanical endovascular neuro interventions are the current standard for the treatment of acute stroke. Several independent clinical trials have, however, identified significantly different clinical outcomes in patients when treated with different endovascular techniques and thrombectomy devices (Papanagiotou, P., and White, C. J., Endovascular Reperfusion Strategies for Acute Stroke, JACC: Cardiovascular Interventions, 2016, Vol. 9, No. 4, pg. 307). For example, stent retriever devices generally have been identified as providing higher recanalization rates with a reduced recanalization time and lower complication rates when compared to first generation mechanical recanalization devices such as the Merci device and the Penumbra aspiration system (Id. at 315).

Despite the potential to diminish procedure time and to improve recanalization rates, drawbacks to using these devices remain. For example, the TREVO 2 study (Thrombectomy Revascularisation of Large Blood Vessel Occlusions in AIS) was an open label, multi-center trial evaluating the efficacy of the Trevo Pro retriever (Stryker Neurovascular, Fremont, USA) with the Merci device in patients with large blood vessel ischemic stroke (Nogueira R. G. et al. Lancet 2012; 380:1231-40). Symptomatic intracranial hemorrhage (ICH) occurred in 6.8% in the Trevo group and in 8.9% of the Merci group, with mortality rates of 33% and 24% respectively. The outcome of this trial suggests that there are unique mechanical mechanisms of action and consequently dissimilar success and efficacy rates depending on the thrombectomy approaches applied (Singh P. et al. J Neurosci Rural Pract. 2013 July-September; 4 (3): 298-303).

Furthermore, some blood vessel occlusions are resistant to recanalization by a particular thrombectomy device due to the characteristics of the thrombus (e.g. a "hard" thrombus) and the particular blood vessel where the occlusion is located (Papanagiotou, P., and White, C. J., Endovascular Reperfusion Strategies for Acute Stroke, JACC: Cardiovascular Interventions, 2016, Vol. 9, No. 4, pg. 315).

Thus, at present, there does not appear to be a universally superior mechanical thrombectomy device that provides sufficient aspiration force without obstructing aspiration, is manageable in terms of size and flexibility, and is quick/easy to remove while preventing emboli from going to end organs. There thus remains a need for mechanical thrombectomy devices and strategies. The present disclosure addresses this unmet need.

Glossary

Anatomical Terms

When referring to animals that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "ablation" as used herein, refers to a procedure that uses radiofrequency energy (e.g., microwave heat) to destroy a small area of heart tissue that is causing rapid and irregular heartbeats. Destroying this tissue restores the heart's regular rhythm. The procedure is also called radiofrequency ablation.

The terms "acute angle" and "acute angulation" are used interchangeably herein to refer to a sharp, obstructive or abnormal angle or bend (e.g., less than 90 degrees) in an organ, artery, blood vessel, etc.

The terms "anomaly", "variation", "abnormality" and "aberration" are used interchangeably herein to refer to a deviation from what is standard, normal or expected. For example, "bovine arch variation" is an anatomical deviation from the most common aortic arch branching pattern in humans. By way of additional example, an anomaly can occur in a blood vessel having tortuosity.

The term "aneurysm", as used herein, refers to a localized widening (dilatation) of an artery, a vein, or the heart. At the point of an aneurysm, there is typically a bulge, where the wall of the blood vessel or organ is weakened and may rupture.

Blood flow in most aneurysms is regular and predictable primarily according to the geometric relationship between the aneurysm and its parent artery. As blood flows within the parent artery with an aneurysm, divergence of blood flow, as occurs at the inlet of the aneurysm, leads to dynamic disturbances, producing increased lateral pressure and retrograde vortices that are easily converted to turbulence. Blood flow proceeds from the parent blood vessel into the aneurysm at the distal or downstream extent of the aneurysm neck (i.e., the transition from the sac to the parent artery), circulates around the periphery along the aneurysm wall from the neck to the top of the fundus (i.e., aneurysm sac) (downstream to upstream), returning in a type of "isotropic shower" along the aneurysm wall toward the neck region, and exits the closest extent of the aneurysm neck into the parent blood vessel (See, e.g., Strother C. M. Neuroradiology 1994; 36:530-536; Moulder P. V. Physiology and biomechanics of aneurysms. In: Kerstein M D, Moulder P V, Webb W R, eds. Aneurysms. Baltimore, Md.: Williams & Wilkins; 1983:20).

As flow persists, areas of stagnation or vortices develop within a central zone of the aneurysm. These rotating vortices, formed at the entrance to the aneurysm at each systole (i.e., ventricle contraction) and then circulated around the aneurysm, are caused by the slipstreams or regions of recirculating flow rolling upon themselves when they enter the aneurysm at its downstream wall during systole. The stagnant vortex zone occurs in the center and at the fundus or upper portion of the aneurysm and becomes more pronounced in larger aneurysms. It is this stagnant zone that is believed to promote the formation of a blockage (e.g., a thrombus, a blood clot, etc.), particularly in giant aneurysms (See, e.g., Gobin Y. P. et al. Neuroradiology 1994; 36:530536; Hademenos G. J. and Massoud T. F. Stroke 1997; 28:2067-2077).

The term "abdominal aortic aneurysm" or "AAA", as used herein refers to an aortic diameter at least one and one-half times the normal diameter at the level of the renal arteries, which is approximately 2.0 cm. Generally, a segment of abdominal aorta with a diameter of greater than 3.0 cm is considered an aortic aneurysm. Aortic aneurysms constitute the 14th leading cause of death in the United States. Risk factors associated with AAA include age, sex, ethnicity, smoking, hypertension and atherosclerosis, among others (See, e.g., Aggarwal S. et al. Exp Clin Cardiol. 2011; 16 (1): 11-15; Ouriel K. et al. J Vasc Surg. 1992; 15:12-18; Silverberg E. et al. C A Cancer J Clin. 1990; 40:9-26).

The term "arteriovenous malformation" ("AVM"), as used herein, refers to a tangle of abnormal and poorly formed blood vessels (e.g., arteries and veins) which have a higher than normal rate of bleeding compared to normal blood vessels.

AVMs are congenital vascular lesions that occur as a result of capillary mal-development between the arterial and venous systems. Approximately 0.14% of the United States population has an intracranial AVM that poses a significant risk and represents a major life threat, particularly to persons under the age of 50 years. The blood vessels constituting the AVM are weak and enlarged and serve as direct shunts for blood flow between the high-pressure arterial system and the low-pressure venous system, corresponding to a large pressure gradient and small vascular resistance. The abnormal low-resistance, high-flow shunting of blood within the brain AVM without an intervening capillary bed causes the fragile dilated blood vessels in the nidus (i.e., tangle of blood vessels) to become structurally abnormal and fatigued, to further enlarge, and to rupture (See, e.g., Wilkins R. H. Neurosurgery 1985; 16:421-430; Graves V. B. et al. Invest Radiol. 1990; 25:952-960; Hademenos G. J. et al., Neurosurgery 1996; 38:1005-1015).

The abnormal micro-blood vessels of an AVM serve as passive conduits for blood flow from the arterial circulation directly to the venous circulation, by-passing their normal physiological function of brain tissue perfusion. The hemodynamic consequences of an AVM occur as a result of two interdependent circulatory mechanisms involved in the shunting of blood between artery and vein (See, e.g., Hademenos G. J. and Massoud T. F. Stroke 1996; 27:10721083).

In the normal cerebral circulation, blood flows under a high cerebrovascular resistance and high cerebral perfusion pressure. However, the presence of a brain AVM in the normal circulation introduces a second abnormal circuit of cerebral blood flow where the blood flow is continuously shunted under a high perfusion pressure through the AVM, possessing a low cerebrovascular resistance and low venous pressure. The clinical consequence of the abnormal shunt is a significant increase in blood returning to the heart (approximately 4 to 5 times the original amount, depending on the diameter and size of the shunt), resulting in a dangerous overload of the heart and cardiac failure. Volumetric blood flow through an AVM ranges from 200 mL/min to 800 mL/min and increases according to nidus size (See, e.g., Yamada S. Neurol Res. 1993; 15:379-383).

The abnormal shunting of blood flow by brain AVMs rapidly removes or "steals" blood from the normal cerebral circulation and substantially reduces the volume of blood reaching the surrounding normal brain tissue. This phenomenon, known as cerebrovascular steal, depends on the size of the AVM and is the most plausible explanation for the development of progressive neurological deficits. Cerebrovascular steal could translate into additional neurological complications developed as a result of cerebral ischemia or stroke in neuronal territories adjacent to an AVM (See, e.g., Manchola I. F. et al. Neurosurgery 1993; 33:556-562; Hademenos G. J. and Massoud T. F. Stroke 1997; 28:2067-2077).

The term "atherectomy", as used herein, refers to a minimally invasive endovascular surgery technique for removing atherosclerosis from blood vessels within the body by cutting plaque from the walls of a blood vessel.

The term "atherosclerosis" (also known as "hardening of the arteries"), as used herein, refers to a pathological process in which calcified lipid or fatty deposits from flowing blood accumulate along the innermost intimal layer of a blood vessel wall. Atherosclerotic plaques are found almost exclusively at the outer wall of one or both daughter blood vessels at major arterial bifurcations, including the carotid. Atherosclerosis and the development of arterial plaques are the products of a host of independent biochemical processes including the oxidation of low-density lipoproteins, formation of fatty streaks, and the proliferation of smooth muscle cells. As the plaques form, the walls become thick, fibrotic, and calcified. As a result, the lumen narrows, reducing the flow of blood to the tissues supplied by the artery (See, e.g., Hademenos G. J. and Massoud T. F. Stroke 1997; 28:2067-2077; Hademenos G. J. Am Scientist 1997; 85:226-235; Woolf N., Davies M. J. Sci Am Science & Medicine 1994; 1:38-47).

Atherosclerotic deposits promote the development of blockages or the process of thrombosis, due in part, to flow obstruction and to high shear stresses exerted on the blood vessel wall by the blood. High wall shear stress mechanically damages the inner wall of the artery, initiating a lesion. Low wall shear stress encourages the deposition of particles on the artery wall, promoting the accumulation of plaque. Turbulence has also been implicated in atherosclerotic disease because it can increase the kinetic energy deposited in the blood vessel walls and because it can lead to areas of stasis, or stagnant blood flow, that promote clotting. The presence of atherosclerotic lesions introduces an irregular blood vessel surface, resulting in turbulent blood flow, thus causing the dislodgment of plaques of varying size into the bloodstream. Subsequently, the dislodged plaque lodges into a blood vessel of smaller size, preventing further passage of blood flow (See, e.g., Hademenos G. J. and Massoud T. F. Stroke 1997; 28:20672077).

The term "atresia", as used herein, refers to the absence or abnormal narrowing of an opening or passage in the body. For example, aortic atresia refers to a rare congenital anomaly in which the aortic orifice is absent or closed.

The term "atrial fibrillation", as used herein, refers to an irregular and often fast heart rate which may cause symptoms such as heart palpitations, fatigue, and shortness of breath. Atrial fibrillation weakens the cardiac wall and introduces abnormalities in the physiological function of the heartbeat, which ultimately result in reduced systemic pressure, conditions of ischemia and stroke.

The term "brachiocephalic trunk", also known as "innominate artery", as used herein, refers to a major blood vessel that supplies the head, neck and right arm. It is the first of three main branches of the aortic arch, which originates from the upward convexity. After arising in the midline, it courses upwards to the right, crossing the trachea, and bifurcates posteriorly to the right sternoclavicular joint into the right subclavian and right common carotid arteries. It typically measures 4-5 cm in length with a diameter of approximately 12 mm.

The term "brain aneurysm", as used herein, refers to a cerebrovascular disease that manifests as a pouching or ballooning of the blood vessel wall (i.e., vascular dilation). The vascular dilatation develops at a diseased site along the arterial wall into a distended sac of stressed and thinned arterial tissue. The fully developed cerebral aneurysm typically ranges in size from a few millimeters to 15 mm but can attain sizes greater than 2.5 cm. If left untreated, the aneurysm may continue to expand until it ruptures, causing hemorrhage, severe neurological complications and deficits, and possibly death (Hademenos G. J. and Massoud T. F. Stroke 1997; 28:2067-2077; Hademenos G. J. Phys Today 1995; 48:24-30).

The two main treatment options for a patient suffering from a brain aneurysm are (i) surgical clipping; and (ii) endovascular coiling. Surgical clipping is an intracranial procedure in which a small metallic clip is placed along the neck of the aneurysm. The clip prevents blood from entering into the aneurysm sac so that it no longer poses a risk for bleeding. The clip remains in place, causing the aneurysm to shrink and permanently scar. Endovascular coiling is a minimally invasive technique in which a catheter is inserted into the femoral artery and navigated through the blood vessels to the blood vessels of the brain and into the aneurysm. Coils are then packed into the aneurysm to the point where it arises from the blood vessel, thus preventing blood flow from entering the aneurysm. Additional devices, such as a stent or balloon, for example, may be needed to keep the coils in place.

The term "branch", as used herein, refers to something that extends from or enters into a main body or source; a division or offshoot from a main stem (e.g., blood vessels); one of the primary divisions of a blood vessel.

The term "coarctation" or "coarctation of the aorta", as used herein, refers to a congenital narrowing of a short section of the aorta.

The terms "compound curves" and "multi-curves" are used interchangeably herein to refer to multiple deflection points along the length of a catheter. By way of example, two deflection points allow a catheter to be deflected into an "S" shape or the shape of a shepherd's hook.

The term "curve diameter", as used herein, refers to the furthest distance a catheter moves from its straight axis as it is being deflected. The curve diameter does not always remain constant during deflection and does not necessarily indicate the location of the catheter tip.

The term "deflection", as used herein, refers to movement of a catheter tip independent of the rest of the catheter.

The term "dyscrasia", as used herein, refers to an abnormal or disordered state of the body or a bodily part. The term "blood dyscrasia", as used herein, refers to an abnormally of blood cells or of clotting elements.

The term "embolus" (plural "emboli"), as used herein, refers to a gaseous or particulate matter that acts as a traveling blockage (e.g., a clot). A common example of an embolus is a platelet aggregate dislodged from an atherosclerotic lesion. The dislodged platelet aggregate is transported by the bloodstream through the cerebro-vasculature until it reaches a blood vessel too small for further propagation. The blockage remains there, clogging the blood vessel and preventing blood flow from entering the distal vasculature. Emboli can originate from distant sources such as the heart, lungs, and peripheral circulation, which could eventually travel within the cerebral blood vessels, obstructing flow and causing stroke. Other sources of emboli include atrial fibrillation and valvular disease. The severity of stroke depends on the size of the embolus and the location of the obstruction. The bigger the embolus and the larger the blood vessel obstruction, the larger the territory of brain at risk (Hademenos G. J. and Massoud T. F. Stroke 1997; 28:2067-2077).

The term "endoluminal", as used herein, refers to the state of being within a tubular organ or structure (e.g., blood vessel, duct, gastrointestinal tract, etc.) or within a lumen. The term "lumen", as used herein, refers to the inner open space or cavity of a tubular structure.

The term "French" (abbreviated "Fr" or "F" or "Fg" or "Ga" or "CH" or "Ch"), as used herein, is a system used to measure the diameter of a catheter. The French unit of measure is equivalent to three times the diameter in millimeters (mm). For example, 9 Fr is equivalent to a diameter of 3 mm.

The term "hemorrhage", as used herein, refers to the escape of blood from a ruptured blood vessel.

Blood vessels are typically structurally adept to withstand the dynamic quantities required to maintain circulatory function. For reasons that are not entirely understood, the blood vessel wall can become fatigued and abnormally weak and possibly rupture. With blood vessel rupture, hemorrhage occurs with blood seeping into the surrounding brain tissue. As the blood accumulates within the brain, the displaced volume causes the blood, now thrombosed, to ultimately compress the surrounding blood vessels. The compression of blood vessels translates into a reduced blood vessel diameter and a corresponding reduction in flow to surrounding tissue, thereby enlarging the insult (See, e.g., Hademenos G. J. and Massoud T. F. Stroke 1997; 28:2067-2077).

In the brain, hemorrhage may occur at the brain surface (extraparenchymal), for example, from the rupture of congenital aneurysms at the circle of Willis, causing subarachnoid hemorrhage (SAH). Hemorrhage also may be intraparenchymal, for example, from rupture of blood vessels damaged by long-standing hypertension, and may cause a blockage (e.g., a blood clot, an intracerebral hematoma, etc.) within the cerebral hemispheres, in the brain stem, or in the cerebellum. Hemorrhage may be accompanied by ischemia or infarction. The mass effect of an intracerebral hematoma may compromise the blood supply of adjacent brain tissue; or SAH may cause reactive vasospasm of cerebral surface blood vessels, leading to further ischemic brain damage. Infarcted tissue may also become secondarily hemorrhagic. Among the vascular lesions that can lead to hemorrhagic strokes are aneurysms and arteriovenous malformations (AVMs) (See, e.g., Hademenos G. J. and Massoud T. F. Stroke 1997; 28:2067-2077).

The term "hypoplasia", as used herein, refers to a condition of arrested development in which an organ or other part of the body remains below the normal size or in an immature state, usually due to a deficiency in the number of cells; atrophy due to destruction of some of the elements and not merely to their general reduction in size.

The term "introducer", as used herein, refers to an instrument such as a tube or a sheath or other such engagement member that is placed within a vein or artery for introduction of a flexible device, for example, a catheter, needle, wire, etc.

The terms "ischemic" and "ischemia", as used herein, refer to deficient supply of blood to a body part generally due to obstruction of the inflow of arterial blood (e.g., by the narrowing of arteries, spasm or disease).

The term "kickback", as used herein refers to the phenomenon of catheter coil prolapse (slipping forward or down) due to a counterforce against the catheter by the prolapsed coil tail. The counterforce may be due to a lack of available space to insert the last coil. This lack of space may be the result of, for example, a blood vessel variation such as a bovine arch variation, a vertebral artery variation, a thrombus, an embolus, an arteriovenous malformation and the like.

The term "myocardial infarction", as used herein, refers to death of cells of an area of heart muscle as a result of oxygen deprivation, which in turn is caused by obstruction of the blood supply; commonly referred to as a "heart attack". The most common cause is thrombosis of an atherosclerotic coronary artery or a spasm. Less common causes included coronary artery abnormalities and vasculitis (inflammation of blood vessels).

The term "recanalization", as used herein, refers to the process of restoring flow to or reuniting an interrupted channel of a bodily tube (e.g., a blood vessel).

The term "reperfusion", as used herein, refers to restoration of the flow of blood to a previously ischemic organ or tissue (e.g., heart or brain).

The term "restenosis", as used herein, refers to the recurrence of abnormal narrowing of a blood vessel (e.g., artery or vein) or valve.

The term "slant height" of a cone, as used herein, refers to the length measured along a lateral face from the base to the apex along the "center" of the face. For example, the slant height "l" of a right circular cone is the distance from the apex to a point on the base, and is related to the height "h" and base radius "a" by the equation: $l=\sqrt{(h^2+a^2)}$.

The term "stenosis" as used herein refers to an abnormal narrowing of a passage in the body. The term "restenosis", as used herein, refers to the recurrence of this abnormal narrowing (e.g., of a blood vessel (e.g., artery or vein) or valve).

The term "steerability", as used herein, refers to an ability to turn or rotate the distal end of a catheter with like-for-like movement of the proximal section or the catheter handle.

The terms "subject" or "individual" or "patient" are used interchangeably to refer to a member of an animal species of mammalian origin, including but not limited to, mouse, rat, cat, goat, sheep, horse, hamster, ferret, pig, dog, guinea pig, rabbit and a primate, such as, for example, a monkey, ape, or human.

The phrase "subject in need thereof" as used herein refers to a patient that (i) will be treated with a device according to the principles of the present disclosure, (ii) is receiving treatment with a device according to the principles of the present disclosure; or (iii) comprises received treatment with a device according to the principles of the present disclosure, unless the context and usage of the phrase indicates otherwise.

The term "stroke", "acute stroke" or "cerebrovascular accident", as used herein, refers to neurological signs and symptoms, usually focal and acute, which result from diseases involving blood vessels of the brain. Generally, strokes are either occlusive (due to closure of a blood vessel) or hemorrhagic (due to bleeding from a blood vessel). Although most occlusive strokes are due to atherosclerosis and thrombosis, and most hemorrhagic strokes are associated with hypertension or aneurysms, strokes of either type may occur at any age from many causes, including cardiac disease, trauma, infection, neoplasm, blood dyscrasia, vascular malformation, immunological disorder, and exogenous toxins. An ischemia stroke results from a lack of blood supply and oxygen to the brain that occurs when reduced perfusion pressure distal to an abnormal narrowing (stenosis) of a blood vessel is not compensated by autoregulatory dilation of the resistance vessels. When ischemia is sufficiently severe and prolonged, neurons and other cellular elements die. This condition is referred to as "cerebral infarction" (See, e.g., Hart R. G. et al., Stroke 1990; 21:1111-1121). Although the consequences of both ischemic and hemorrhagic stroke are similar (i.e., blood vessel obstruction, resultant reduced blood flow to the brain, neurological deficits and possibly death), the biophysical and hemodynamic mechanisms behind the obstruction of blood flow are different. Biophysical mechanisms for the development of obstructions that ultimately lead to stroke can arise by six distinct processes: atherosclerosis, embolus, thrombus, reduced systemic pressure, hemorrhage, and vasospasm (See, e.g., Hademenos G. J. and Massoud T. F., Stroke 1997; 28:2067-2077).

The term "taper", as used herein, refers to a reduction of thickness toward one end; the gradual diminution of width or thickness in an elongated object; i.e., to become slenderer toward one end.

The term "thrombectomy", as used herein, refers to the surgical excision of a thrombus. The term "thrombus", as used herein, refers to an internal physiological mechanism responsible for the clotting of blood. A thrombus is an aggregation of platelets and fibrin formed in response either to an atherosclerotic lesion or to blood vessel injury. In response to blood vessel or tissue injury, the blood coagulation system is activated, which initiates a cascade of processes, transforming prothrombin, ultimately resulting in a fibrin blockage (Prothrombin→Thrombin→Fibrinogen-→Fibrin→Fibrin Blockage) (See, e.g., Hademenos G. J. and Massoud T. F. Stroke 1997; 28:2067-2077).

Although a host of mechanisms and causes are responsible for blood vessel injury, blood vessel injury can occur as a result of forces (e.g., shear stresses) coupled with excess energy created by the turbulent flow exerted against the inner (intimal) lining of the blood vessel wall, particularly an atherosclerotic blood vessel wall (See, e.g., Fry D. L. Circ Res. 1968; 22:165-197; Stein P. D. and Sabbah H. N. Circ Res. 1974; 35:608-614; Mustard J. F. et al. Am J Med. 1962; 33:621-647; Goldsmith H. L. et al. Thromb Haemost 1986; 55:415-435).

The term "tortuosity" and other grammatical forms of the term "tortuous" is used herein to refer to a property of a tube, passage or blood vessel (e.g., an artery or a vein) being twisted, crooked or having many turns.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vasospasm", as used herein, refers to the sudden constriction of a blood vessel, reducing its diameter and flow rate. When bleeding occurs in the subarachnoid space, the arteries in the subarachnoid space can become spastic with a muscular contraction, which can produce a focal constriction of sufficient severity to cause total occlusion. The length of time that the blood vessel is contracted during vasospasm varies from hours to days. However, regardless of the duration of blood vessel constriction, reduction of blood flow induces cerebral ischemia, thought to be reversible within the first 6 hours and irreversible thereafter. It comprises been shown that vasospasm is maximal between 5 and 10 days after subarachnoid hemorrhage and can occur up to 2 weeks after subarachnoid hemorrhage (See, e.g., Wilkins R. H. Contemp Neurosurg. 1988; 10:1-66; Hademenos G. J. and Massoud T. F. Stroke 1997; 28:2067-2077).

The term "venous thrombosis", as used herein, refers to a thrombus that forms within a vein. A common form of venous thrombosis is deep vein thrombosis, in which the thrombus can break off, flow toward the lungs, and become a pulmonary embolism.

Although a host of mechanisms and causes are responsible for blood vessel injury, blood vessel injury can occur as a result of forces (e.g., shear stresses) coupled with excess energy created by the turbulent flow exerted against the inner (intimal) lining of the blood vessel wall, particularly an atherosclerotic blood vessel wall (See, e.g., Fry D. L. Circ Res. 1968; 22:165-197; Stein P. D. and Sabbah H. N. Circ Res. 1974; 35:608-614; Mustard J. F. et al. Am J Med. 1962; 33:621-647; Goldsmith H. L. et al. Thromb Haemost 1986; 55:415-435).

SUMMARY OF THE INVENTION

The present disclosure describes various methods and devices, which may be used individually or in combination with each other. More specifically, the present disclosure describes a (first) device (e.g., a macerating thrombectomy device) that is configured for simultaneous rotation, irrigation, aspiration and a component for capturing and removing emboli and debris, which may include a (second) device that is configured as a temporary bypass catheter, which may include an optional balloon, as described herein below.

In one embodiment, the present disclosure describes a device that is configured to (simultaneously) rotate, irrigate, aspirate, and macerate. It provides a safe and reliable means of applying a simultaneous combination of irrigation, aspiration and maceration to a thrombus or other such blockage, obstruction, or vascular abnormality.

In one embodiment, the present disclosure describes a device that is configured to capture and removing emboli and debris released during the delivery of a replacement cardiac valve with a semi-permeable membrane, while allowing flow of blood through the membrane, and simultaneously providing a channel for delivery of the valve through the filter via a single vascular access point.

In various embodiments, the devices described herein are configured to achieve certain improvements and advancements including, for example: simultaneously providing (combining) irrigation, aspiration, and maceration; simultaneously providing (combining) irrigation and aspiration to reverse flow, independent of maceration; simultaneously providing (combining) irrigation and aspiration to reverse flow, independent of maceration, and retrieving blockages by removing the bulk of the blockage, and the induced flow reversal by the combination of simultaneous irrigation and aspiration to facilitate the removal of any debris (e.g., fragments of the blockage that break free via the aspiration) rather than embolizing distally (which may cause permanent tissue ischemia); using a balloon mounted aspiration catheter, designed to use at the face of an arterial thrombus, to occlude a blood vessel and facilitate flow reversal via aspiration and simultaneous distal irrigation; using a filter-tip aspiration catheter, for use in most venous and dialysis av graft cases involving the removal of a blockage, as well as during valve delivery and other trans-aortic cardiac procedures; utilizing an IVUS (intravenous ultrasound) (in combination with one or more of the devices described herein) to monitor flow and debris buildup at the tip of the catheter (particularly the preferred embodiment of the present disclosure, at the catheter tip in the filter-tip aspiration catheter version); incorporating and utilizing a vibrational wire (particularly in combination with the aspiration catheter, balloon mounted, and/or filter-tip aspiration catheter) to agitate, break up, macerate, or otherwise fragment the blockage to avoid the aspirating catheter becoming clogged with large debris; and using the sinusoidal hypo-tube embodiment of the present disclosure (described herein below) to achieve an eggbeater like-maceration effect, while simultaneously irrigating into and beyond the blockage and aspirating to remove the blockage. It is envisioned that the vibrational wire described herein may be used (combined) with any embodiment of the presently disclosed aspiration catheter (which may include on optional balloon).

The present disclosure's filter-tip aspirator catheter can also be used in select cases of peripheral arterial thrombectomies. The prerequisite in such cases is the ability to access the artery downstream from a blockage. This is usually not possible for arterial emboli in the brain, but may be possible for arteries in arms and legs. A non-limiting example is an axillary artery embolus/thrombus, where a person of ordinary skill can obtain access proximal to the blockage from femoral access, and/or a person of ordinary skill can also access distally (downstream) via a brachial or radial artery approach.

In certain embodiments, the medical devices described herein may include (provide for) a combination of features (e.g., irrigation, aspiration and maceration) for the purpose of safely and effectively performing thrombectomy (e.g., the removal of blood clots, thrombi, and other such blockages). It is envisioned that the devices described herein may include one or more switches to start a pump for irrigation, a vacuum for aspiration, and/or a rotational element for rotational maceration. Alternatively, when used in an interventional suite or other environment which already has a "power injector" that can inject irrigation, it is envisioned that the presently disclosed device(s) may include a remote-control element, an on-off switch, or a flow-regulator to allow existing irrigation devices to be activated and deactivated simultaneously with the aspiration and maceration elements of the present disclosure and/or to further control flow from various devices and systems. Additionally, it is envisioned that the devices described herein may optionally be equipped to allow sequential/stepwise activation of the irrigation, aspiration, and maceration features, in various orders.

The devices described herein (and the corresponding methods of use) overcome the medical difficulties often associated with blood vessel collapse during a blockage removal procedure. More particularly, the present disclosure contemplates the introduction of fluid(s) (e.g., a saline solution) to a target blockage during treatment (e.g., the maceration and/or removal of a clot) to maintain pressure inside the obstructed blood vessel and allow for aspiration to induce flow.

In various embodiments of the disclosure, it is envisioned that a blockage may be treated (e.g., removed) from a target blood vessel by using existing access locations (e.g., from an adjacent or otherwise suitable blood vessel) to inhibit patient impact. To facilitate such treatment, in certain embodiments, the devices described herein are configured to mechanically reduce the size of a blockage (e.g., a thrombus or an atheroma) to allow for removal of the blockage using existing access locations. To inhibit (if not entirely prevent) migration of the blockage (and/or any debris created during treatment), and/or remove any excess fluid from the target blood vessel, the devices described herein may also be configured to apply aspiration. Additionally, is envisioned that the devices described herein may be configured to replace the mass being removed with an alternate material (e.g., saline solution), thereby supporting the target blood vessel during treatment to inhibit (if not entirely prevent) collapse that may otherwise occur as a result of blockage removal. It is thus envisioned that the devices described herein may be configured to simultaneously irrigate, aspirate, and macerate (e.g., cut or otherwise treat blockages). In some cases, cooling fluid, neuro-protectants, tissue-protectants, anti-oxidants, oxygen delivery fluids, and/or blood may be delivered as well (e.g., to further prevent tissue ischemia and/or permanent tissue injury until appropriate flow can be restored).

The present disclosure also describes the use of an additional (e.g., second) medical device, such as a vessel bypass catheter, further details of which are provided below, that offers various improvements over conventional catheters in the treatment of a patient's blood vessel system.

Devices according to the present disclosure incorporate a variety of structures and features including, for example, a temporary bypass catheter, a temporary bypass balloon, a temporary bypass balloon mounted catheter, a single-lumen access support catheter, rotating components, irrigating components, and aspirating components. During use, the devices described herein may be deployed within a patient's vasculature to address a blockage (e.g., a clot or other such obstruction) in an artery or a vein that may be causing ischemia, heart strain, or other such difficulty relating to the lack of blood flow.

The devices described herein are configured for positioning such that the blockage is located between a side hole in the device and an end hole in the device. Once positioned, a bypass element, also described herein, will allow for the temporary bypass of blood flow.

In order to prevent the backflow of blood (e.g., proximally of the side hole), it is envisioned that the catheters described herein may include a valve or a smaller proximal diameter and/or that the device be attached to a pressurized fluid line.

Additionally, it is envisioned that the catheter may include one or more additional lumens. For example, in addition to the main (operative) lumen, the catheter may include a secondary lumen and/or tertiary lumen (in any of the aforedescribed configurations) that is configured to deliver fluid into a balloon (e.g., in the context of the aforementioned bypass balloon) and/or to deliver fluid into the blockage between the side hole and the end hole. Such an arraignment facilitates the delivery of lytics or other such medications into the blockage while there is an effective temporary bypass of flow through the catheter, which allows time for the directly applied medication to treat (e.g., break up and/or dissolve) the blockage while avoiding ischemic tissue injury. In those embodiments incorporating an inflatable balloon, in addition to the main (operative) lumen, the catheter may include a secondary lumen that is configured to deliver fluid into the balloon and a tertiary lumen that is configured to deliver fluid (e.g., medication) into the blockage. In certain embodiments, it is also envisioned that an additional outer catheter may be employed, with or without a balloon mounted on the outer catheter.

Devices according to the present disclose may also include one or more side loops that are configured to macerate a blockage upon rotation of the device. Aspiration can also be applied to the catheter (e.g., via the side hole and/or an end hole). In certain embodiments, is envisioned that the side hole may be covered (e.g., via withdrawal of the device into a sheath, via closure of an actively closed valve, etc.) such that aspiration occurs exclusively through the end hole.

In certain embodiments, the present disclosure describes a device (e.g., a catheter) that includes a complex shape (e.g., a sinusoidal configuration) such that rotation of the catheter itself results in the maceration of a blockage.

Additionally, it is envisioned that the devices described herein may include an additional, optional balloon (e.g., on a body of the device, on the aforedescribed sheath, or in any other suitable location) such that, upon inflation, the balloon arrests flow and/or reverses flow during the maceration to inhibit (if not entirely prevent) the downstream migration of debris (clots).

In addition to the aspects, features, and advantages described above, the devices described herein can facilitate the rapid restoration of temporary blood flow through a blockage to avoid ischemic injury and the immediate restoration of a blood flow (either partially or entirely) to tissue beyond the blockage, which creates additional time to remove and/or dissolve the blockage. Additionally, in the context of pulmonary emboli, the devices and methods described herein reduce strain on the patient's heart that may otherwise occur as a result of reduced outflow from the right side of the heart. More specifically, the temporary bypass catheters described herein mitigate (if not entirely prevent) such strain by allowing outflow from the right heart beyond the blockage when pulmonary emboli are present in the main pulmonary arteries.

In another aspect of the present disclosure, an endovascular device is disclosed that is configured for insertion into a patient's blood vessel. The endovascular device includes: a first member with a filter element that is reconfigurable between a collapsed (e.g., closed) configuration and an expanded (e.g., open) configuration to capture emboli within the patient's blood vessel; a second member with a retainer that is configured to maintain the filter element in the collapsed configuration; and an engagement member that is configured for engagement with the second member. The second member is longitudinally movable in relation to the first member such that engagement between the engagement member and the second member moves the retainer longitudinally in relation to the filter element to facilitate deployment of the filter element from the retainer and reconfiguration of the filter element from the collapsed configuration into the expanded configuration within the patient's blood vessel.

In certain embodiments, the filter element may be configured for automatic expansion upon deployment from the retainer.

In certain embodiments, the filter element may include a proximal end that is directly attached to a distal end of the first member and a free distal end.

In certain embodiments, the first member, the second member, and the engagement member may be configured for independent movement.

In certain embodiments, the engagement member may be removable.

In certain embodiments the second member and the engagement member may be combined as an outer catheter (sheath).

In certain embodiments, the filter element may include a funnel-shaped configuration upon reconfiguration into the expanded configuration.

In certain embodiments, one end of the filter element may be attached circumferentially about the distal end hole of the first member such that the filter element defines a minimum transverse cross-sectional dimension (e.g., a diameter) adjacent to the distal end hole and progressively flares outwardly so as to define a maximum transverse cross-sectional dimension (e.g., a diameter) at an opposite end thereof.

In certain embodiments, the endovascular device may further include a removable cover that is positioned about the filter element to constrain the filter element and maintain the collapsed configuration thereof.

In certain embodiments, the endovascular device may define an outer transverse dimension allowing for insertion of the endovascular device into the patient's inferior vena cava.

In certain embodiments, at least one of the first member and/or the second member may include at least one steerable segment (zone) to facilitate reconfiguration thereof. For example, in certain embodiments, the first member and the second member may each include at least one steerable segment (zone) to facilitate reconfiguration thereof.

In certain embodiments, the filter element may include an asymmetrical configuration. For example, in certain embodiments, the filter element may include a first portion that defines a first longitudinal length and a second portion that defines a second longitudinal length greater than the first longitudinal length.

In another aspect of the present disclosure, an endovascular device is disclosed that includes: an outer catheter configured for insertion into a blood vessel; a treatment device that is insertable through the outer catheter and configured to facilitate the removal of a blockage within the blood vessel to increase blood flow; and a filter element that is configured for deployment within the blood vessel through the treatment device. The filter element is reconfigurable between a collapsed configuration, in which the filter element is movable longitudinally through the lumen of the treatment device, and an expanded configuration, in which the filter element is configured to capture emboli within the blood vessel.

In another aspect of the present disclosure, an endovascular device is disclosed that includes: an inner catheter with a semi-permeable filter attached circumferentially to a distal end thereof that is configured for insertion into a blood vessel; an outer catheter (sheath); and a treatment device configured for insertion through the inner catheter and the filter to facilitate the removal of a blockage within the blood vessel to increase blood flow.

In certain embodiments, the filter element may be reconfigurable between a collapsed configuration, in which the filter element is movable longitudinally through a lumen of the outer catheter, and an expanded configuration, in which the filter element is configured to capture emboli within the blood vessel.

In certain embodiments the filter element may expand automatically when released from a constraint provided by the outer catheter.

In another aspect of the present disclosure, an endovascular device is disclosed that includes: an inner catheter with a semi-permeable filter attached circumferentially to a distal end thereof and configured for insertion into a blood vessel; an outer catheter (sheath); and a treatment device configured for insertion through the inner catheter and the filter element to deliver a replacement valve.

In certain embodiments, the endovascular device may include the replacement valve as well.

In certain embodiments, the filter element may be reconfigurable between a collapsed configuration, in which the filter element is movable longitudinally through a lumen of the outer catheter, and an expanded configuration, in which the filter element is configured to capture emboli within the blood vessel.

In certain embodiments, the filter element may be configured for automatic expansion when released from a constraint provided by the outer catheter.

In certain embodiments, at least one segment of the outer catheter and/or the inner catheter may be steerable.

It is envisioned that each embodiment of the disclosure may be configured for delivery into the body as a single unit. Alternatively, it is envisioned that each embodiment of the disclosure may be configured for delivery into the body in a step-wise fashion in which separate components at are inserted as separate points in time.

In certain embodiments, it is envisioned that the endovascular device may further include a secondary (additional) inner catheter the extends beyond the outer catheter and/or the filter element to aid in delivery over a wire through skin, soft tissue, and/or a vessel wall. It is envisioned that the secondary inner catheter may include increased stiffness (e.g., compared to the outer catheter and/or the (primary)

inner catheter) such that the secondary inner catheter functions as (or in a fashion similar to) a dilator.

In certain embodiments, the treatment device may include a retrieval mechanism to facilitate extraction of the blockage from the blood vessel.

In certain embodiments, the retrieval mechanism may be configured to apply aspiration to the blood vessel.

In certain embodiments, the retrieval mechanism may be configured for direct contact with the blockage such that the blockage is withdrawn from the blood vessel upon retraction of the treatment device.

In certain embodiments, the treatment device may include at least one macerating member that is configured to agitate the blockage upon rotation of the treatment device.

In certain embodiments, the treatment device may include at least one side hole that is configured to communicate fluid therethrough to facilitate irrigation of the blood vessel during treatment of the blockage.

In certain embodiments, the at least one macerating member may be generally aligned with the at least one side hole.

In certain embodiments, the outer catheter may be configured to apply aspiration to the blood vessel to facilitate removal of debris created during agitation of the blockage. For example, it is envisioned that the outer catheter may be configured to apply aspiration to the blood vessel either intermittently or continuously.

In certain embodiments, the inner catheter may be configured to apply aspiration to the blood vessel to facilitate the removal of debris created during agitation of the blockage. For example, it is envisioned that the inner catheter may be configured to apply aspiration to the blood vessel either intermittently or continuously.

In another aspect of the present disclosure, a method of performing an endovascular procedure on a patient is disclosed that includes: advancing an outer member through the patient's descending aorta, across the patient's aortic arch, and beyond the patient's innominate artery; causing relative longitudinal movement between the outer member and an inner member located within the outer member to deploy and expand a filter element supported by the inner member to capture emboli; and delivering a replacement valve into the patient's heart while filtering emboli through the filter element.

In certain embodiments, delivering the replacement valve may include delivering the replacement valve through the outer member.

In certain embodiments, delivering the replacement valve may include delivering the replacement valve through the filter element.

In certain embodiments, delivering the replacement valve may include delivering the replacement valve through a delivery member separate from the outer member.

In certain embodiments, the method may include advancing one or more of a lithotripsy device, a balloon, an ablation catheter, a diagnostic device, or a therapeutic device through the filter.

In certain embodiments, advancing the outer member may include advancing the outer member in a first direction and delivering the replacement valve through the delivery member may include advancing the delivery member in a second direction generally opposite to the first direction.

In certain embodiments, outer member and the delivery member in the same direction.

In certain embodiments, deploying and expanding the filter element may include locating the filter element between the patient's innominate artery and the patient's aortic valve to protect the patient's innominate artery, the patient's left common carotid artery, the patient's left subclavian artery, and the patient's descending aorta.

In certain embodiments, deploying and expanding the filter element may include automatically expanding the filter element upon exposure from the outer member and conforming the filter element to the patient's ascending aorta so blood flowing through the patient's ascending aorta travels through the filter element.

In certain embodiments, delivering the replacement valve into the patient's heart may include placing the replacement valve within an existing valve.

In certain embodiments, delivering the replacement valve into the patient's heart may include placing the replacement valve within a damaged anatomical valve naturally occurring within the patient or within an artificial valve (e.g., within an existing replacement valve).

In certain embodiments, the method may further include retrieving an existing valve from the patient (e.g., a damaged anatomical valve naturally occurring within the patient or an artificial valve).

In certain embodiments the method may further comprise collapsing the filter element to facilitate removal from the patient.

In certain embodiments, collapsing the filter element may include withdrawing the inner member and the filter element into the outer member.

In certain embodiments, collapsing the filter element may include advancing the outer member distally over the inner member and the filter element.

In certain embodiments, collapsing the filter element may include withdrawing the inner member and the filter element into the outer member and advancing the outer member distally over the inner member and the filter element.

These and other advantages of the present disclosure will be apparent to those of ordinary skill in the art by reference to the following detailed description and the accompanying drawings.

In another aspect of the present disclosure, an endovascular device is disclosed that is configured for insertion into a patient's blood vessel. The endovascular device includes a first member with a semi-permeable filter element that is reconfigurable between a collapsed configuration and an expanded configuration to capture emboli within the patient's blood vessel; a second member with a retainer that is configured to maintain the filter element in the collapsed configuration; and an engagement member. The second member is longitudinally movable in relation to the first member, and the engagement member is configured for engagement with the second member to move the retainer longitudinally in relation to the filter element to facilitate deployment of the filter element from the retainer and reconfiguration of the filter element from the collapsed configuration into the expanded configuration within the patient's blood vessel.

In certain embodiments, the filter element may be configured for automatic expansion into a funnel-shaped configuration upon deployment from the retainer.

In certain embodiments, the endovascular device may further include a removable cover that is positioned about the filter element to constrain the filter element and maintain the collapsed configuration thereof.

In certain embodiments, the second member and the engagement member may be unitarily formed such that the second member and the engagement member are configured as an outer sheath through which the first member and the filter element may be inserted and removed.

In certain embodiments, the first member may include an inner lumen that is configured to receive one or more additional (medical) devices.

In certain embodiments, at least one of the first member and the second member may include at least one steerable segment to facilitate reconfiguration thereof.

In certain embodiments, the filter element may include a first portion that defines a first longitudinal length and a second portion that defines a second longitudinal length greater than the first longitudinal length such that the filter element is asymmetrical in configuration.

In another aspect of the present disclosure, an endovascular device is disclosed that includes: a catheter that is configured for insertion into a blood vessel; a treatment device that is insertable through the catheter and configured to facilitate the removal of a blockage within the blood vessel to increase blood flow; and a filter element that is supported by the catheter and configured for deployment within the blood vessel. The filter element is reconfigurable between a collapsed configuration, in which the filter element is movable longitudinally through the catheter, and an expanded configuration, in which the filter element is configured to capture emboli within the blood vessel.

In certain embodiments, the treatment device may include a retrieval mechanism to facilitate extraction of the blockage from the blood vessel.

In certain embodiments, the retrieval mechanism may be configured to apply aspiration to the blood vessel.

In certain embodiments, the retrieval mechanism may be configured for direct contact with the blockage such that the blockage is withdrawn from the blood vessel upon retraction of the treatment device.

In certain embodiments, the treatment device may include at least one macerating member that is configured to agitate the blockage upon rotation of the treatment device.

In certain embodiments, the treatment device may include at least one side hole that is configured to communicate fluid therethrough to facilitate irrigation of the blood vessel during treatment of the blockage.

In certain embodiments, the catheter may be configured to apply aspiration to the blood vessel to facilitate the removal of debris created during agitation of the blockage.

In certain embodiments, the catheter may include an inner catheter and an outer catheter.

In certain embodiments, the filter element may be supported on the inner catheter.

In certain embodiments, the filter element may be non-removably supported by the catheter (e.g., such that the filter element is fixedly connected to (supported by) the catheter).

In certain embodiments, the filter element may include a semi-permeable configuration.

In certain embodiments, the filter element may include a funnel-shaped configuration upon expansion.

In certain embodiments, the filter element may be supported adjacent to an end hole of the catheter.

In another aspect of the present disclosure, a method of performing an endovascular procedure on a patient is disclosed that includes: advancing an outer member through the patient's aorta, across the patient's aortic arch, and beyond the patient's innominate artery; causing relative longitudinal movement between the outer member and an inner member located within the outer member to deploy and expand a filter element supported by the inner member to capture emboli; and delivering a replacement valve into the patient's heart while filtering emboli through the filter element.

In certain embodiments, delivering the replacement valve may include delivering the replacement valve through the inner member.

In certain embodiments, delivering the replacement valve may include delivering the replacement valve through the filter element.

In certain embodiments, delivering the replacement valve may include delivering the replacement valve through a delivery member separate from the outer member.

In certain embodiments, advancing the outer member may include advancing the outer member in a first direction and delivering the replacement valve through the delivery member may include advancing the delivery member in a second direction that is generally opposite to the first direction.

In certain embodiments, deploying and expanding the filter element may include locating the filter element between the patient's innominate artery and the patient's aortic valve to protect the patient's innominate artery, the patient's left common carotid artery, the patient's left subclavian artery, and the patient's aorta.

In certain embodiments, delivering the replacement valve into the patient's heart may include placing the replacement valve within an existing valve.

In certain embodiments, delivering the replacement valve into the patient's heart may include placing the replacement valve within a damaged anatomical valve naturally occurring within the patient.

In certain embodiments, the method may further include retrieving an existing valve from the patient.

In certain embodiments, the method may further include collapsing the filter element to facilitate removal of the filter element from the patient by withdrawing the inner member and the filter element into the outer member. Additionally, or alternatively, in certain embodiments, collapsing the filter element may include advancing the outer member distally over the inner member and the filter element.

In certain embodiments, expanding the filter element may include expanding a semi-permeable member that is positioned about a distal end hole of the inner member into a funnel-shaped configuration such that an outer rim of the filter element (substantially) contacts an inner wall of the patient's aorta.

In certain embodiments, the method may further include performing a lithotripsy procedure prior to delivering the replacement valve.

BRIEF DESCRIPTION OF THE DRAWINGS

FIG. 6 shows an illustration of a side view of one embodiment of the endovascular device (system) of the present disclosure.

FIG. 6A shows an illustration of a side view of one embodiment of the endovascular device (system) of the present disclosure.

FIG. 7A shows an illustration of a side view of one embodiment of the endovascular device (system) of the present disclosure.

FIG. 7B shows an illustration of a side view of one embodiment of the endovascular device (system) of the present disclosure.

FIG. 7C shows an illustration of a perspective view of one embodiment of the endovascular device (system) of the present disclosure.

FIG. 7D shows an illustration of a cross section view of one embodiment of the endovascular device (system) of the present disclosure.

FIG. 7E shows an illustration of a cross section view of one embodiment of the endovascular device (system) of the present disclosure.

FIG. 7F shows an illustration of a side view of one embodiment of the endovascular device (system) of the present disclosure.

FIG. 7G shows an illustration of a side view of one embodiment of the endovascular device (system) of the present disclosure.

FIG. 7H shows an illustration of a side view of one embodiment of the endovascular device (system) of the present disclosure.

FIG. 7I shows an illustration of a side view of one embodiment of the endovascular device (system) of the present disclosure.

FIG. 7J shows an illustration of a cross section view of one embodiment of the endovascular device (system) of the present disclosure.

FIG. 8 show a cross-sectional view of one embodiment of the endovascular device (system) of the present disclosure.

FIGS. 8A and 8B show cross-sectional views of another embodiment of the endovascular device (system) of the present disclosure.

FIG. 11A shows a cross section side view of one embodiment of the endovascular device (system) of the present disclosure.

FIG. 11B shows a cross section side view of one embodiment of the endovascular device (system) of the present disclosure.

FIG. 12B shows a cross section side view of one embodiment of the endovascular device (system) of the present disclosure.

FIG. 13A shows a cross section side view of one embodiment of the endovascular device (system) of the present disclosure.

FIG. 13B shows a cross section side view of one embodiment of the endovascular device (system) of the present disclosure.

FIG. 14 shows a cross section side view of one embodiment of a balloon disposed upon the simultaneous aspirating, irrigating, macerating device/system (e.g., microcatheter) of the present disclosure, further depicting reversal of blood flow distal to the balloon mounted aspiration catheter.

FIG. 22 is a schematic representation of one embodiment of the endovascular device (system) of the present disclosure shown in a first (initial, normal) configuration.

FIG. 23 is a transverse cross-sectional view of the medical device seen in FIG. 22 taken along line 23-23.

In the various views of the drawings, like reference characters designate like or similar parts.

DETAILED DESCRIPTION OF THE INVENTION

Figure 1:
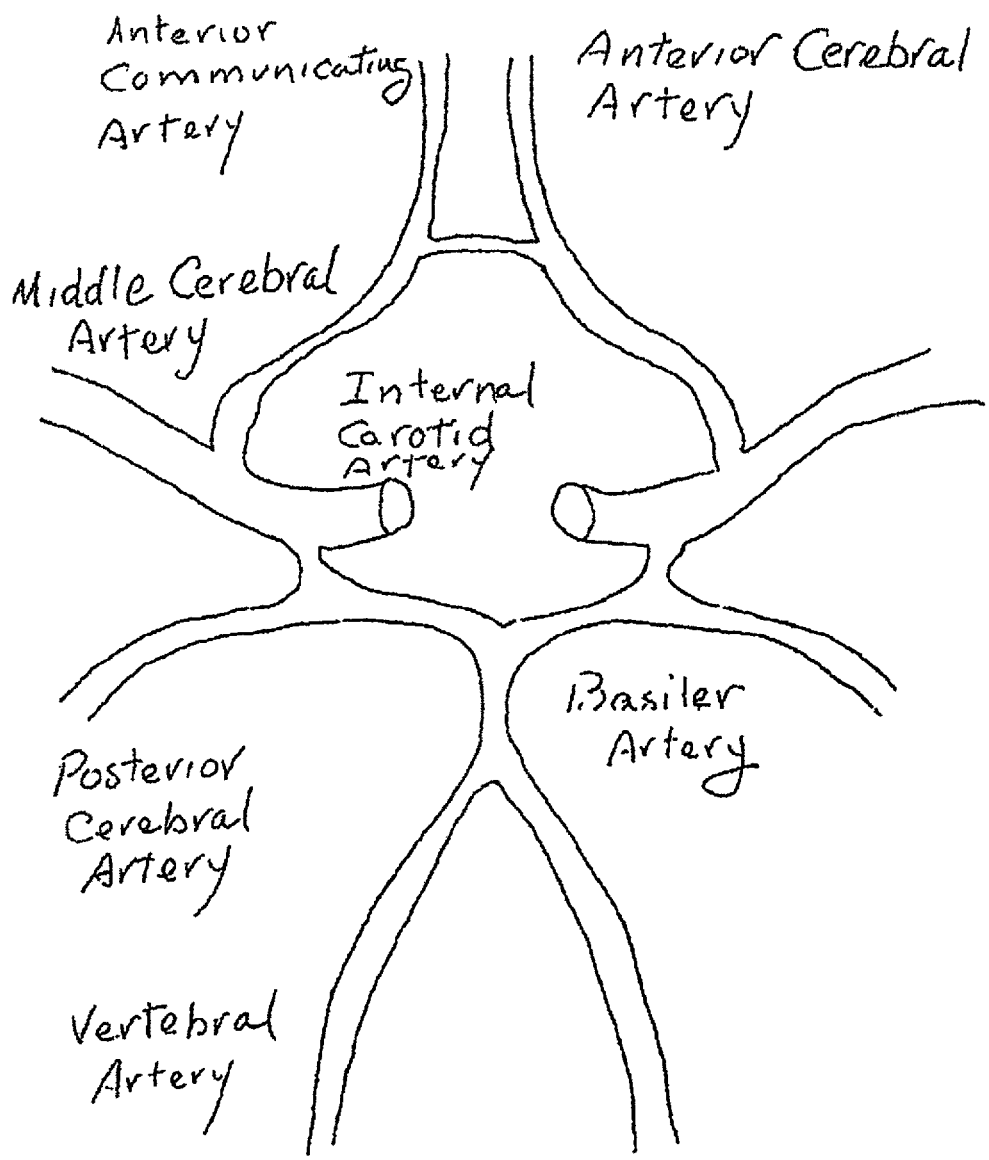
FIG. 1 shows an illustrative view of the cerebral arteries.
Figure 2:
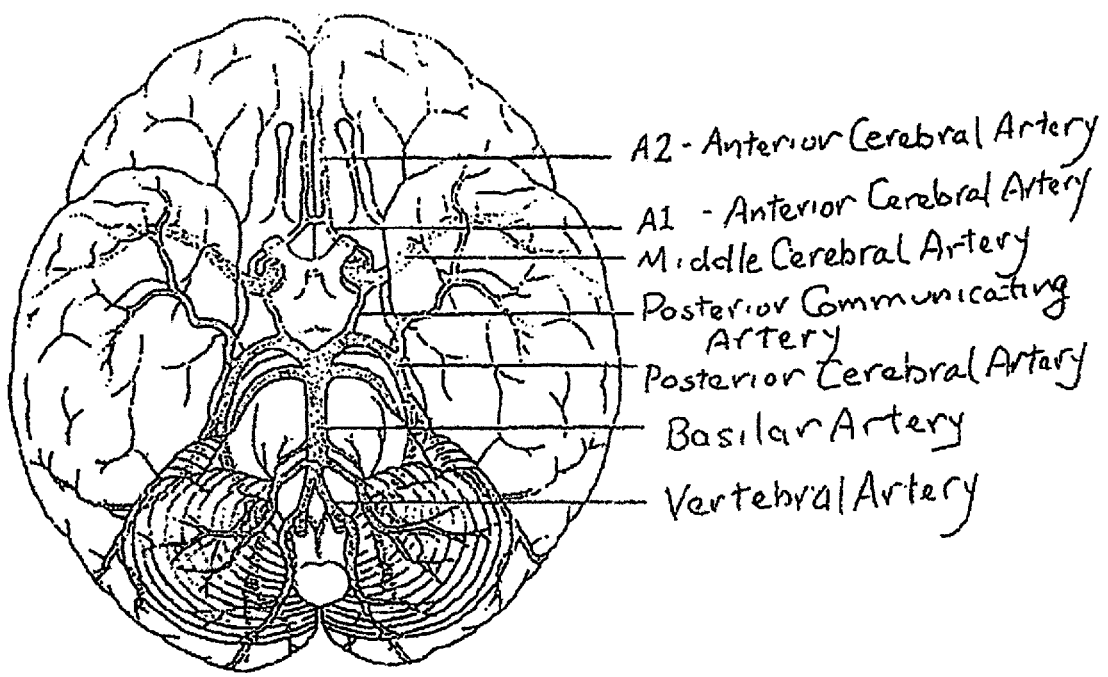
FIG. 2 shows an illustrative view of the cerebral arteries. (from Netter F H. The CIBA Collection of Medical Illustrations: Volumes 1, Nervous System. Vol. 1. Part I. CIBA: USA. 1986. pp. 256).

The present disclosure describes a variety of systems and devices that are configured to traverse one or more blood vessels (e.g. a vein or an artery) in a patient's legs, arms, torso, neck, head, etc., during the treatment of various vascular pathologies (e.g., an endovascular blockage). For example, the present disclosure describes a system that includes a (first) device that is configured for (simultaneous) rotation, irrigation, and aspiration during the maceration of a blockage as well as a (second) device (e.g., a bypass catheter), which may be used either individually or in combination.

It is envisioned that the various systems, devices, and methodologies described herein may be employed during the course of an endovascular procedure in which the patient is suffering from an arterial blockage (e.g., a thrombosis or embolus), a venous blockage, a deep vein thrombosis (e.g., in the patient's leg or arm), a myocardial infarction (e.g., brought on by a blockage such as a thrombus), a cerebral venous sinus blockage (e.g., a thrombosis), an acute stroke, or the like. As described herein below, in various embodiments of the disclosure, a method of treating a vascular blockage is described that employs a mechanical thrombectomy procedure (e.g., a proximal endovascular thrombectomy or a distal endovascular thrombectomy). It is also envisioned that the various devices and methodologies described herein may be employed in the context of a percutaneous coronary intervention (PCI) or an atherectomy. It is also envisioned that various devices and methodologies described herein may be employed in conjunction with self-expanding stents and retrievable thrombectomy stents. It is also envisioned that the various devices and methodologies described herein may be employed in the context of a valve treatment, a replacement procedure, and/or other procedures.

It is envisioned that the various systems and devices (and the components thereof) described herein below may include one or more materials. For example, it is envisioned that the devices may include one or more thermoplastic materials, one or more thermoset materials, one or more composite materials, one or more radiopaque materials, etc. Suitable thermoplastic materials include, but are not limited to, nylon, polyethylene terephthalate (PET), urethane, polyethylene, polyvinyl chloride (PVC) and polyether ether ketone (PEEK). Suitable thermoset materials include, but are not limited to, silicone, polytetrafluoroethylene (PTFE) and polyimide. Suitable composite materials include, but are not limited to, liquid crystal polymers (LCP). LCPs are partially crystalline aromatic polyesters based on p-hydroxybenzoic acid and related monomers. LCPs are highly ordered structures when in the liquid comprises, but the degree of order is less than that of a regular solid crystal. LCPs can be substituted for such materials as ceramics, metals, composites, and other plastics due to their strength at extreme temperatures and resistance to chemicals, weathering, radiation, and heat. Non-limiting examples of LCPs include wholly or partially aromatic polyesters or copolyesters such as XYDAR® (Amoco) or VECTRA® (Hoechst Celanese). Other commercial liquid crystal polymers include SUMIKOSUPER™ and EKONOL™ (Sumitomo Chemical), DuPont HX™ and DuPont ZENITE™ (E.I. DuPont de Nemours), RODRUN™ (Unitika) and GRANLAR™ (Grandmont). Suitable radiopaque materials include, but are not limited to, barium sulfate, bismuth oxychloride, tantalum, and the like.

Figure 3:
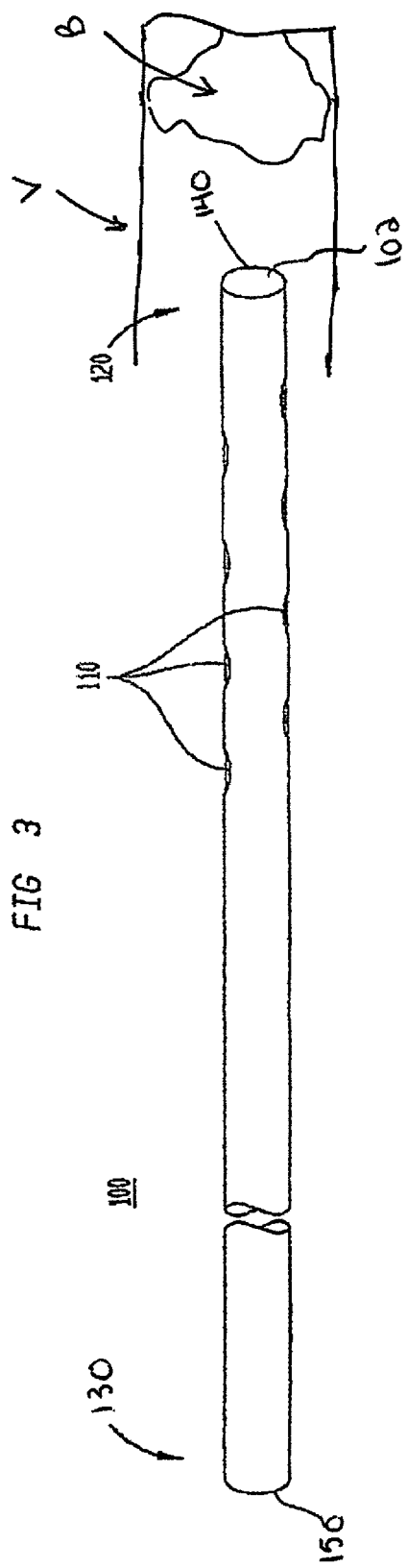
FIG. 3 shows an illustration of a side view of one aspect of the presently disclosed endovascular device (system).

FIG. 3 illustrates an endovascular treatment device (system) that is configured as a catheter 100 (also referred to herein as microcatheter 100) having respective distal (front) and proximal (rear) ends 120, 130 and defining an axial (longitudinal) length that lies substantially within the range of (approximately) 5 cm to (approximately) 500 cm. Embodiments in which the axial length of the microcatheter 100 may lie outside this range, however, are also contemplated herein and would not be beyond the scope of the present disclosure.

Although shown as being including (generally) circular outer and inner transverse cross-sectional configurations, it should be appreciated that the particular configuration of the microcatheter 100 may be varied without departing from the scope of the present disclosure. For example, it is envisioned that the microcatheter 100 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the microcatheter 100 may be circular and that the inner transverse cross-sectional configuration of the microcatheter 100 may be non-circular. It is also envisioned that the outer transverse cross-sectional configuration of the microcatheter 100 may be non-circular and that the inner transverse cross-sectional configuration of the microcatheter 100 may be circular.

The catheter 100 defines an outer transverse cross-sectional dimension (e.g., a diameter) that lies substantially within the range of (approximately) 0.1 French to (approximately) 34 French and an luminal space 102 that defines an inner transverse cross-sectional dimension (e.g., a diameter) that lies substantially within the range of (approximately) 0.05 French to (approximately) 32 French. Embodiments in which the outer transverse cross-sectional dimension of the microcatheter 100 and/or the inner transverse cross-sectional dimension of the intraluminal space lie outside the disclosed ranges, however, are also contemplated herein and would not be beyond the scope of the present disclosure. For example, it is envisioned that the outer transverse cross-sectional dimension of the microcatheter 100 and/or the inner transverse cross-sectional dimension of the intraluminal space may each be less than 0.1 and 0.05 French, respectively.

In certain embodiments, it is envisioned that the outer transverse cross-sectional dimension of the catheter 100 may be (generally) uniform (consistent) between the ends 120, 130 thereof. It is also envisioned, however, that the outer transverse cross-sectional dimension of the catheter 100 may be non-uniform (variable) between the ends 120, 130 thereof. For example, embodiments are envisioned in which the outer transverse cross-sectional dimension of the microcatheter 100 at the end 130 may be greater than the outer transverse cross-sectional dimension of the catheter 100 at the end 120 as are embodiments in which the outer transverse cross-sectional dimension of the microcatheter 100 at the end 130 may be less than the outer transverse cross-sectional dimension of the catheter 100 at the end 120.

In certain embodiments, it is envisioned that the inner transverse cross-sectional dimension of the intraluminal space may be (generally) uniform (consistent) between the ends 120, 130 thereof. It is also envisioned, however, that the inner transverse cross-sectional dimension of the intraluminal space may be non-uniform (variable) between the ends 120, 130 thereof. For example, embodiments are envisioned in which the inner transverse cross-sectional dimension of the intraluminal space at the end 130 may be greater than the inner transverse cross-sectional dimension of the intraluminal space at the end 120 as are embodiments in which the inner transverse cross-sectional dimension of the intraluminal space at the end 130 may be less than the inner transverse cross-sectional dimension of the intraluminal space.

The catheter 100 (e.g., the intraluminal space) is configured to communicate fluid to any suitable location within a blood vessel V (e.g., proximally of a blockage B, distally of the blockage B, or directly to the blockage B). According to certain embodiments, the microcatheter 100 may be configured to facilitate the irrigation of the blood vessel V proximally and/or distally of the blockage B (e.g., a thrombus). By way of a (non-limiting) example, during one method of use, it is envisioned that the microcatheter 100 may be distally advanced through the blockage B. It is also envisioned that the microcatheter 100 may be used in conjunction with an aspirator to perform a direct aspiration first pass technique (ADAPT) to irrigate locations at (adjacent to) the blockage B and or locations distal of the blockage B to inhibit (if not entirely prevent) the creation of an empty vacuum distally of the blockage B. In such methods of use, it is envisioned that the blockage B may then be aspirated proximally and extracted.

It is also envisioned that the microcatheter 100 (e.g., the intraluminal space) may be configured to provide fibrinolytics to the site of the blockage B. For example, it is envisioned that the catheter 100 (e.g., the intraluminal space) may be configured to communicate fluid (e.g., a saline solution, Alteplase, a HEP-saline, a neuro-protective cooled solution, a neuro-protective liquid(s), etc.) to locations proximal of the blockage B, distal of the blockage B, and/or within the blockage B. Depending upon the particular intended use of the microcatheter 100 (e.g., the requirements of the particular procedure being performed), it is envisioned that the microcatheter 100 (e.g., the intraluminal space) may be configured to communicate such fluids without compromising, obstructing, or otherwise interfering with the suction applied by an aspirator.

The catheter 100 may include (e.g., may be formed partially or entirely from) any suitable material including, for example, silicone, polyurethane, polyethylene, polytetrafluoroethylene (PTFE), polyethylene terephthalate (PET), latex, thermoplastic elastomers, and/or other materials, either exclusively or in combination.

According to certain embodiments, it is envisioned that the catheter 100 may include a layered construction. For example, it is envisioned that the catheter 100 may include a first (e.g., inner) layer that incorporates a first material and a second (e.g., outer) layer that incorporates a second material.

To increase the strength and/or the rigidity of the catheter 100, in certain embodiments, it is envisioned that the catheter 100 may include one or more reinforcing materials (e.g., steel), members, or the like (e.g., between adjacent layers).

It is envisioned that the catheter 100 may be configured to withstand an internal pressure that lies substantially within the range of (approximately) 0.1 psi to (approximately) 2000 psi (e.g., via the incorporation of particular materials and/or dimensioning). Embodiments in which the catheter 100 may be configured to withstand an internal pressure that lies outside the disclosed range, however, are also contemplated herein and would not be beyond the scope of the present disclosure. For example, it is envisioned that the catheter 100 may be configured to withstand an internal pressure greater than 2000 psi.

It is envisioned that the catheter 100 may be configured to withstand an internal pressure that varies between the ends thereof. For example, it is envisioned that the catheter 100 may be configured to withstand a greater pressure at the rear end 130 and a lesser pressure at the front end 120. For example, it is envisioned that the catheter 100 may be configured to withstand pressures at the rear end 130 and the front end 120 at ratios between (approximately) 1.5:1 and (approximately) 10:1.

As seen in FIG. 3, for example, the catheter 100 includes a plurality of side holes 110 that are located around the periphery (e.g., the circumference) thereof. Embodiments including a single side hole 110, however, are also contemplated herein. In the particular embodiment of the disclosure illustrated, the side holes 110 are shown as being located at the distal end 120 of the microcatheter 100. For example, it is envisioned that the side holes 110 may span a length (region) of the catheter 110 that lies substantially within the range of (approximately) 0.1 cm to (approximately) 60 cm (e.g., measured from the distal end 120). Embodiments in which the particular location of the side holes 110 may be varied are also contemplated herein, as elaborated upon below. For example, embodiments in which the side holes 110 span a length of the microcatheter 110 that is greater than 60 cm or less than 0.1 cm would not be beyond the scope of the present disclosure.

Although illustrated as being (generally) linear in configuration, in alternate embodiments of the disclosure, it is envisioned that the catheter 100 may include a non-linear configuration. For example, it is envisioned that the microcatheter 100 may include one or more bends and/or curves (e.g., at or adjacent to the side hole(s) 110 or other suitable locations) defining an angle that lies substantially within the range of (approximately) 5 degrees to (approximately) 85 degrees (e.g., such that the catheter 100 includes a repeating curve, a sinusoidal configuration, an irregular shape, or any other suitable or desirable configuration). Embodiments in which the bends may define an angle that lies outside of the range, however, are also contemplated herein and would not be beyond the scope of the present disclosure. It is envisioned that the inclusion of one or more such bends may increase the efficacy of the microcatheter 100 during the treatment of larger blood vessels (e.g., the patient's pulmonary artery, the patient's iliac vein, the patient's IVC, etc.) by allowing the device to effectively sweep along the walls of the blood vessel V (FIG. 3).

According to some embodiments, the catheter 100 further comprises a front (distal) hole 140 located at a tip of the front end 120 and a rear (proximal) hole 150 located at a tip of the rear end 130. The rear hole 150 is configured to receive a fluid from outside a patient's body, and may be in communication with a leur lock or other connecting feature, and each of the side holes 110 and the front hole 140 are configured to communicate fluid therethrough such that fluid is ejected from the catheter 100 into the patient's vasculature.

In various embodiments of the catheter 100, it is envisioned that one or more of the number of side holes 110, the spacing of the side holes 110, the proximity of the side holes 110 in relation to the ends 120, 130 of the catheter 100, the length over which the side holes 100 exist, the shape of the side holes 110, the diameter of the side holes 110, the wall thickness of the catheter 100, and the inner and outer diameters of the microcatheter 100 may be varied.

In certain embodiments of the catheter 100, it is envisioned that the side holes 110 may be evenly spaced about the periphery of the catheter 100. Alternatively, it is envisioned that the side holes 110 may be randomly oriented and spaced around the periphery of the catheter 100. It is also envisioned that the side holes 110 may be spaced in a repeating pattern about the periphery of the catheter 100, as are other configurations.

Although shown as being (generally) circular in configuration throughout the figures, it should be appreciated that the particular configuration of the side hole 110 may be varied without departing from the scope of the present disclosure. For example, it is envisioned that the side holes 110 may be regular in configuration (e.g., oval, square, rectangular, triangular, trapezoidal, diamond, pentagonal, hexagonal, heptagonal, octagonal, nonagonal, decagonal, etc.) or irregular in configuration, either exclusively or in combination.

It is envisioned that the side holes 110 may define a maximum transverse cross-sectional dimension (e.g., a diameter) that is greater than, less than, or (approximately) equal to that of the front hole 140 and/or the rear hole 150. For example, it is envisioned that the side holes 110 may define a maximum transverse cross-sectional dimension that lies substantially within the range of (approximately) 0.01 French to (approximately) 17 French. Embodiments in which the maximum transverse cross-sectional dimension defined by the side holes 100 lies outside the disclosed range, however, are also contemplated herein and would not be beyond the scope of the present disclosure. For example, it is envisioned that the maximum transverse cross-sectional dimension defined by the side holes 110 may be less than 0.01 French.

It is also envisioned that the side holes 110 may be oriented at any suitable angle relative to the front hole 140. For example, it is envisioned that the side holes 110 may be oriented at any angle relative to the front hole 140 that lies substantially within the range of (approximately) 10 degrees to (approximately) (e.g., (approximately) 90 degrees). It is also envisioned that the side holes 110 may each be oriented at the same angle (relative to the front hole 140) or that one or more of the side holes 110 may be oriented at different angles.

Figure 4:
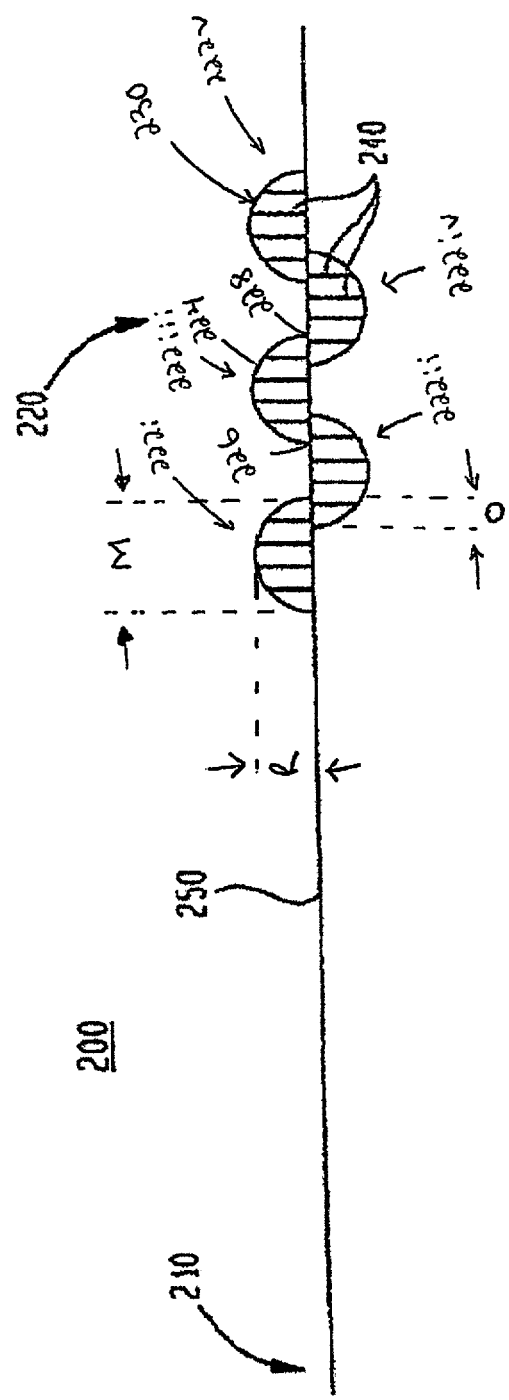
FIG. 4 shows an illustration of a side view of one aspect of the endovascular device (system) of the present disclosure.

FIG. 4 shows an exemplary and non-limiting example of an endovascular treatment device (system) according to another aspect of the present disclosure. More specifically, the endovascular device is configured as a macerating wire 200 (also referred to herein as macerating microwire 200) that includes a central wire 250 having a proximal (rear, first) end 210 and a distal (forward, second) end 220, which may include a soft wire tip, a soft round metal atraumatic ball tip, or any other structure or configuration suitable for the intended purpose of facilitating the maceration of the blockage B (see, e.g., FIG. 3) in the manner described herein.

It is envisioned that the wire 200 may define any suitable axial (longitudinal) length. For example, it is envisioned that the wire 200 may define an axial length that lies substantially within the range of (approximately) 5 cm to (approximately) 500 cm. Embodiments in which the axial length of the wire 200 may lie outside this range, however, are also contemplated herein and would not be beyond the scope of the present disclosure.

In the illustrated embodiment, the central wire 250 defines a transverse cross-sectional dimension (e.g., a diameter) that lies substantially within the range of (approximately) 0.001 inches to (approximately) 0.1 inches. Embodiments in which the transverse cross-sectional dimension of the central wire 250 may lie outside the disclosed range, however, are also contemplated herein and would not be beyond the scope of the present disclosure.

The central wire 250 supports one or more macerating members 222 that extend radially outwardly therefrom to define a radial dimension R. In the illustrated embodiment, the macerating members are configured as half-loop structures 230 that each define a generally arcuate contour (profile) that follows a continuously curved path. It is also envisioned, however, that the half-loop structure(s) 230 may follow an irregular path. For example, it is envisioned that the half-loop structure(s) 230 may include two or more straight sections that are connected at any suitable angle (e.g., less than 180 degrees). It should be appreciated, however, that alternate configurations for the macerating member(s) 222 are envisioned herein and would not be beyond the scope of the present disclosure.

Although illustrated as being (generally) linear in configuration, in alternate embodiments of the disclosure, it is envisioned that the central wire 250 may include a non-linear configuration. For example, it is envisioned that the central wire 250 may include one or more bends and/or curves (e.g., at or adjacent to the macerating member(s) 222) defining an angle that lies substantially within the range of (approximately) 5 degrees to (approximately) 85 degrees (e.g., such that the macerating microwire 200 includes a repeating curve, a sinusoidal configuration, an irregular shape, or any other suitable or desirable configuration). Embodiments in which the bends may define an angle that lies outside of the range, however, are also contemplated herein and would not be beyond the scope of the present disclosure. It is envisioned that the inclusion of one or more such bends may increase the efficacy of the macerating microwire 200 during the treatment of larger blood vessels (e.g., the patient's pulmonary artery, the patient's iliac vein, the patient's IVC, etc.) by allowing the device to effectively sweep along the walls of the blood vessel V (FIG. 3).

In various embodiments, it is envisioned that the macerating member(s) 222 and the central wire 250 may include (e.g., may be formed partially or entirely from) materials that are either identical or non-identical such that stiffness (e.g., the ability to resist deformation in response to an applied force) and/or rigidity of the macerating microwire 200 may be either uniform or variable. For example, it is envisioned that the material(s) utilized in construction of the macerating member(s) 222 may be more flexible than the material(s) used in construction of the central wire 250. For example, it is envisioned that the macerating member(s) 222 may include one or more resilient materials that allows the macerating member(s) 222 to deform (deflect) during use of the macerating microwire 200 (e.g., upon contact with the blockage B (FIG. 3)) and return to a normal (initial) configuration and that the stiffness of the macerating member(s) 222 may be less than the rotational stiffness of the central wire 250. It is also envisioned, however, that the macerating member(s) 222 may be configured so as to reduce (if not entirely prevent) deformation (deflection) (e.g., upon contact with the blockage B). It is also envisioned that stiffness among the macerating member(s) 222 may be either consistent (e.g., such that each macerating member 222 includes a (generally) identical stiffness) or variable (e.g., such that stiffness varies between the macerating member(s) 222, whereby the stiffness of certain macerating member(s) 222 may exceed that of certain others).

In the particular embodiment illustrated, the macerating members 222 are (substantially) identical in configuration and dimensions and each define an axial (longitudinal) length M that lies substantially within the range of (approximately) 0.1 m to (approximately) 5 cm. Embodiments in which the axial length M of the may lie outside this range, however, are also contemplated herein and would not be beyond the scope of the present disclosure.

Depending upon the particular intended use of the macerating wire 200, the nature of the blockage B (FIG. 3) being treated, etc., it is envisioned, however, that the macerating wire 200 may include macerating members 222 that vary in configuration and/or dimensions, that the size and/or construction of the macerating member(s) 222 may be varied, etc., so as to achieve any desired effect.

While the macerating wire 200 is shown as including five macerating members 222*i*-222*v* in FIG. 4, it should be appreciated that the number of macerating members 222 may be increased or decreased in alternate embodiments without departing from the scope of the present disclosure. For example, embodiments including a single macerating member 222 are also contemplated herein.

Each macerating members 222 includes a second wire 224 (also referred to herein as second microwire 224) having proximal (rear, first) and distal (forward, second) ends 226, 228 that are attached (connected) to the central wire 250. In the particular embodiment illustrated, the second wire 224 defines a transverse cross-sectional dimension (e.g., a diameter) that (substantially) approximates that of the central wire 250. Embodiments are also envisioned, however, in which the transverse cross-sectional dimension of the second wire 224 may be greater than or less than that of the central wire 250. For example, it is envisioned that the second microwire 224 may define a transverse cross-sectional dimension that lies substantially within the range of (approximately) 0.001 inches to (approximately) 0.1 inches. Embodiments in which the transverse cross-sectional dimension of the central wire 250 may lie outside the disclosed range, however, are also contemplated herein and would not be beyond the scope of the present disclosure.

In the illustrated embodiment, the macerating members 222 are oriented along the central wire 250 in a (generally) linear manner (e.g., such that the ends 226, 228 of each second microwire 224 are connected by a line that extends in (generally) parallel relation to the central wire 250). It is also envisioned, however, that the macerating members 222 may be oriented along the central wire 250 in a non-linear (e.g., spiraled) manner such that the ends 226, 228 of each second microwire 224 are offset from each other by any suitable angle (e.g., such that the ends 226, 228 are connected by a line that extends in non-parallel relation to the central wire 250), whereby the second wire(s) 224 are twisted around the central wire 250. For example, it is envisioned that the ends 226, 228 of each second microwire 224 may be offset from each other by an angle that lies substantially within the range of (approximately) 5 degrees to (approximately) 1080 degrees. Angular offsets between eh ends 226, 228 of each second wire 224 outside the disclosed range, however, are also contemplated herein and would not be beyond the scope of the present disclosure.

Each of the second wires 224 is connected to the central wire 250 by one or more cross struts (e.g., wires) 240. While each macerating member 222 is illustrated as including four cross struts (e.g., wires) 240 in the particular embodiment of the disclosure illustrated, depending upon the particular intended use of the macerating microwire 200, the nature of the blockage B (FIG. 3) being treated, etc., it is envisioned that the number and/or the configuration of the cross strut(s) 240 may be varied. For example, it is envisioned that the number of the cross struts 240 may lie substantially within the range of (approximately) 1 to (approximately) 100 (or more) and that the cross struts 240 may be omitted altogether.

In the illustrated embodiment, each cross strut 240 is illustrated as being (generally) linear in configuration. It is also envisioned, however, that one or more of the cross struts 240 may include a non-linear configuration. For example, it is envisioned that one or more of the cross-struts 240 may include a curved configuration or a bifurcation (e.g., such that one or more of the cross struts 240 are connected to each other).

Additionally, while each cross strut 240 is illustrated as defining a transverse cross-sectional dimension (e.g., a diameter) that (substantially) approximates that of the central wire 250 and each of the second microwires 224, embodiments are also envisioned in which the transverse cross-sectional dimension of the cross struts 240 may be greater than or less than those of the central wire 250 and/or the second microwires 224.

With continued reference to FIG. 4, in the illustrated embodiment, the cross struts 240 are configured such that they extend from the central wire 250 in (generally) orthogonal relation so as to define an angle of (approximately) 90 degrees therebetween. Embodiments are envisioned, however, in which the cross struts 240 may extend from the central wire 250 in non-orthogonal relation (e.g., so as to define any suitable acute angle therebetween).

In the particular embodiment of the disclosure illustrated, adjacent macerating members 222 are (angularly) offset from each other along the periphery (e.g., the circumference) of the central wire 250 by (approximately) 180 degrees. In alternate embodiments of the disclosure, however, it is envisioned that the (angular) offset between adjacent macerating members 222 may be varied in any suitable manner (e.g., to alter the mechanical effect of the macerating wire 200 on the blockage B (FIG. 3)). For example, it is envisioned that the (angular) offset between adjacent macerating members 222 may lie substantially within the range of (approximately) 10 degrees to (approximately) 350 degrees (e.g., to achieve any degree of desired (angular) overlap between adjacent macerating members 222 or eliminate any such overlap). Additionally, while the (angular) offset between adjacent macerating members 222 is illustrated as being (generally) uniform along the length of the central wire 250, in alternate embodiments of the disclosure, it is envisioned that the (angular) offset between adjacent macerating members 222 may vary along the length of the central wire 250. For example, it is envisioned that the macerating member 222*ii* may be (angularly) offset from the macerating member 222*i* by (approximately) 45 degrees, that the macerating member 222*iii* may be (angularly) offset from the macerating member 222*i* by (approximately) 90 degrees, that the macerating member 222*iv* may be (angularly) offset from the macerating member 222*i* by (approximately) 135 degrees, and that the macerating member 222*v* may be (angularly) offset from the macerating member 222*i* by (approximately) 180 degrees, etc.

The macerating members 222 are located along the central wire 250 in overlapping relation such that the distal end 228 of each macerating member 222 is located distally of the proximal end 226 of the adjacent macerating member 222 (e.g., such that adjacent macerating members 222 define an overlap O that is greater than 0 and less than 100% of the axial (longitudinal) length thereof). For example, in the illustrated embodiment, the macerating wire 200 is configured such that the overlap O between adjacent macerating members 222 is (generally) uniform and is (approximately) equally to 33% of the length M. Embodiments are also envisioned, however, in which the overlap O between adjacent macerating members 222 may be varied in any suitable manner (e.g., to alter the mechanical effect of the macerating microwire 200 on the blockage B). For example, it is envisioned that the overlap O between the macerating members 222i, 222ii may differ from that between the macerating members 222ii, 222iii, etc. . . .

Embodiments of the disclosure are also envisioned in which the macerating members 222 may be spaced axially (longitudinally) from each other along the length of the central wire 250 in non-overlapping relation such that the distal end 228 of each macerating member 222 is spaced proximally from the proximal end 226 of the adjacent macerating member 222.

It is also envisioned that the proximal end 210 of the microwire 200 may be configured for connection to a power-driven device to facilitate rotation of the macerating wire 200 (e.g., about a central longitudinal axis of the central wire 250). In such embodiments, it is envisioned that the power-driven device may be powered in any suitable manner (e.g., via a battery, RF current, etc.).

During use of the macerating wire 200, it is envisioned that the distal end 220 of the central wire 250 may be brought into contact with the blockage B (FIG. 3). Additionally, or alternatively, it is envisioned that the macerating wire 200 may be used to treat the blockage B via contact with macerating member(s) 222 and rotation of the macerating microwire 200 to thereby agitate, break up, or otherwise fragment the blockage B. To facilitate removal of the blockage B and/or any debris created during treatment, it is envisioned that the macerating microwire 200 may be used in conjunction with an aspirator, and/or a filter, and/or a filter-tipped catheter.

Figure 5:
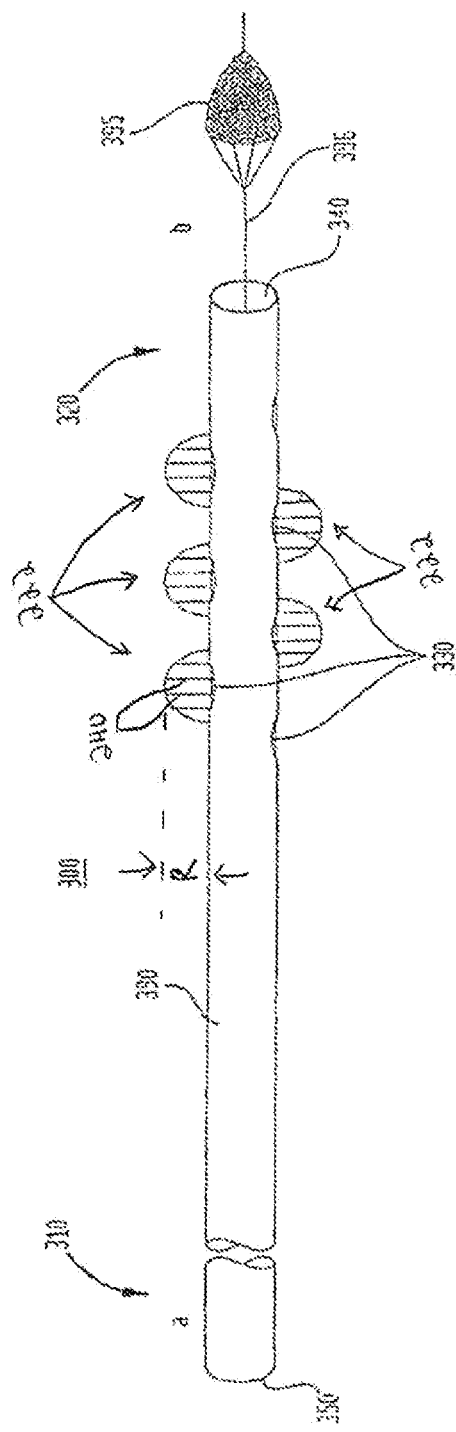
FIG. 5 shows an illustration of a side view of one aspect of the endovascular device (system) of the present disclosure.
Figure 5A:
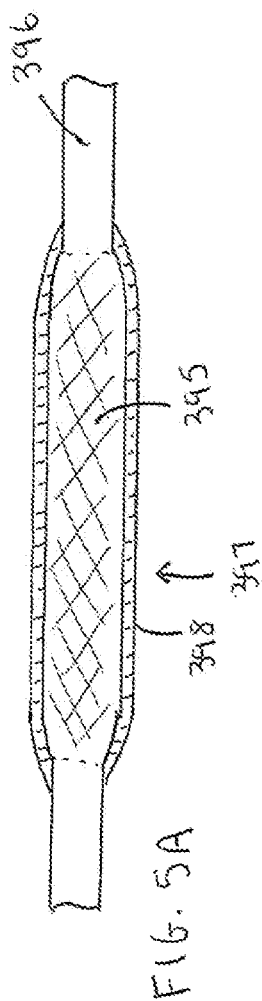
FIG. 5A shows an illustration of a side view of another aspect of the endovascular device (system) of the present disclosure.
Figure 5B:
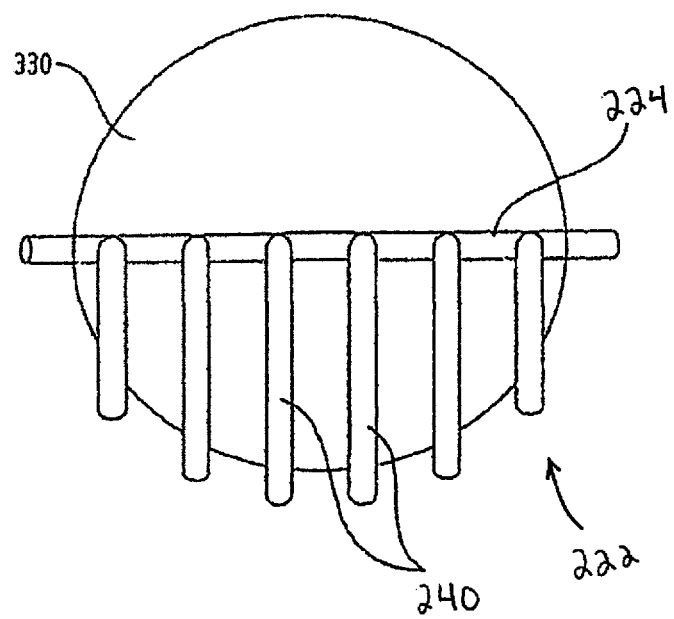
FIG. 5B shows a top view of one embodiment of the side hole and half loop structure of the present disclosure.
Figure 5C:
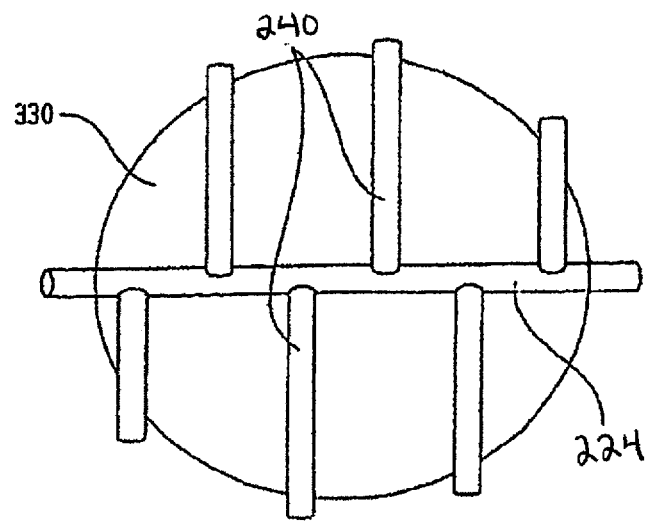
FIG. 5C shows a top view of one embodiment of the side hole and half loop structure of the present disclosure.
Figure 5D:
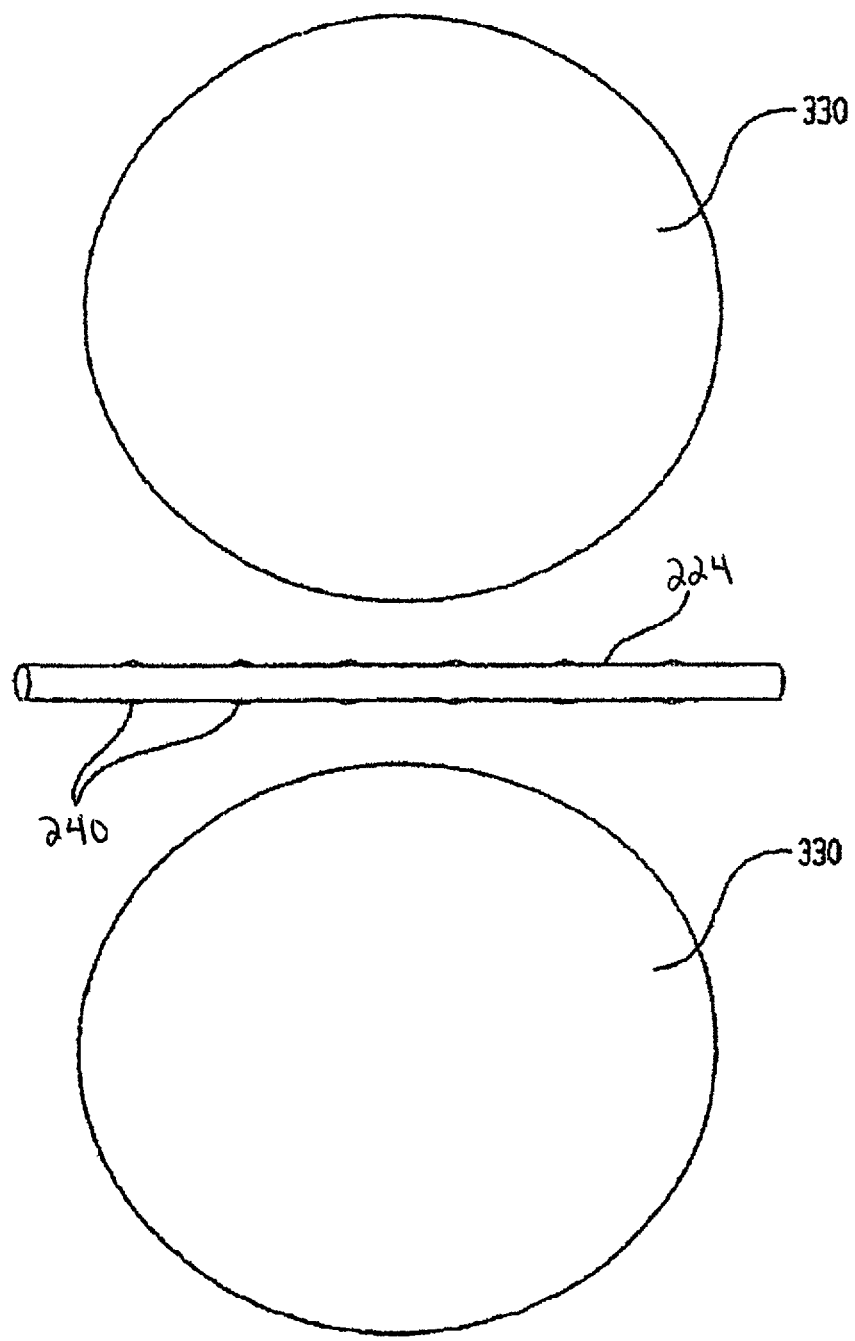
FIG. 5D shows a top view of one embodiment of the side hole and half loop structure of the present disclosure.

FIGS. 5 through 5D illustrate an embodiment of the disclosure in which the disclosed system includes a treatment device that is configured as a macerating irrigation catheter (hypotube) 300. The macerating irrigation catheter (hypotube) 300 includes a (central) tube (body) 390 having respective proximal (rear, first) and distal (forward, second) ends 310, 320. The body 390 defines an outer transverse cross-sectional dimension (e.g., a diameter) that lies substantially within the range of (approximately) 0.1 French to (approximately) 34 French and an luminal space that defines an inner transverse cross-sectional dimension (e.g., a diameter) that lies substantially within the range of (approximately) 0.1 French to (approximately) 32 French. Embodiments in which the outer transverse cross-sectional dimension of the tube 390 and/or the inner transverse cross-sectional dimension of the intraluminal space may lie outside the disclosed ranges, however, are also contemplated herein and would not be beyond the scope of the present disclosure. For example, it is envisioned that the outer transverse cross-sectional dimension of the tube 390 and/or the inner transverse cross-sectional dimension of the intraluminal space may be less than 0.1 French (e.g., (approximately) 0.01 mm). It is also envisioned that the outer transverse cross-sectional dimension of the tube 390 may be greater than 34 French (e.g., (approximately) 100 mm).

Although shown as being including (generally) circular outer and inner transverse cross-sectional configurations, it should be appreciated that the particular configuration of the macerating irrigation catheter 300 may be varied without departing from the scope of the present disclosure. For example, it is envisioned that the macerating irrigation catheter 300 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the macerating irrigation catheter 300 may be circular and that the inner transverse cross-sectional configuration of the macerating irrigation catheter 300 may be non-circular. It is also envisioned that the outer transverse cross-sectional configuration of the macerating irrigation catheter 300 may be non-circular and that the inner transverse cross-sectional configuration of macerating irrigation catheter 300 may be circular.

As discussed above in connection with the macerating wire 200, it is envisioned that the macerating member(s) 222 may include one or more resilient materials that allows the macerating member(s) 222 to deform (deflect) during use of the macerating irrigation catheter 300 and return to a normal (initial) configuration. It is also envisioned that the stiffness of the macerating member(s) 222 may be less than the rotational stiffness of the tube 390.

The tube 390 includes one or more side holes 330 that are configured to facilitate infusion and/or irrigation in a plurality of directions during the treatment of the blockage B (FIG. 3). Known devices by contrast, such as the Argon-Cleaner XT, communicate fluid solely through a distal end hole or an end hole located proximal to the macerating wire, which can result in a one-sided reduction of the blockage B on the opposite side that can lead to collapse resulting from the creation of a vacuum within the blood vessel V. It can also limit movement of clot and debris in the absence of flow, whereas the irrigation that can be delivered proximal to the clot, within the clot, and distal to the clot, as described herein, increases (e.g., maximizes) mobilization of clot and debris for subsequent removal.

The side holes 330 are (optionally) spaced about the periphery (e.g., the circumference) of the tube 390 (e.g., at or adjacent to the distal end 320 thereof). For example, it is envisioned that the side holes 330 may span a length (region) of the tube 390 that lies substantially within the range of (approximately) 0.5 cm to (approximately) 60 cm (e.g., measured from the distal end 320). Embodiments in which the particular location of the side holes 330 may be varied are also contemplated herein, as elaborated upon below. For example, embodiments in which the side holes 330 span a length of the tube 390 that is greater than 60 cm would not be beyond the scope of the present disclosure. There may optionally be an end hole as well.

It is envisioned that the side holes 330 may be evenly or randomly spaced about the periphery of the tube 390. For example, it is envisioned that the side holes 330 may be spaced in a repeating pattern.

Although shown as being (generally) circular in configuration throughout the figures, it should be appreciated that the particular configuration of the side hole(s) 330 may be varied without departing from the scope of the present disclosure. For example, it is envisioned that the side holes 330 may be regular in configuration (e.g., oval, square, rectangular, triangular, trapezoidal, diamond, pentagonal, hexagonal, heptagonal, octagonal, nonagonal, decagonal, etc.) or irregular in configuration, either exclusively or in combination.

According to some embodiments, the tube 390 further includes a front hole 340 located at a tip of the distal end 320 and a rear hole 350 located at a tip of the proximal end 310. In such embodiments, the rear hole 350 may be configured to receive fluid from outside a patient's body such that the fluid is ejected into the patient's vasculature through the side hole(s) 330 and/or the front hole 340. It is envisioned that fluid may optionally be injected into the proximal hole 350 using a power injector, pressurized bags, hand injections, and other modalities. It is also envisioned that the proximal end 310 of the tube 390 may include a luer lock and/or that macerating irrigation catheter 300 may include a (soft) atraumatic member (e.g., a wire) that extends distally beyond the distal end 320 (e.g., through the end hole 340). In such embodiments, it is envisioned that the atraumatic member may include any configuration and/or structure(s) suitable for the intended purpose of facilitating advancement of the macerating irrigation catheter 300 through the patient's vasculature. For example, it is envisioned that the atraumatic member may include a distal (operative) end that is either linear or non-linear in configuration and that the distal end of the atraumatic member may include (or otherwise support) a ball or any other such structure, component, or mechanism.

It is envisioned that the side holes 330 may define a maximum transverse cross-sectional dimension (e.g., a diameter) that is greater than, less than, or (approximately) equal to that of the front hole 140 and/or the rear hole 150. For example, it is envisioned that the side holes 110 may define a maximum transverse cross-sectional dimension that lies substantially within the range of (approximately) 0.01 French to (approximately) 17 French. Embodiments in which the maximum transverse cross-sectional dimension defined by the side holes 330 lies outside the disclosed range, however, are also contemplated herein and would not be beyond the scope of the present disclosure. For example, it is envisioned that the maximum transverse cross-sectional dimension defined by the side holes 110 may be less than 0.01 French.

In various embodiments of the disclosure, it is envisioned that one or more of the following components and/or features may be varied to achieve any necessary or desired result: the number of side holes 330; the axial (longitudinal) and/or angular spacing of the side holes 330; the proximity of the side holes 330 to the front hole 340; the length of the tube 390 over which the side holes 330 extend; the shape of the side holes 330; the diameter of the side holes 330; the thickness of the wall of the macerating irrigation catheter 300; the inner diameter of the tube 390; and the outer diameter of the tube 390.

Figure 9:
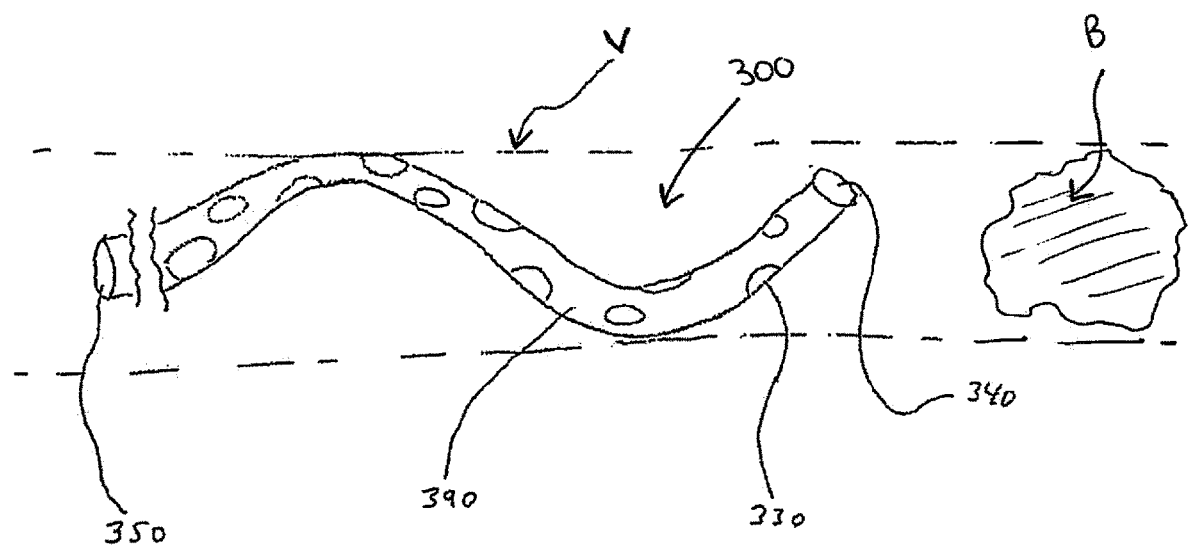
FIG. 9 illustrates a side view of the rotating, macerating and irrigating catheter (e.g. hypotube), including multiple irrigation side holes and end hole, of one embodiment of the present disclosure disposed within the lumen (cutaway) of a blood vessel.

With reference to FIG. 9, which illustrates the macerating irrigation catheter 300 positioned within the blood vessel V, it is envisioned that the tube 390 may include a sinusoidal or other such non-linear (e.g., complex) configuration to facilitate the treatment of the blockage B using the tube 390 itself (e.g., during intermittent or continuous rotation of the macerating irrigation catheter 300) as well as irrigation of the patient's vasculature (e.g., proximally of the blockage B, across the blockage B, and/or distally of the blockage B) and aspiration (e.g., via a separate component and/or capture of debris with a filter and/or a filter-tipped catheter) to inhibit (if not entirely prevent) the migration of debris (e.g., emboli), into normal capillary beds, for example, and subsequent secondary ischemic injury. For example, during maceration, it is envisioned that fluid may flow through the macerating irrigation catheter 300 either intermittently or continuously.

To further protect the patient's vasculature, it is envisioned that the macerating irrigation catheter 300 may be configured to facilitate the reversal of blood flow (e.g., proximally of the blockage B in arterial applications and/or distally of the blockage B in venous applications). It should be appreciated, however, that the venous or arterial application of one versus the other is not exclusive and depends on the positioning of the device(s) and the direction of native flow, aspiration, and/or induced flow. To enhance protection further, it is envisioned that a (semi-permeable) filter may be attached or otherwise utilized, as seen in FIGS. 7G, 10A, 11A, 12A, and 13A, for example.

According to some embodiments, the size of the side holes 330 is greater than the size of the front hole 340. According to some embodiments, the size of the side holes 330 is less than the size of the front hole 340. According to some embodiments, the size of the side holes 330 is approximately the same size as the front hole 340.

According to some embodiments, the tube 390 of the macerating irrigation microcatheter 300 is made from one or more of the following materials: silicone, polyurethane, polyethylene, polytetrafluoroethylene (PTFE), polyethylene terephthalate (PET), latex, and thermoplastic elastomers. According to some embodiments, the tube 390 of the macerating irrigation microcatheter 300 comprises an inner layer made of a first material, and an outer layer made from a second material. According to some embodiments, the tube 390 of the macerating irrigation microcatheter 300 is reinforced with steel or other suitable material.

According to some embodiments, the outer diameter of the tube 390 at the proximal end 310 is approximately the same as the outer diameter of the tube 390 at the distal end 320.

According to some embodiments, the outer diameter of the tube 390 at the proximal end 310 is greater than the outer diameter of the tube 390 at the distal end 320. According to some embodiments, the outer diameter of the tube 390 at the proximal end 310 is less than the outer diameter of the tube 390 at the distal end 320. According to some embodiments, the outer diameter of the tube 390 varies along its length.

According to some embodiments, the inner luminal diameter of the tube 390 at the proximal end 310 is approximately the same as the inner luminal diameter of the tube 390 at the distal end 320. According to some embodiments, the inner luminal diameter of the tube 390 at the proximal end 310 is greater than the inner luminal diameter of the tube 390 at the distal end 320. According to some embodiments, the inner luminal diameter of the tube 390 at the proximal end 310 is less than the inner luminal diameter of the tube 390 at the distal end 320. According to some embodiments, the inner luminal diameter of the tube 390 varies along its length.

The macerating irrigation catheter 300 (e.g., the tube 390) may include (e.g., may be formed partially or entirely from) any suitable material including, for example, silicone, polyurethane, polyethylene, polytetrafluoroethylene (PTFE), polyethylene terephthalate (PET), latex, and thermoplastic elastomers, either exclusively or in combination.

According to certain embodiments, it is envisioned that the macerating irrigation catheter 300 may include a layered construction. For example, it is envisioned that the macerating irrigation catheter 300 may include a first (e.g., inner) layer that incorporates a first material and a second (e.g., outer) layer that incorporates a second material.

To increase the strength and/or the rigidity of the macerating irrigation catheter 300, in certain embodiments, it is envisioned that the macerating irrigation catheter 300 may include one or more reinforcing materials (e.g., steel), members, or the like (e.g., between adjacent layers).

It is envisioned that the macerating irrigation catheter 300 may be configured to withstand an internal pressure that lies substantially within the range of (approximately) 0.1 psi to (approximately) 2000 psi (e.g., via the incorporation of particular materials and/or dimensioning). Embodiments in which the macerating irrigation catheter 300 may be configured to withstand an internal pressure that lies outside the disclosed range, however, are also contemplated herein and would not be beyond the scope of the present disclosure. For example, it is envisioned that the macerating irrigation catheter 300 may be configured to withstand an internal pressure greater than 2000 psi.

It is envisioned that the macerating irrigation catheter 300 may be configured to withstand an internal pressure that varies between the ends thereof. For example, it is envisioned that the macerating irrigation microcatheter 300 may be configured to withstand a greater pressure at the rear end 310 and a lesser pressure at the front end 320. For example, it is envisioned that the macerating irrigation catheter 300 may be configured to withstand pressures at the rear end 310 and the front end 320 at ratios between (approximately) 1.5:1 and (approximately) 10:1.

According to some embodiments, such as that seen in FIG. 5, for example, to increase the macerating capabilities of the macerating irrigation catheter 300, it is envisioned that the macerating irrigation catheter 300 may further include one or more macerating members 322, which are substantially similar (if not identical to) the macerating members 222 discussed above in connection with the macerating wire 200 seen in FIG. 4. In such embodiments, the macerating members 322 extend radially outward from (e.g., are secured to) an outer surface of the tube 390 to facilitate the treatment of the blockage B (FIG. 3) via rotation of the macerating irrigation catheter 300 to thereby agitate, break up, or otherwise fragment the blockage B. To facilitate removal of the blockage B and/or any debris created during treatment, it is envisioned that the macerating irrigation catheter 300 may be used in conjunction with an aspirator, a filter, and/or a filter-tipped catheter.

It is envisioned that the macerating members 222 may be spaced axially (longitudinally) from the side holes 330 (e.g., along the length of the tube 390) and/or angularly from the side holes 330 (e.g., along the circumference of the tube 390) to avoid any overlap therebetween (see, e.g., FIG. 5D). Alternatively, however, it is envisioned that the macerating members 222 may be positioned in (partial or complete) alignment with the side holes 330, axially and/or angularly. It is envisioned that (partial or complete) alignment between the macerating members 222 and the side holes 330 may increase the efficacy of the macerating irrigation catheter 300 in treating (macerating, breaking up) a blockage B by reducing the size of the debris created to facilitate removal of the blockage B and the debris via an aspirating catheter located proximally or distally of the blockage B while also reducing any likelihood that the aspirating catheter may become clogged. It is also envisioned that by varying the extent of the overlap between the macerating members 222 and the side holes 330, the size of the debris created during treatment of the blockage B may be altered in any necessary or desired manner (e.g., by varying the number and/or the position of the macerating members 222 in relation to the side holes 330).

Embodiments are envisioned in which each of the macerating members 222 is oriented in identical relation to the side holes 330 (e.g., such that each of the macerating members 222 is aligned with one or more corresponding side holes 333 in a (generally) identical manner). Embodiments are also envisioned, however, in which the orientation of the macerating members 222 in relation to the side holes 330 may vary along the length of the tube 390. For example, it is envisioned that the macerating irrigation catheter 300 may include one or more macerating members 222 that are (partially or completely) aligned with the side holes 330 and one or more macerating members 222 that are oriented out of alignment with the side holes 333. It is further envisioned that the macerating irrigation microcatheter 300 may include one or more macerating members 222 that are (partially or completely) aligned with the side holes 330 to a first extent and one or more macerating members 222 that are (partially or completely) aligned with the side holes 330 to a different extent.

In certain embodiments, it is envisioned that the macerating members 222 may span a portion of a side hole 330 and that each of the corresponding cross struts 240 may extend in a common direction. For example, FIG. 5B illustrates an embodiment in which the macerating members 222 span a midline of the side hole 330. FIG. 5C, by contrast, illustrates an embodiment in which the cross struts 240 extend in opposing directions (e.g. in an alternating fashion).

FIG. 5D illustrates an embodiment in which one or more of the macerating members 222 are oriented such that the second wire 224 is located between adjacent side holes 330 so as to avoid any overlap between the side holes 330 and the second wire 224 (and the cross struts 240).

It is envisioned that the lengths of the second wire 224 and the cross struts 240 maybe altered to vary the radial dimension R (FIGS. 4, 5) of the macerating members 222, which may be defined in relation to the transverse cross-sectional dimension (e.g., the diameter) of the tube 390. For example, it is envisioned that the radial dimension R may be (approximately) equivalent to the transverse cross-sectional dimension of the tube 390. It is also envisioned that the radial dimension R may be less than or greater than the transverse cross-sectional dimension of the tube 390. For example, the radial dimension R may be half (or less than half) of the transverse cross-sectional dimension of the tube 390 or the radial dimension may be twice, three times, four times, five time, six times, or more than the transverse cross-sectional dimension of the tube 390.

In certain embodiments, it is envisioned that the proximal end 310 of the tube 390 may be configured for connection to a power-driven motor to facilitated rotation of the macerating irrigation catheter 300 (e.g., about a central longitudinal axis of the tube 390). In such embodiments, it is envisioned that the power-driven motor may be powered in any suitable manner (e.g., via a battery, RF current, etc.). Manual rotation may also be utilized.

With reference again to FIG. 5, in certain embodiments, it is envisioned that the macerating irrigation catheter 300 may further include a filter element 395 (e.g., a semi-permeable membrane, a net, a mesh, or other such suitable structure). For example, it is envisioned that the filter element 395 may define pores having a size that lies substantially within the range of (approximately) 0.1 μm to (approximately) 5 mm (e.g., 300 μm) and that the filter element 395 may include any suitable material or combination of materials such as, for example, polyurethane, polyester, or any other suitable fabric or polymer, either exclusively or in combination. Other sized pores are envisioned as well. To increase the strength and/or the rigidity of the filter element 395, in certain embodiments, it is further envisioned that the filter element 395 may be supported or otherwise reinforced (e.g., by nitinol members (wires) or members (wires) formed from any other suitable material(s), whether metallic or non-metallic).

In the particular embodiment illustrated, the filter element 395 is supported by (e.g., connected to) an intraluminal cable (wire) 396 that is configured for receipt by the tube 390 such that the cable 396 (and, thus, the filter element 395) and the tube 390 are configured for independent relative movement therebetween. It is envisioned that the filter element 395 may include (e.g., may be formed partially or entirely from) one or more flexible, resilient materials, which facilitates reconfiguration of the filter element 395 between a collapsed (first, non-expanded, compressed, constrained, closed) configuration, and an expanded (second, non-compressed, non-constrained, open) configuration. More specifically, in the particular embodiment illustrated, the collapsed configuration of the filter element 395 is maintained via the tube 390 (e.g., during insertion into, withdrawal from, and advancement through the macerating irrigation catheter 300). Upon deployment of the filter element 395 and exposure from the front hole 340 at the distal end 320 of the tube 390 and release of the constraint provided thereby, the flexible, resilient construction of the filter element 395 causes the filter element 395 to expand (automatically) within the blood vessel V (FIG. 3) (e.g., such that an outer rim of the filter element 395 (substantially) contacts an inner wall of the blood vessel V). Alternatively, the filter may have an independent delivery catheter or tube. Once deployed, the filter element 395 protrudes from the distal end 320 of the tube 390 (e.g., to capture any debris created during maceration that may escape aspiration). It is envisioned that the filter element 395 may be configured to capture particulate that ranges in size from (approximately) 10 μm to (approximately) 500 μm in size. A filter element 395 that is configured to capture particulate outside the disclosed range, however, would not be beyond the scope of the present disclosure. To enhance the capture of emboli, it is envisioned that the filter element 395 may be configured to (generally) conform to the patient's vasculature (e.g., to the blood vessel V).

It is envisioned that the filter element 395 may be reconfigured between the collapsed configuration and the expanded configuration via retraction and advancement of the cable 396 (and the filter element 395) in relation to the macerating irrigation catheter 300 (e.g., such that the macerating irrigation catheter 300 remains (generally) stationary). Additionally, however, it is envisioned that the filter element 395 may be reconfigured via retraction and advancement of the macerating irrigation catheter 300 in relation to the cable 396 (and the filter element 395) (e.g. such that the cable 396 and the filter element 395 remain (generally) stationary). It is further envisioned that the filter element 395 may be reconfigured via concomitant retraction and advancement of the cable 396 (and the filter element 395) and the macerating irrigation catheter 300 (e.g. such that the cable 396 and the filter element 395 are retracted into the macerating irrigation catheter 300 while the macerating irrigation catheter 300 is advanced over the cable 396 and the filter element 395).

In certain embodiments, it is envisioned that the filter element 395 may include a removable cover 397, such as a peel-away sheath 398, to further constrain the filter element 395 and maintain the collapsed configuration thereof (e.g., during insertion of the filter element 395 into the tube 390 of the macerating irrigation catheter 300), which may be removed at any suitable point in time. For example, it is envisioned that the cover 397 may be removed subsequent to insertion of the filter element 395 into the tube 390 and prior to deployment of the filter element 395 within the blood vessel V (FIG. 3). The cover 397 may be configured such that the filter element 395 defines any necessary or desired transverse cross-sectional dimension (e.g., diameter) in the collapsed configuration. For example, it is envisioned that the cover 397 may be configured such that the filter element 395 defines a transverse cross-sectional dimension, in the collapsed configuration, that lies substantially within the range of (approximately) 1 French to (approximately) 5 French (e.g., (approximately) 2 French). Transverse cross-sectional dimensions that may lie outside this range, however, are also contemplated herein and would not be beyond the scope of the present disclosure.

In certain embodiments, it is envisioned that the filter element 395 may define a (generally annular, round) opening having a transverse cross-sectional dimension (e.g., a diameter) that (substantially) approximates the outer transverse cross-sectional dimension of the tube 390. It is also envisioned, however, that the transverse cross-sectional dimension of the opening may be less than or greater than the outer transverse cross-sectional dimension of the tube 390. For example, the transverse cross-sectional dimension of the opening may be twice, three times, four times, five time, six times, seven times, eight times, nine times, ten times, or more than the transverse cross-sectional dimension of the tube 390 and may lie substantially within the range of (approximately) 0.1 cm to (approximately) 15 cm. A filter element 395 with an opening defining a transverse cross-sectional dimension outside the disclosed range, however, would not be beyond the scope of the present disclosure. The filter opening may also take other shapes, such as an oval, elliptical, etc.

Figure 5E:
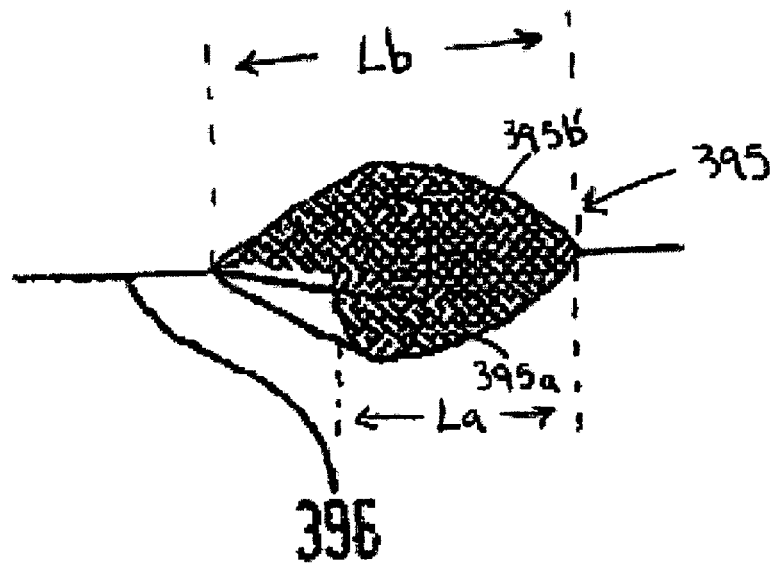
FIG. 5E shows a side view of one embodiment of a filter element of the present disclosure.
Figure 5F:
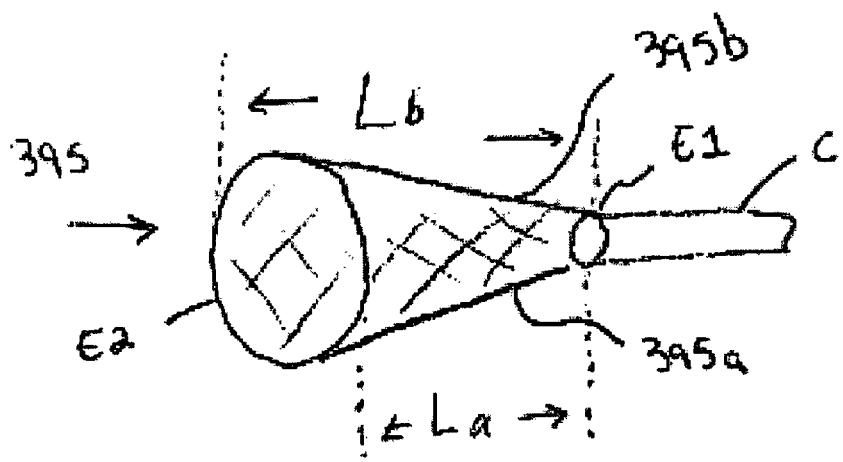
FIG. 5F shows a side view of one embodiment of a filter element of the present disclosure.
Figure 5G:
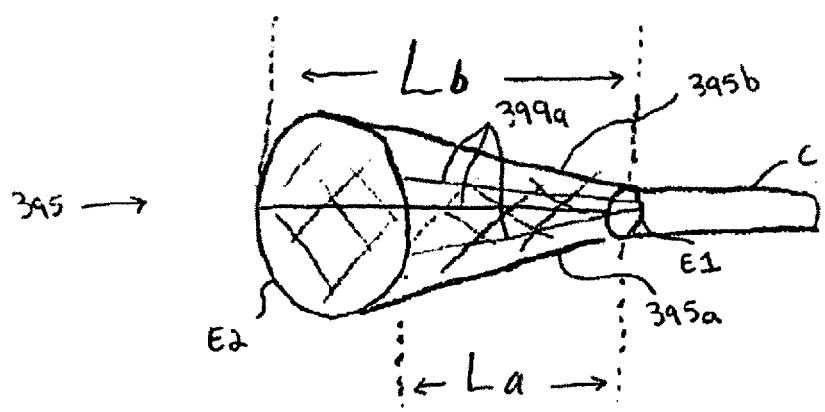
FIG. 5G shows a side view of one embodiment of a filter element of the present disclosure.
Figure 5H:
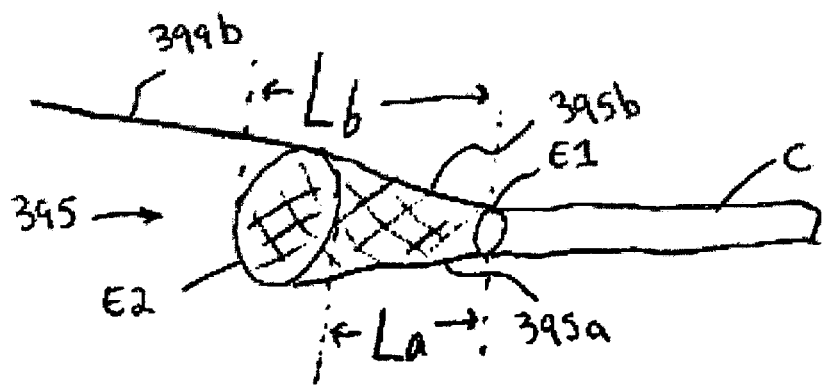
FIG. 5H shows a side view of one embodiment of a filter element of the present disclosure.
Figure 5I:
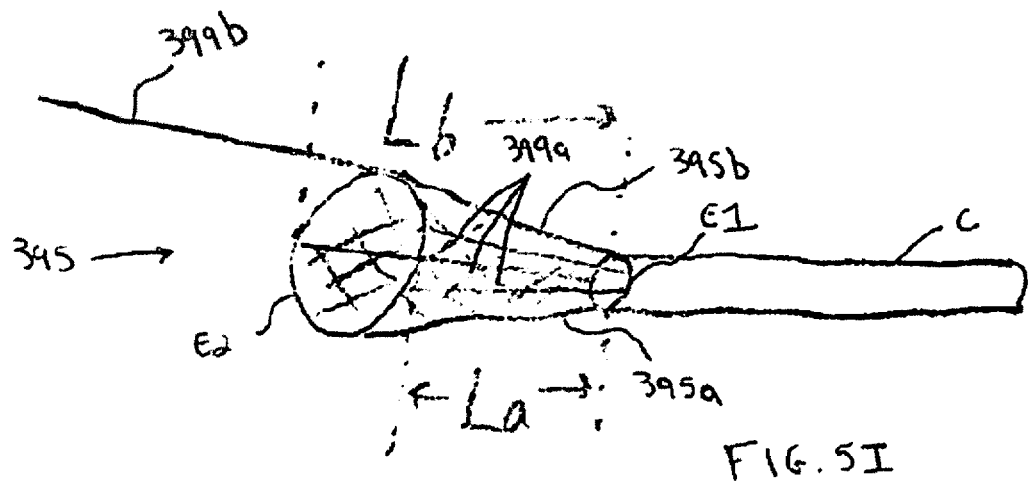
FIG. 5I shows a side view of one embodiment of a filter element of the present disclosure.

Additionally, while the filter element 395 is illustrated as including a (generally) symmetrical configuration in FIG. 5, it is also envisioned that the filter element 395 may include an asymmetrical configuration in various embodiments of the disclosure. For example, FIG. 5E illustrates an embodiment in which the filter element 395 includes a generally ovoid configuration defining a first portion (section, segment) 395*a* with a first axial (longitudinal) length La and a second portion (section, segment) 395*b* with a second axial (longitudinal) length Lb greater than the first length La. It is also envisioned that the filter element 395 may include a first end E1 that is connected to (supported by) a catheter C and an opposite (open, flared) second end E2, as seen in FIGS. 5F-5I.

In certain embodiments, it is envisioned that the filter element 395 may further include one or more strengthening members 399*a* (FIGS. 5G, 5I) (e.g., ribs, struts, or the like) and/or one or more anchor members (extensions) 399*b* (FIGS. 5H, 5I) that are configured for (substantial) engagement (contact) with an inner wall of the blood vessel V (FIG. 3) to stabilize and/or secure the filter element 395 to inhibit (if not entirely prevent) unintended rotational and/or axial movement (migration) of the filter element 395 within the blood vessel V. In the particular embodiments illustrated, the filter element 395 is shown as including three strengthening members 399*a* that are separated by a (generally) equivalent angular distance of (approximately) 120 degrees and a single anchor member 399*b* that is (generally) linear in configuration. It should be appreciated, however, that the configuration, number, and/or particular location of the strengthening member(s) 399*a* and/or the anchor member(s) 399*b* may be varied in alternate embodiments without departing from the scope of the present disclosure. For example, it is envisioned that filter element 395 may include a pair of anchor members 399*b* (e.g., positioned in (generally) diametrical opposition) and/or that the anchor member(s) 399*b* may include one or more barbs (or other such suitable structures) to enhance the engagement (contact) between the filter element 395 and the blood vessel V (FIG. 3) and, thus, securement of the filter element 395.

FIG. 6 illustrates an endovascular system including an aspiration catheter (aspirator) 400 that is configured to establish controlled vascular occlusion so as to inhibit (if not entirely prevent) anterograde flow (e.g., distally into the patient's brain or other organ). In various implementations, it is envisioned that the direction of aspiration may either be the same as the direction of blood flow or opposite to the direction of blood flow and that the aspiration catheter 400 may be configured to apply aspiration to the blood vessel V (FIG. 3) intermittently and/or continuously. Although illustrated in connection with the macerating irrigation catheter 300 in FIG. 6, it should be appreciated that the aspiration catheter 400 may be configured for use with any of the treatment devices described herein, such as, for example, the catheter 100 (FIG. 3), the macerating microwire 200 (FIG. 4), etc., to treat (e.g., agitate, break up, macerate, or otherwise fragment) the blockage B (FIG. 3) and facilitate extraction of the blockage B and/or debris via the aspiration catheter 400. To facilitate the extraction of debris, it is envisioned that the filter element 395 may be utilized such that the filter element 395 (and the intraluminal cable 396) extend through the macerating irrigation catheter 300, as seen in FIG. 6A. Fragmenting the blockage B not only facilitates more efficient extraction by the aspiration catheter 400, but may also reduce occlusion of the aspiration catheter 400 and allow for irrigation into and distally beyond the blockage B. Irrigation serves to expand that section of the blood vessel V, which decreases adherence of the blockage B to the wall of the blood vessel V, and also serves to replace the blockage B and any blood that is removed during aspiration, thereby inhibiting (if not entirely preventing) the creation of an empty vacuum within the blood vessel V that may otherwise result in (partial or complete) vessel collapse and inhibit flow and aspiration of clot and debris out of the circulation.

It is envisioned that the medical device (e.g., the catheter 100 (FIG. 3), the macerating wire 200 (FIG. 4), etc.) inserted through the aspiration catheter 400 may be advanced axially (longitudinally) through the aspiration catheter 400 such that the medical device extends distally beyond the aspiration catheter 400 by a distance that lies substantially within the range of (approximately) 0.1 cm to (approximately) 100 cm. Distances that may lie outside this range, however, are also contemplated herein and would not be beyond the scope of the present disclosure.

In the particular embodiment seen in FIG. 6, the aspiration catheter 400 includes a body 402 and one or more balloons (or other such inflatable and/or expandable members) 430 that are supported on the body 402. The body 402 includes respective proximal (rear) and distal (forward) ends 410, 420 and defines a lumen 404 that extends therethrough that is configured to receive the macerating irrigation catheter 300 (for example) and facilitate the aspiration of the blood vessel V (FIG. 3) in the manner described herein.

It is envisioned that the aspiration catheter 400 may define any suitable axial (longitudinal) length. For example, it is envisioned that the aspiration catheter 400 may define an axial length that lies substantially within the range of (approximately) 5 cm to (approximately) 500 cm. Embodiments in which the axial length of the aspiration catheter 400 may lie outside this range, however, are also contemplated herein and would not be beyond the scope of the present disclosure.

Although shown as being including (generally) circular outer and inner transverse cross-sectional configurations, it should be appreciated that the particular configuration of the aspiration catheter 400 may be varied without departing from the scope of the present disclosure. For example, it is envisioned that the aspiration catheter 400 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the aspiration catheter 400 may be circular and that the inner transverse cross-sectional configuration of the aspiration catheter 400 may be non-circular. It is also envisioned that the outer transverse cross-sectional configuration of the aspiration catheter 400 may be non-circular and that the inner transverse cross-sectional configuration of the aspiration catheter 400 may be circular.

The balloon(s) 430 are mounted on (or otherwise secured to) an exterior surface 406 of the body 402 and is configured to establish controlled occlusion of the blood vessel V (FIG. 3) upon inflation. It is envisioned that expansion of the balloon(s) 430 may also cause expansion of the blood vessel V and, when used in conjunction with irrigation and aspiration, that the balloon(s) 430 may be utilized to facilitate flow reversal in the blood vessel V and/or to inhibit (if not prevent) the distal flow of debris, emboli, or the like.

Although shown as including a single balloon 430 that is supported on the distal end 420 of the body 420 in the illustrated embodiment, it should be appreciated that the number of balloons 430 and/or the location of the balloon(s) 430 may be varied in alternate embodiments without departing from the scope of the present disclosure. It is envisioned that any suitable fluid may be utilized to inflate the balloon(s) 430 including, for example, sterile water, contrast, saline, etc.

The balloon(s) 430 may include (e.g., may be formed partially or entirely from) any suitable material or combination of materials (e.g., a polyamide, polyethylene terephthalate (PET), polyurethane, composites, and engineered nylons such as Pebax®, Grilamid®, and Vestamid®) and may include any suitable configuration (e.g., cylindrical, spherical, oval, conical, stepped, tapered, dog bone, etc.). It is also envisioned that the balloon(s) 430 may include, a conical corner that is either pointed or radiused, an offset neck, a spherical end, a square end, etc.

Each balloon 430 defines a transverse cross-sectional dimension (e.g., a diameter) that lies substantially within the range of (approximately) 0.1 mm to (approximately) 500 mm and an axial (longitudinal) length that lies substantially within the range of (approximately) 0.1 mm to (approximately) 1000 mm Embodiments of the aspiration catheter 400 devoid of the balloon 430, however, are also contemplated herein. In such embodiments, the aspiration catheter 400 may be configured such that the outer transverse cross-sectional dimension (e.g., the diameter) defined by the body 402 substantially approximates, if not slightly exceeds (e.g., on the order of up to 25%) the inner transverse cross-sectional dimension (e.g., the diameter) of the blood vessel V (FIG. 3) to occlude blood flow via apposition (wedging) with the inner wall of the blood vessel V.

It is envisioned that the aspiration catheter 400 and the macerating irrigation microcatheter 300 may be configured such that ratio of the transverse cross-sectional dimension (e.g., the diameter) of the tube 390 to the transverse cross-sectional dimension (e.g., the diameter) of the body 402 is less than (approximately) 1:100.

In some embodiments, the balloon(s) (or other such flow limiting element(s)) may be used to temporarily slow or stop normal flow in the vessel to allow irrigation and aspiration to be combined via the aspiration to result in flow into the aspiration catheter 400 and out of the body. Maceration may also be integrated to mobilize the blockage B and/or debris which then flows into the aspiration catheter 400 with the irrigation fluid via the aspiration applied to the aspiration catheter 400 outside the patient's body and subsequently out of the vessel and out of the body.

FIG. 7A illustrates an embodiment of the presently disclosed endovascular device (system) in which the catheter 100 (FIG. 3) extends through (or is otherwise incorporated into a wall of) the aspiration catheter 400 (e.g., to reduce or minimize effective diminution of the lumen 404 and/or increase or maximize flow). For example, it is envisioned that the catheter 100 may extend through the lumen 404 of the body 402 or that the microcatheter 100 may extend through (e.g., may be embedded in) the wall of the body 402. In certain embodiments, it is envisioned that the microcatheter 100 may be connected to an inner surface 408 defined by the body 402, as seen in FIG. 7A, to increase (e.g., maximize) the aspiration force applied by the aspiration catheter 400. It is also envisioned that the microcatheter 100 may be embedded in the wall of the aspiration catheter 400.

In various embodiments of the disclosure, it is envisioned that the aspiration catheter 400 may be configured to establish laminar fluid flow in the distal to proximal direction and that the catheter 100 may configured to establish laminar fluid flow in the proximal to distal direction. It is also envisioned that the flow rate of fluid in the aspiration catheter 400 and/or the microcatheter 100 may be described by Poiseuille's Law:

Volume Flowrate=(Pressure difference×radius4)/(8/π×viscosity×length).

FIG. 7B illustrates an embodiment of the disclosure in which the aspiration catheter 400 includes the aforementioned balloon 430.

FIG. 7C illustrates an alternate embodiment of the aspiration catheter 400, which is identified by the reference character 900. The aspiration catheter 900 is substantially similar (if not identical to) the aspiration catheter 400 and, as such, will only be discussed with respect to any differences therefrom in the interest of brevity.

Although shown as being including (generally) circular outer and inner transverse cross-sectional configurations, it should be appreciated that the particular configuration of the aspiration catheter 900 may be varied without departing from the scope of the present disclosure. For example, it is envisioned that the aspiration catheter 900 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the aspiration catheter 900 may be circular and that the inner transverse cross-sectional configuration of the aspiration catheter 900 may be non-circular. It is also envisioned that the outer transverse cross-sectional configuration of the aspiration catheter 900 may be non-circular and that the inner transverse cross-sectional configuration of the aspiration catheter 900 may be circular.

The aspiration catheter 900 includes a body 902 that defines respective inner and outer walls 904, 906. A first luminal space 908 is defined by the inner wall 904 and a second luminal space 910 is defined between the walls 904, 906.

It is envisioned that the aspiration catheter 900 and the catheter 100 may be configured such that catheter 100 is positionable (positioned) within the second luminal space 910. In such embodiments, it is envisioned that the catheter 100 may be sealed within the second luminal space 910 (at a distal end 912 thereof).

It is envisioned that the microcatheter 100 may span an entire length of the second luminal space 910 or only a portion thereof.

It is envisioned that the second luminal space 910 may be continuous with the luminal space 102 (FIG. 3) defined by the catheter 100. Alternatively, it is envisioned that the luminal spaces 102, 910 may be discreate (distinct) from one another.

It is envisioned that, in certain embodiments, fluid may be introduced into the second luminal space 910 via an opening at a proximal end 912 of the aspiration catheter 900 and communicated distally into the blood vessel V (FIG. 3) through the catheter 100. During such use, it is envisioned that the first luminal space 908 may simultaneously aspirate fluid (e.g., in the distal to proximal direction). It is envisioned that, as fluid flows through the second luminal space 910 (e.g., in the distal to proximal direction), the fluid may funnel to one side into the luminal space 102 of the catheter 100.

In certain embodiments, it is envisioned that the catheter 100 may be disposed within the second luminal space 910 and that the catheter 100 may be adapted to communicated fluid therethrough in the proximal to distal direction.

In certain embodiments, it is envisioned that the aspiration catheter 900 may include one or more of the aforementioned inflatable members 430 (FIG. 7B). In such embodiments, it is envisioned that the inflatable member(s) 430 may be in communication with the first luminal space 908 such that fluid is flowable through the first luminal space 908 and into the inflatable member(s) 430 to facilitate expansion thereof (e.g., from a location outside the patient's blood vessel V (FIG. 3)). In such embodiments, it is envisioned that the aspiration catheter 900 may be configured to inhibit (if not entirely prevent) flow between the respective first and second luminal spaces 908, 910 (e.g., such that the first luminal space 908 is separate and discrete from the second luminal space 910) to facilitate aspiration of the blood vessel V through the second luminal space 910.

In certain embodiments, it is envisioned that the inflatable member(s) 430 may be inflated and deflated via the communication of fluid through one or more additional lumens. In such embodiments, it is envisioned that the additional lumen(s) may extend within the second luminal space 910 or that the additional lumen(s) and the second luminal space 910 may be formed discretely (e.g., such that the additional lumen(s) extend in (generally) parallel relation to the second luminal space 910).

As seen in FIG. 7D, in certain embodiments, it is envisioned that the aspiration catheter 900 may include a plurality of dividers (e.g., septums) 914 extending between the respective inner and outer walls 904, 906 to separate the second luminal space 910 into two or more discrete chambers (spaces, compartments) 916. It is envisioned that the dividers 914 and the chambers 916 may span the entire length of the aspiration catheter 900 or only a portion thereof.

In the particular embodiment seen in FIG. 7D, the aspiration catheter 900 includes first and second dividers 914i, 914ii that separate the second luminal space 910 into first and second chambers 916i, 916ii, respectively. It should be appreciated, however, that the number of dividers 914 and chambers 916 may be increased in alternate embodiments without departing from the scope of the present disclosure.

It is envisioned that one of the chambers 916 (e.g., the first chamber 916i) may be in fluid communication with the luminal space 102 of the catheter 100 and that another chamber 916 (e.g., the second chamber 916ii) may be in fluid communication with the balloon(s) 430 (FIG. 7B).

FIG. 7E illustrates an alternate embodiment of the disclosure in which the aspiration catheter 900 includes a plurality of dividers (e.g., septums) 918 that extend inwardly from the inner wall 904 so as to separate the first luminal space 908 into two or more discrete chambers (spaces, compartments) 920. It is envisioned that the dividers 918 and the chambers 920 may span the entire length of the aspiration catheter 900 or only a portion thereof.

In the particular embodiment seen in FIG. 7E, the aspiration catheter 900 includes respective first, second, and third dividers 918i, 918ii, 918iii that separate the first luminal space 908 into first, second, and third chambers 920i, 920ii, 920iii, respectively. It should be appreciated, however, that the number of dividers 918 and chambers 920 may be increased in alternate embodiments without departing from the scope of the present disclosure.

It is envisioned that one of the chambers 920 (e.g., the first chamber 920i) may be in fluid communication with the luminal space 102 of the catheter 100 and that another chamber 920 (e.g., the second chamber 920ii) may be in fluid communication with the balloon(s) 430 (FIG. 7B).

In certain embodiments of the disclosure, it is envisioned that the aspiration catheter 900 may include a Y-connector having two luer locks that are configured to connect two or more of the aforedescribed chambers (see, e.g., FIGS. 7C, 7D, 7E, 7J) to facilitate simultaneous aspiration and irrigation (e.g., through separate chambers). In such embodiments, it is envisioned that the separate (aspiration and irrigation) chambers may merge together at an external location to allow for selection of the path of fluid flow.

In certain embodiments, it is envisioned that one or more of the chambers may be bounded by a single structure at the distal end thereof (see, e.g., FIGS. 7C, 7D, 7E, 7J) and adapted to be inserted into the blood vessel V (FIG. 3), while each chamber diverges into separate branches defined by separate structures at the proximal end thereof, each of which remains external of the blood vessel V and may be connected to separate luer locks.

It is envisioned that the chambers described herein may be configured for use in different capacities. For example, it is envisioned that the chambers may be adapted to facilitate inflation of the balloon 430 (FIG. 7B), to communicate contrast media through, for aspiration, for irrigation, etc. To facilitate such differing use, it is envisioned that each chamber may be connected to a luer lock.

With reference to FIGS. 7F to 7I, an endovascular system is shown that includes an aspiration catheter (aspirator) 800 that is configured to capture emboli during procedures in which blood flows in the proximal direction (e.g., from a distal (front) end 802 of the aspiration catheter 800 towards a proximal (rear) end 804 of the aspiration catheter 800). In certain embodiments of the disclosure, it is envisioned that the 800 may into the patient To facilitate the capture of emboli, it is envisioned that the distal end 802 of the aspiration catheter 800 may include a flared (e.g., funnel-shaped) configuration that extends radially outward (e.g., to guide emboli into the aspiration catheter 800 and facilitate removal thereof). It is envisioned that the distal end 802 of the aspiration catheter 800 may define a maximum transverse cross-sectional dimension (e.g., a diameter) that exceed a corresponding transverse cross-sectional dimension (e.g., a diameter) defined by the proximal end 804 by (approximately) 10% to (approximately) 1000%. Embodiments in which the (maximum) transverse cross-sectional dimension defined by the distal end 802 may lie outside the disclosed range, however, would not be beyond the scope of the present disclosure. For example, it is envisioned that the maximum transverse cross-sectional dimension defined by the distal end 802 of the aspiration catheter 800 may exceed the corresponding transverse cross-sectional dimension defined by the proximal end 804 by more than 1000%.

It is envisioned that the distal end 804 may expand radially in a continuously increasing manner such that the distal end 804 includes an arcuate outer wall 808 that results in a (generally) concave configuration, as seen in FIG. 7F, or a (generally) convex configuration, as seen in FIG. 7I. It is also envisioned that the outer wall 808 may be (generally) linear in configuration, as seen in FIG. 7H.

It is envisioned that the transverse cross-sectional configuration defined by the distal end 804 of the aspiration catheter 800 may be either constant or variable. For example, it is envisioned that the distal end 804 may be enlarged (e.g., subsequent to insertion into the blood vessel V (FIG. 3)) in response to body temperature and/or via the inflation of a balloon (or other such inflatable or expandable member), which may be supported on (e.g., connected or attached to) either the outer wall 808 or an inner wall 810 or embedded within the distal end 804. It is also envisioned that the distal end 804 may be configured for retraction into the body 806 of the aspiration catheter 800. In such embodiments, it is envisioned that the distal end 804 may include (e.g., may be formed partially or entirely from) a flexible (e.g., resilient) material to facilitate (automatic) expansion (e.g. opening) upon exposure from the body 806 and collapse (e.g., closure) during retraction into the body 806. Additionally, or alternatively, it is envisioned that the aspiration catheter 800 may include a closure mechanism (e.g., a lasso or the like that extend about a periphery of the distal end 804) to facilitate collapse of the distal end 804.

Although shown as being including (generally) circular outer and inner transverse cross-sectional configurations, it should be appreciated that the particular configuration of the aspiration catheter 800 may be varied without departing from the scope of the present disclosure. For example, it is envisioned that the catheter 800 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the catheter 800 may be circular and that the inner transverse cross-sectional configuration of the catheter 800 may be non-circular. It is also envisioned that the outer transverse cross-sectional configuration of the catheter 800 may be non-circular and that the inner transverse cross-sectional configuration of the catheter 800 may be circular.

It is envisioned that the distal end 804 may be formed either integrally with a body 806 of the aspiration catheter 800 (e.g., such that the distal end 804 extends continuously from the body 806) or that the distal end 804 and the body 806 may be formed as separate, discrete structures. In such embodiments, it is envisioned that the distal end 804 may be either fixedly or removably connected to the body 806 in any suitable manner using any suitable structures, components, and/or mechanisms (e.g., an adhesive and/or one or more mechanical fasteners such as pins, screws, clips, clamps, or the like).

It is envisioned that the distal end 804 of the aspiration catheter 800 may include a solid construction (e.g., so as to obstructs blood flow), as seen in FIG. 7F. It is also envisioned, however, that the distal end 804 of the aspiration catheter 800 may be configured for allow blood to flow therethrough such that the distal end 804 acts a filter element (e.g., in a manner similar or identical to the filter element 395 (FIG. 5) discussed above). For example, it is envisioned that the distal end 804 may include (e.g., may be formed partially or entirely from) a mesh (or mesh-like) material, as seen in FIG. 7G and that the distal end 804 may be either permeable or semi-permeable in configuration. Configuring the distal end 804 of the aspiration catheter 800 so as to permit blood flow therethrough facilitates the application of intermittent aspiration (e.g., as opposed to continuous aspiration) to remove debris, etc.

During the course of an endovascular (surgical) procedure, it is envisioned that the ratio between flow and flow obstruction can be monitored using any suitable method or instrumentation including, for example, via intermittent contrast venography, via transabdominal ultrasound, etc. In certain embodiments of the disclosure, it is envisioned that IVUS may be incorporated into the aspiration catheter 800 (e.g., the distal end 804) to facilitate continuous monitoring of the blood flow, thereby obviating the need for contrast, radiation, or an additional (second) technician to perform transabdominal ultrasound. By way of nonlimiting example, the following methodology may be employed in the context of a patient with a large left Iliac Vein thrombus. Initially, venous access can be obtained via the left Femoral Vein and separately through either Internal Jugular Vein in the neck. At the jugular vein, the aspiration catheter 800 (including IVUS) can be advanced and deployed in the upper Inferior Vena Cava such that the distal end 804 faces inferiorly to facilitate the capture of debris during blood venous flow (e.g., from the patient's leg towards the patient's heart). A treatment device (e.g., the wire 200 (FIG. 4), the macerating irrigation catheter 300 (FIG. 5), or any other such suitable device described herein) may then be inserted and advanced from the left femoral vein access across a blockage B (FIG. 3) (e.g., a clot) in the left iliac vein. In such methods of use, it is envisioned that the treatment device may be inserted either through the aspiration catheter 800 or that the treatment device may be advanced externally of the aspiration catheter 800, either in the same direction or in an opposite direction. The IVUS (e.g., at the distal end 804 of the aspiration catheter 800) can then be used to monitor flow in the patient's upper IVC. To reduce (e.g., minimize) blood loss, aspiration may be postponed until some diminution of flow and buildup of debris is observed. The blockage B can thereafter be treated using the treatment device (e.g., to agitate and/or fragment the blockage B) to restore flow in the iliac vein, during which, debris is captured by the distal end 804 of the aspiration catheter 800. Aspiration can then be applied (e.g., intermittently) as needed to reduce (e.g., minimize) blood loss. In some cases, an additional treatment device (with or without an irrigating element or functionality), can be advanced directly through the aspiration catheter 800 to further agitate, break up, macerate, or otherwise fragment the blockage B (and any debris) into smaller pieces when needed to further reduce any likelihood that the aspiration catheter 800 may become clogged. In some cases, it is also envisioned that the treatment device may be advanced through the aspiration catheter 800 without the use of an additional vascular access site.

Additionally, or alternatively, it is envisioned that the aspiration catheter 800 may include a wire extending therethrough (and terminating within the distal end 804) and/or that the aspiration catheter 800 may use technology to create vibrational energy (e.g., in a manner similar or identical to that used in the original version of the Penumbra Apollo device to remove parenchymal blood from the brain) to further agitate, break up, macerate, or otherwise fragment the blockage(s) B (FIG. 3) as they enter the distal end 804 of the aspiration catheter 800 to further reduce any likelihood that the aspiration catheter 800 may become clogged. For example, in one particular embodiment, it is envisioned that the aspiration catheter 800 may include a vibrational wire that is configured (adapted) to cut blockages B and deployed distally from (or within) the body 806.

Additionally, or alternatively, as discussed below, it is envisioned that a rotational macerating element and/or a high-pressured irrigation element may be incorporated into (or used with) the aspiration catheter 800 (e.g., to break up the blockage B (FIG. 3) as pieces of blockage B enter the aspiration catheter 800 to avoid occlusions within the aspiration catheter 800). With reference now to FIG. 8, an endovascular system is shown that includes an aspiration catheter 1000 with a distal end 1002 that supports (e.g., is attached, connected to) a filter element 1004 (e.g., a semipermeable membrane, a net, a mesh, or other such structure suitable for the intended purpose of capturing emboli (e.g., debris) while allowing blood cells, serum, etc., to pass therethrough in a (substantially) unimpeded manner), which may be similar or identical in construction to the aforedescribed filter element 395 (FIG. 5).

Although shown as being including (generally) circular outer and inner transverse cross-sectional configurations, it should be appreciated that the particular configuration of the aspiration catheter 1000 may be varied without departing from the scope of the present disclosure. For example, it is envisioned that the aspiration catheter 1000 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the aspiration catheter 1000 may be circular and that the inner transverse cross-sectional configuration of the aspiration catheter 1000 may be non-circular. It is also envisioned that the outer transverse cross-sectional configuration of the aspiration catheter 1000 may be non-circular and that the inner transverse cross-sectional configuration of the aspiration catheter 1000 may be circular.

In the particular embodiment illustrated, the filter element 1004 includes a proximal end 1005a that is directly attached to the distal end 1002 of the aspiration catheter 1000 (e.g., such that the filter element 1004 is circumferentially positioned about a distal end hole thereof) and a free distal end 1005b. The free distal end 1005b of the filter element 1004 includes a flared (e.g., funnel-shaped) configuration and a distal edge 1006 that defines a transverse cross-sectional dimension (e.g., a diameter) greater than that defined by more proximal portions of the filter element 1004. It is envisioned that the filter element 1004 may be configured such that the transverse cross-sectional dimension defined by the distal edge 1006 substantially approximates (if not exceeds) an internal transverse cross-sectional dimension defined by the blood vessel V (FIG. 3) such that any blood passing through the blood vessel V is directed into and through the filter element 1004. For example, it is envisioned that the transverse cross-sectional dimension defined by the distal edge 1006 of the filter element 1004 may exceed a corresponding transverse cross-sectional dimension (e.g., a diameter) defined by the aspiration catheter 1000 by (approximately) 10% to (approximately) 5000%. Embodiments in which the transverse cross-sectional dimension defined by the distal edge 1006 of the filter element 1004 may lie outside the disclosed range, however, would not be beyond the scope of the present disclosure. For example, it is envisioned that the transverse cross-sectional dimension defined by the distal edge 1006 of the filter element 1004 may exceed the corresponding transverse cross-sectional dimension defined by the aspiration catheter 1000 by more than 5000%.

As seen in FIGS. 11A 11B, 12A, 12B, and 13, for example, it is envisioned that the filter element 1004 may include (e.g., may be formed partially or entirely from) a mesh (or mesh-like) material, such as a net, to facilitate the capture of emboli (e.g., debris resulting from agitation, break up, maceration, or other such fragmentation of a blockage B (FIG. 3)). For example, it is envisioned that the filter element 1004 may be configured to capture emboli (e.g., particulate) having a dimension (e.g., a maximum cross-sectional dimension) that lies substantially within the range of (approximately) 10 µm to (approximately) 500 µm. Embodiments in which the filter element 1004 may be configured to capture emboli having a cross-sectional dimension that may lie outside the disclosed range, however, would not be beyond the scope of the present disclosure. For example, it is envisioned that the filter element 1004 may be configured to capture emboli having a cross-sectional dimension smaller than 10 µm and/or larger than 500 µm.

Figure 16:
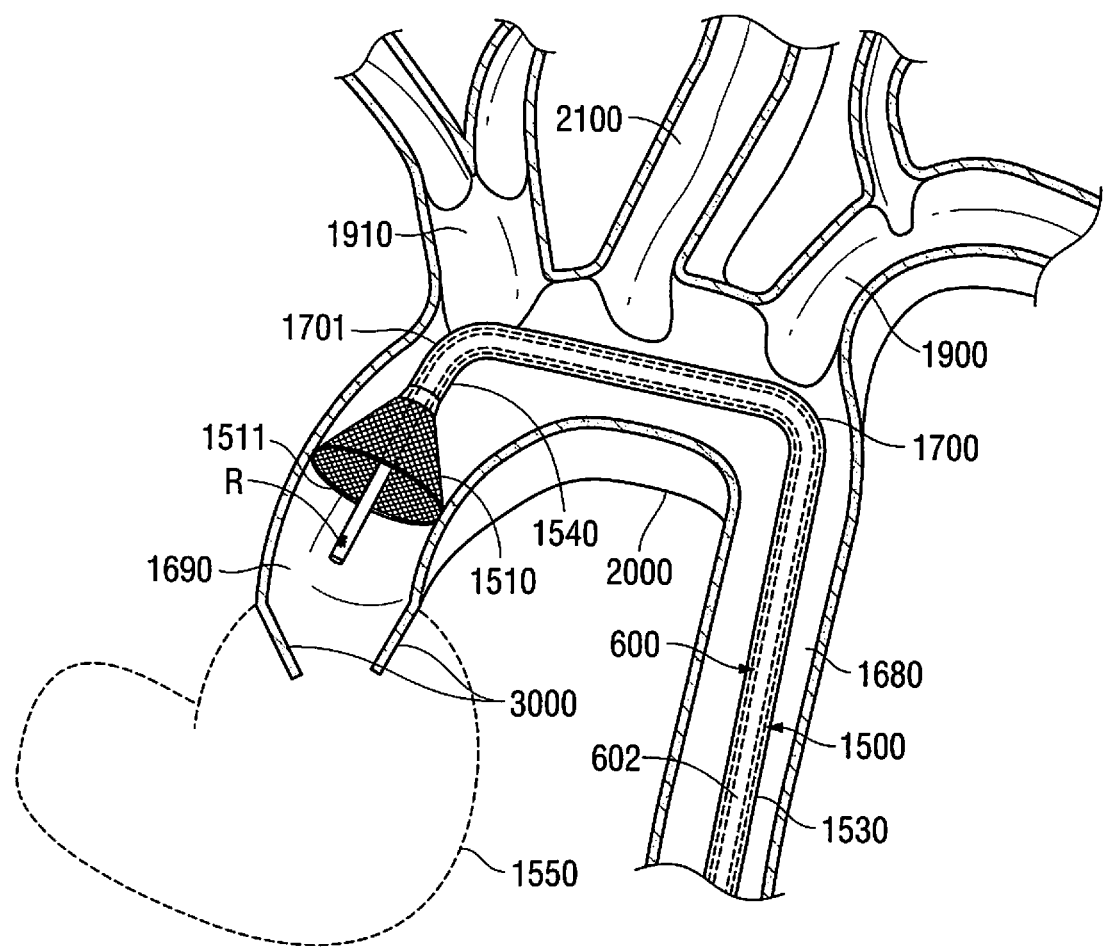
FIG. 16 shows a cross section side view illustrating the introduction of a filtered-tip aspiration and/or delivery catheter within the aorta via an outer sheath/member.

The aspiration catheter 1000 may further include a retainer (retention member) 1008 that is configured to maintain the filter element 1004 in a collapsed (non-expanded, compressed, closed) configuration. The retainer 1008 may be either rigid, semi-rigid, or flexible in construction and is supported by (e.g., is connected to) a (central) tube 1010. Alternatively, as illustrated in FIG. 16, it is envisioned that an outer (delivery) catheter (sheath) 1530 may be used to maintain the collapsed configuration of the filter element 1004.

In the particular embodiment of the disclosure seen in FIG. 8, the retainer 1008 includes a plurality of wings 1012 (the number of which may vary in alternate embodiments of the disclosure) that extend radially outward from the tube 1010. It is envisioned that the wings 1012 may be arranged in non-contacting relation so as to define gapping therebetween such that the retainer 1008 only partially encloses the filter element 1004. As seen in FIG. 8, however, it is also envisioned that the wings 1012 may be arranged in contacting relation so as to eliminate any gapping between adjacent wings 1012. In such configurations, the retainer 1008 is configured as a skirt 1014 defining an interior space 1016 that is configured to accommodate and completely enclose the filter element 1004 (e.g., in the collapsed configuration).

It is envisioned that the retainer 1008 and the tube 1010 may be removed from the blood vessel V (FIG. 3) by withdrawing the retainer 1008 and the tube 1010 through the (percutaneous) opening and along the length of the aspiration catheter 1000. To facilitate such removal, it is envisioned that retainer 1008 (e.g., the skirt 1014) may include a distal edge 1018 defining a transverse cross-sectional dimension (e.g., a diameter) that is less than the inner diameter of the aspiration catheter 1000.

It is envisioned that the tube 1010 and the retainer 1008 (e.g., the wings 1012) may be advanced in a direction away from the aspiration catheter 1000 and the filter element 1004 by an introducer 1020 (also referred to herein as an engagement member) that is movable independently of the tube 1010 and the aspiration catheter 1000. It is envisioned that the introducer 1020 may be configured such that the tube 1010 extends therethrough (e.g., to allow for independent movement along the length of the tube 1010). It is also envisioned that the introducer 1020 may be configured to advance (e.g., push) the tube 1010 and the retainer 1008 away from the filter element 1004 to expose the filter element 1004 from the retainer 1008, thereby releasing the constraint applied by the retainer 1008 and allowing for expansion of the filter element 1004. For example, the introducer 1020 may be configured as an inner catheter that is positionable within the aspiration catheter 1000 to facilitate delivery thereof. It is envisioned that the introducer 1020 may be removable (e.g., such that the introducer 1020 is separable from the tube 1010 and the aspiration catheter 1000) by axially withdrawing the introducer (e.g., along the length of the tube 1010 and the aspiration catheter 1000). It is also envisioned that the tube 1010, the retainer 1008, and the introducer 1020 may be unitarily formed so as to define an outer sheath through which the aspiration catheter 1000 may be advanced. In certain embodiments, it is envisioned that the introducer 1020 may be removed prior to introducing the aspiration catheter 1000 and the filter element 1004.

In certain embodiments, it is envisioned that the tube 1010 may extend proximally beyond the proximal end of the aspiration catheter 1000 and that tube 1010 may be directly advanced relative to aspiration catheter 1000 in order to expose the filter element 1004 and thereby release the filter element 1004 from the constraint provided by the retainer 1008 such that the filter element 1004 expands. It is envisioned that the filter element 1004 may be self-expanding such that the filter element 1004 automatically expands upon exposure from the retainer 1008 or, alternatively, that the filter element 1004 may require actuation (e.g., manual manipulation) to expand.

It is envisioned that the introducer 1020 may include an outer transverse cross-sectional dimension (e.g., a diameter) that is (approximately) equal to an inner transverse cross-sectional dimension (e.g., a diameter) of the aspiration catheter 1000. It is also envisioned that the outer transverse cross-sectional dimension of the introducer 1020 may lie substantially within the range of (approximately) 95% to (approximately) 1% of the inner transverse cross-sectional dimension of the aspiration catheter 1000. Percentages that may lie outside the disclosed range, however, would not be beyond the scope of the present disclosure.

FIGS. 8A, 8B illustrates an alternate embodiment of the disclosed endovascular system that includes respective first and second members 1050, 1060, which are configured for independent axial (longitudinal) movement in relation to each other. In the illustrated embodiment, the first member 1050 includes the aspiration catheter 1000 and the second member 1060 includes the retainer 1008 and the tube 1010.

During use, the first member 1050 and the second member 1060 are approximated such that the retainer 1008 (e.g., the wings 1012) contacts (engages) the filter element 1004 on the aspiration catheter 1000 to facilitate reconfiguration of the filter element 1004 from the expanded configuration (FIG. 8A) into the collapsed configuration (FIG. 8B). More specifically, the second member 1060 is moved in a first direction 1 (e.g. towards the first member 1050) and/or the first member 1050 is moved in a second direction 2 (e.g., towards the second member 1060), which is opposite to the first direction 1, whereby the filter element 1004 is received by, and collapsed within, the interior space 1016 defined by the retainer 1008.

To facilitate approximation of the respective first and second members 1050, 1060 in the manner described, it is envisioned that the second member 1060 may be configured for insertion into the first member 1050. More specifically, it is envisioned that the tube 1010 may define an outer transverse cross-sectional dimension (e.g., a diameter) less than an inner transverse cross-sectional dimension (e.g., a diameter) defined by the aspiration catheter 1000 such that the tube 1010 is receivable within the aspiration catheter 1000 during reconfiguration of the filter element 1004 into the collapsed configuration, as seen in FIG. 8B.

In certain embodiments, it is envisioned that the introducer 1020 may be employed to facilitate reconfiguration of the filter element 1004 via independent axial (longitudinal) movement in relation to each of the respective first and second members 1050, 1060. For example, it is envisioned that the introducer 1020 may be configured for contact (engagement) with the second member 1060 (e.g. the tube 1010) to advance the retainer 1008 towards the filter element 1004 (in the first direction 1), as seen in FIG. 8A. It is also envisioned that the introducer 1020 may be utilized to separate the retainer 1008 from the filter element 1004 by moving the retainer 1008 and the tube 1010 away from the filter element (in the second direction 2), as seen in FIG. 8B. To facilitate such use, it is envisioned that the introducer 1020 may be configured for removable insertion into the aspiration catheter 1000 (e.g., it is envisioned that the introducer 1020 may include an outer transverse cross-sectional dimension (e.g., a diameter) that is less than the inner transverse cross-sectional dimension defined by the aspiration catheter 1000.

While it is envisioned that the introducer 1020 may include a (generally) circular outer and inner transverse cross-sectional configurations, as seen in FIG. 8B, it should be appreciated that the particular configuration of the introducer 1020 may be varied without departing from the scope of the present disclosure. For example, it is envisioned that the introducer 1020 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the introducer 1020 may be circular and that the inner transverse cross-sectional configuration of the introducer 1020 may be non-circular. It is also envisioned that the outer transverse cross-sectional configuration of the introducer 1020 may be non-circular and that the inner transverse cross-sectional configuration of the introducer 1020 may be circular.

Mechanisms for Retracting the Filter-Magnetic System and Ring Sheath System

Figure 10A:
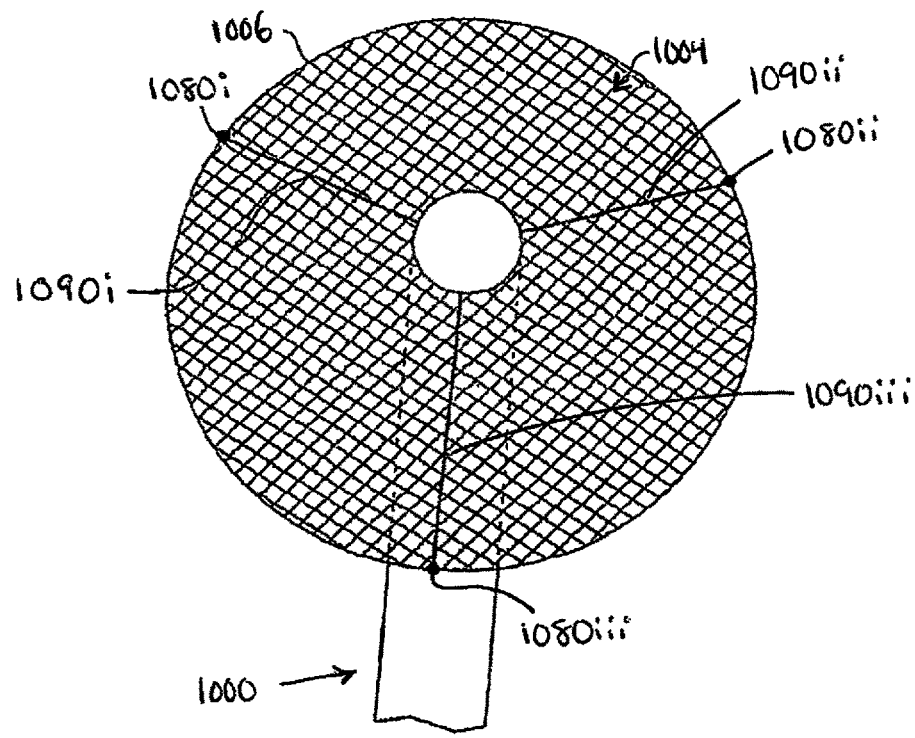
FIG. 10A shows a perspective view of one embodiment of the endovascular device (system) of the present disclosure.
Figure 10C:
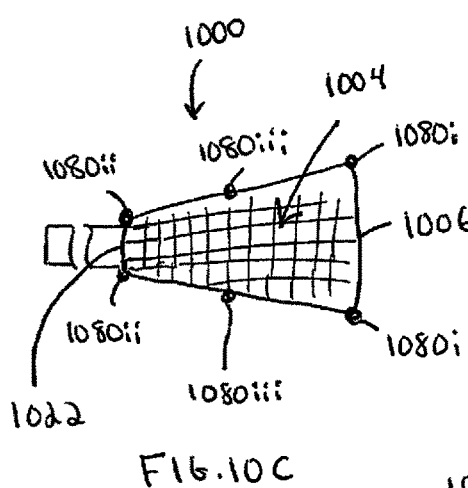
FIG. 10C shows a side, plan view of one embodiment of the endovascular device (system) of the present disclosure.
Figure 10B:
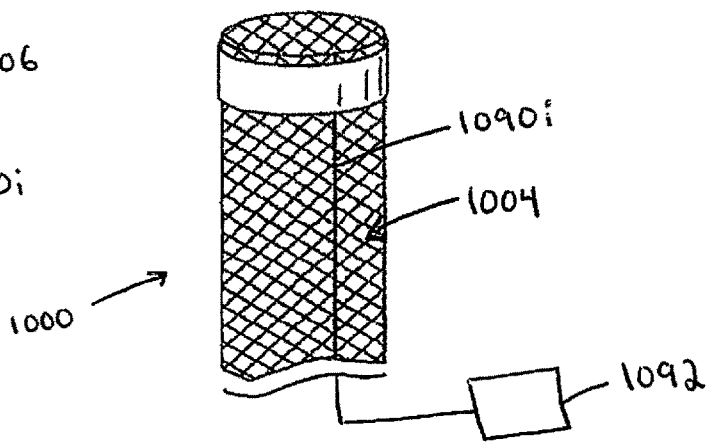
FIG. 10B shows a perspective view of one embodiment of the endovascular device (system) of the present disclosure.

With reference to FIGS. 10A, 10B, in certain embodiments of the disclosure, it is envisioned that the filter element 1004 may be configured for collapse (compression) such that the transverse cross-sectional dimensioned defined by the distal edge 1006 less than (or equal to) the inner transverse cross-sectional dimensioned defined by the aspiration catheter 1000 (e.g., such that no part of the filter element 1004 defines a transverse cross-sectional dimension that exceeds the inner transverse cross-sectional dimension of the aspiration catheter 1000). To facilitate movement of the filter element 1004 from the expanded (e.g., open) configuration (FIG. 10A) into the collapsed (e.g., closed) configuration (FIG. 10B), it is envisioned that the aspiration catheter 1000 may include one or more magnet components 1080 (e.g., solenoids) that area supported on (e.g., attached, connected to) the distal edge 1006 of the filter element 1004 (or any other suitable location). The magnet component(s) 1080 are connected to one or more wires 1090 that extend along the axial (longitudinal) length of the aspiration catheter 1000 to a power source 1092 that is located externally of the patient.

In the particular embodiment illustrated in FIGS. 10A, 10B, the aspiration catheter 1000 includes (first, second, and third) magnetic components 1080*i*, 1080*ii*, 1080*iii* are connected to (first, second, and third) wires 1090*i*, 1090*ii*, 1090*iii* respectively, each of which includes (e.g., is formed partially or entirely from) one or more electrically conductive materials. Embodiment are also envisioned, however, in which one or more of the magnetic components 1080 may include a ferromagnetic metal that is not associated with a corresponding wire 1090.

While the aspiration catheter 1000 is illustrated as including three magnetic components 1080 that are separated by a (generally) equivalent angular distance of (approximately) 120 degrees, it should be appreciated that the number and/or the particular location of the magnetic components 1080 may be varied in alternate embodiments without departing from the scope of the present disclosure. For example, it is envisioned that the number of magnetic components 1080 may be increased or decreased and that the (angular) spacing between adjacent magnetic components 1080 may be non-equivalent.

To create attraction between the magnetic components 1080 and thereby collapse the filter element 1004, the wire(s) 1090 may be coiled around a ferromagnetic metal so as to produce a magnetic field upon the passage of current therethrough. In the particular embodiment illustrated, for example, the wire 1090*i* is configured as an insulated copper wire that is wrapped around the magnetic component 1080*i*, which includes a ferromagnetic metal bar (either (generally) linear or non-linear (e.g., curved) in configuration) and the magnetic components 1080*ii*, 1080*ii* each include a ferromagnetic metal. During use, when current is passed through the wire 1090*i*, a magnetic field is produced around the magnetic component 1080*i*, which attracts the magnetic components 1080*ii*, 1080*iii*. It is envisioned that the magnetic components 1080 may be configured such that the magnetic force of attraction created is sufficient to overcome any intrinsic resistance of the filter element 1004 to collapse.

In certain embodiments, it is envisioned that the aspiration catheter 1000 may include magnetic components 1080 with solenoids having magnetic poles that are arranged in (generally) parallel relation to an exterior surface of the filter element 1004. For example, the aspiration catheter 1000 may include a (first) magnetic component 1080*i* with a first solenoid and a (second) magnetic component 1080*ii* with a second solenoid that is arranged in generally opposite relation to the (first) magnetic component 1080*i* such that, upon the passage of current through the corresponding (coiled) wires 1090*i*, 1090*ii*, resulting magnetic fields are generated with opposing poles across the filter element 1004 (e.g., such that the North pole of the first magnetic component 1080*i* is oriented in opposing relation to the South pole of the second magnetic component 1080*ii* and the South pole of the first magnetic component 1080*i* is oriented in opposing relation to the North pole of the second magnetic component 1080*ii*), thereby causing attraction of the magnetic components 1080*i*, 1080*ii* and collapse (closure) of the filter element 1004.

In certain embodiments, it is envisioned that the magnetic components 1080 (e.g., the solenoids) may be arranged so that the opposing poles thereof are arranged in (generally) perpendicular relation to the filter element 1004. For example, the magnetic components 1080*i*, 1080*ii* may include respective first and second solenoids that are arranged in (generally) perpendicular relation to the filter element 1004 and in (generally) opposing relation to each other (e.g., such that the magnetic components 1080*i*, 1080*ii* are spaced from each other by an angular distance of (approximately) 180 degrees) such that the North pole of the magnetic component 1080*i* and the South pole of the magnetic component 1080*ii* are oriented inwardly (e.g., towards each other and a center of the filter element 1004).

In certain embodiments, it is envisioned that the aspiration catheter 1000 may include a plurality of magnetic components 1080 that are positioned in a variety of axial (longitudinal) positions (e.g. along the length of the filter element 1004). For example, as seen in FIG. 10C, it is envisioned that aspiration catheter 1000 may include a first pair of magnetic components 1080*i* that are located on (or adjacent to) the distal edge 1006 of the filter element 1004, a second pair of magnetic components 1080*ii* that are located on (or adjacent to) a proximal end (edge) 1022 of the filter element 1004, and a third pair of magnetic components 1080*iii* that are located between the pairs of magnetic components 1080*i*, 1080*ii*. In various alternate embodiments, it is envisioned that the axial spacing between adjacent magnetic components 1080 may be either (approximately) equal or unequal. For example, it is envisioned that the axial spacing between the magnetic components 1080*i*, 108*iii* may be less than or greater than the axial spacing between the magnetic components 1080*ii*, 108*iii*.

It is envisioned that the magnetic components 1080 may arranged to facilitate folding of the filter element 1004 into any desired configuration (e.g., such that, upon collapse, no part of the filter element 1004 extends beyond the aspiration catheter 1000).

During use of the aspiration catheter 1000, it is envisioned that the filter element 1004 may be introduced into the blood vessel V (FIG. 3) in the collapsed configuration (via the magnetic fields generated by the magnetic components 1080). When positioned as desired within the blood vessel V, the magnetic fields may be deactivated (e.g., by terminating current flow through the wires 1090) to allow for the (automatic) expansion of the filter element 1004 (e.g., via the intrinsic resiliency thereof) into the flared (e.g., funnel-shaped) configuration discussed above.

When collapse of the filter element 1004 is necessary or desired (e.g., to facilitate repositioning of the aspiration catheter 1000 within the blood vessel V (FIG. 3) or removal of the aspiration catheter 1000 from the blood vessel V), the collapsed configuration of the filter element 1004 can be restored via reactivation of the magnetic fields (e.g., by initiating current flow through the wires 1090).

FIGS. 11A, 11B illustrate an alternate embodiment of the aspiration catheter 1000 in which the expansion and collapse of the filter element 1004 is regulated by a ring structure 1024. The ring structure 1024 may be either rigid, semi-rigid, or flexible in construction and may be supported in any suitable location. For example, in the illustrated embodiment, the ring structure 1024 is located externally of the filter element 1004.

It is envisioned that the filter element 1004 may be connected to the aspiration catheter 1000 proximally of (e.g., below) the ring structure 1024.

It is envisioned that the ring structure 1024 may be advanced distally from the aspiration catheter 1000, thereby forcing the filter element 1004 to collapse.

It is envisioned that the ring structure 1024 may be connected to a stiff wire 1026 (or other such suitable member) such that the ring structure 1024 may be advanced distally from the aspiration catheter 1000 via the application of force to the stiff wire 1026 out of the aspiration catheter to surround and collapse the filter element 1004. In certain embodiments, it is envisioned that the stiff wire 1026 may extend through the wall of the aspiration catheter 1000.

In certain embodiments, it is envisioned that the filter element 1004 may be attached (connected) to an inside surface of the aspiration catheter 1000 (e.g., at the distal end 1002 thereof) and that the ring structure 1024 may be configured to contact (engage) the distal end 1002 of the aspiration catheter 1000 in abutting relation (e.g., such that the ring structure 1024 constitutes an extension of the aspirating catheter 1000).

It is envisioned that the ring structure 1024 may define a transverse cross-sectional dimension (e.g., a diameter) that (generally) approximates that defined by the distal end 1002 of the aspiration catheter 1000 so as not to impede aspiration by reducing the transverse cross-sectional area at the distal end 1002 of the aspiration catheter 1000.

Figure 12A:
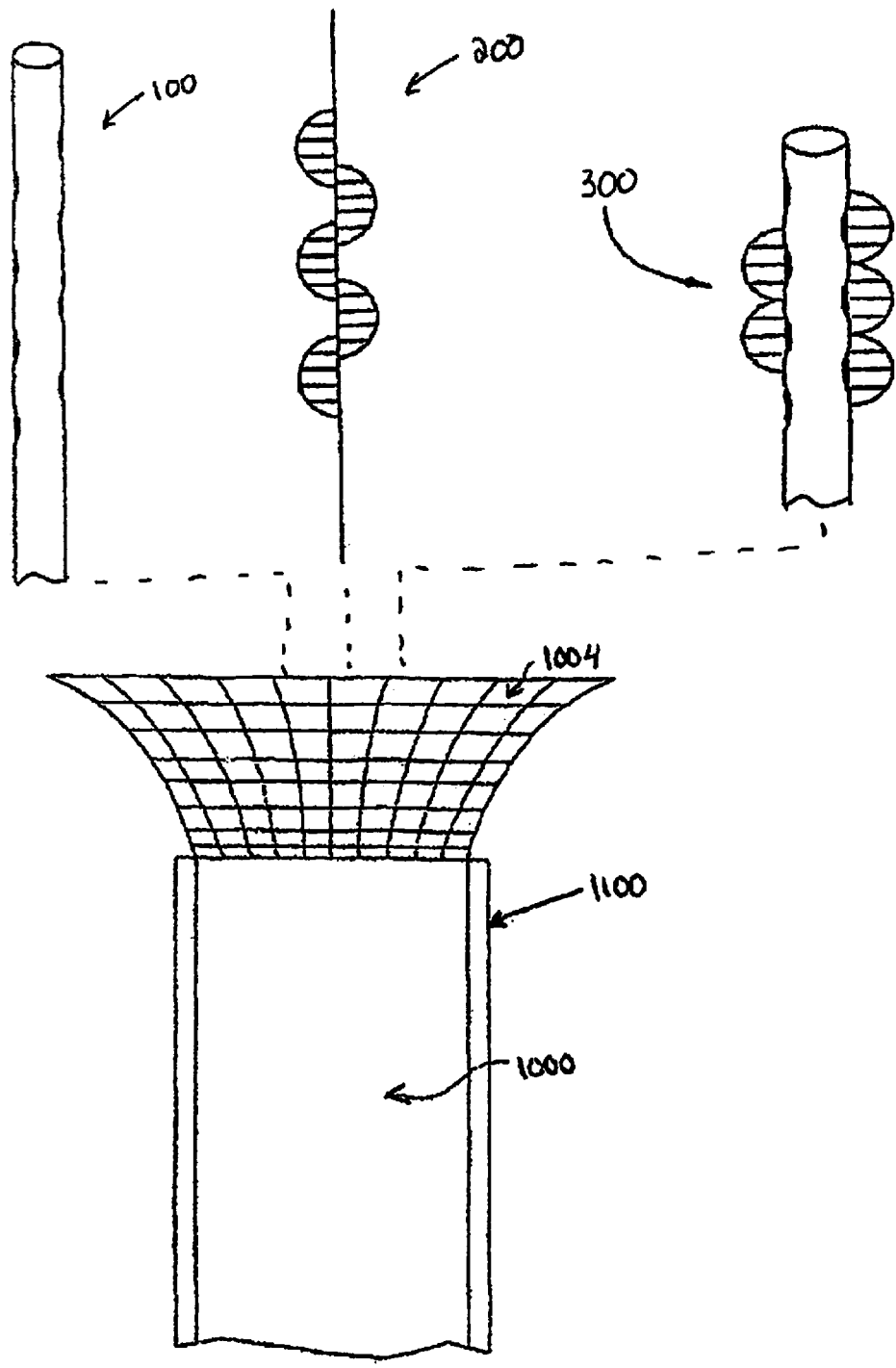
FIG. 12A shows a cross section side view of one embodiment of the endovascular device (system) of the present disclosure.

In certain embodiments of the disclosure, it is envisioned that the endovascular system may further include an outer (delivery) catheter (sheath) 1100 defining an internal space (e.g., a lumen) that is configured to receive the aspiration catheter 1000 and the filter element 1004, as seen in FIGS. 12A, 12B, such that the aspiration catheter 1000 and the outer catheter 1100 are axially (longitudinally) movable in relation to each other to deploy, expand, collapse, and withdraw the filter element 1004, which may be directly or indirectly attached (connected) to (or otherwise supported on) the distal end of the aspiration catheter 1000 in the manner described herein. In such embodiments, it is envisioned that the (inner) aspiration catheter 1000 may define an outer transverse cross-sectional dimension (e.g., a diameter) that (generally) approximates an inner transverse cross-sectional dimension (e.g., a diameter) defined by the outer catheter 1100. To reduce any resistance to relative longitudinal movement between the aspiration catheter 1000 and the outer catheter 1100 (e.g., friction therebetween), it is envisioned that the inner transverse cross-sectional dimension (e.g., diameter) defined by the outer catheter 1100 may exceed the maximum outer transverse cross-sectional dimension (e.g., diameter) defined by the aspiration catheter 1000.

Although shown as being including (generally) circular outer and inner transverse cross-sectional configurations, it should be appreciated that the particular configuration of the outer catheter 1100 may be varied without departing from the scope of the present disclosure. For example, it is envisioned that the catheter 1100 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the catheter 1100 may be circular and that the inner transverse cross-sectional configuration of the catheter 1100 may be non-circular. It is also envisioned that the outer transverse cross-sectional configuration of the catheter 1100 may be non-circular and that the inner transverse cross-sectional configuration of the catheter 1100 may be circular.

It is envisioned that the aspiration catheter 1000 and the outer catheter 1100 may be configured to allow for independent relative movement therebetween. For example, it is envisioned that the filter element 1004 may be collapsed by advancing the outer catheter 1100 over the aspiration catheter 1000 and the filter 1004 and/or by retracting the aspiration catheter 1000 and the filter 1004 into the outer catheter 1100.

In certain embodiments, it is envisioned that the outer catheter 1100 may include a rigid (or semi-rigid) construction to facilitate collapse of the filter element 1004 during withdrawal of the aspiration catheter 1000 into the outer catheter 1100 and/or advancement of the outer catheter 1100 over the aspiration catheter 1000.

During use of the aspiration catheter 1000, it is envisioned that the blood vessel V (FIG. 3) (e.g., the vein or the artery including the blockage B that is the target of the endovascular procedure) may be accessed downstream from the blockage B (e.g., in the context of venous thrombi and emboli) such that the aspiration catheter 1000 approaches the blockage B in an upstream direction. Alternate approaches are envisioned as well, however.

In certain embodiments, it is envisioned that the aspiration catheter 1000 and/or the outer catheter 1100 may include, or may be (removably) connected to, an aspiration device (component) such that the aspiration device is located (generally) opposite to the filter element 1004.

It is envisioned that the outer catheter 1100 may be configured for use within any of the treatment devices described herein. For example, FIG. 12A illustrates an exemplary method of use in which the microcatheter 100 extends into the patient (e.g., the blood vessel V (FIG. 3)) through the outer catheter 1100 and the aspiration catheter 1000. It is envisioned, however, that the outer catheter 1100 and the (inner) aspiration catheter 1000 may configured for use with any of the treatment devices described herein for any necessary or desired purpose. For example, it is envisioned that the outer catheter 1100 and the aspiration catheter 1000 may be used in conjunction with the catheter 100 (FIG. 3), the macerating microwire 200 (FIG. 4), the macerating irrigation catheter (hypotube) 300 (FIG. 5), a retrieval mechanism (described below), a heart (or other such) valve (described below), etc., to treat (e.g., agitate, break up, macerate, or otherwise fragment) the blockage B (FIG. 3), extract the blockage B and/or debris, deliver the heart (or other such valve), etc.

Method 1: Irrigation and Maceration Only

The present disclosure contemplates various methods for irrigating and treating (e.g., macerating) a blockage in a patient's blood vessel which may include cells, debris (e.g., cell debris), emboli, or other such material, either exclusively or in combination. For example, one method includes: introducing a rotating, irrigating catheter into the blood vessel; advancing the rotating, irrigating catheter to the site of the blockage; penetrating the blockage with the rotating, irrigating catheter; macerating the blockage by rotating the rotating, irrigating catheter; and irrigating within the blockage (e.g., to facilitate maceration of the blockage and/or inhibit (if not entirely prevent) collapse of the blood vessel). It is also contemplated that irrigation may be performed beyond the blockage as well.

In variations on the disclosed method, it is envisioned: that maceration and irrigation may be constant; that maceration may be constant while irrigation may be intermittent; that maceration may be intermittent while irrigation is constant; that maceration and irrigation may each be intermittent; that maceration and irrigation may occur simultaneously; and that maceration and irrigation may occur asynchronously.

Method 2: Only Irrigation and Aspiration

The present disclosure contemplates various methods of removing a blockage in a patient's blood vessel which may include cells, debris (e.g., cell debris), emboli, or other such material, either exclusively or in combination. For example, one method includes: introducing an irrigating catheter and an aspiration catheter into the blood vessel; advancing the irrigating catheter and the aspirating catheter to the site of the blockage; penetrating the blockage with the irrigating catheter; aspirating the blockage; and irrigating the blockage. It is envisioned that irrigation and aspiration may be utilized, independently of maceration, to reverse blood flow in the blood vessel while maintaining sufficient vascular volume and pressure to inhibit (if not entirely prevent) collapse of the blood vessel.

In variations on the disclosed method, it is envisioned: that aspiration and irrigation may each be constant; that aspiration and irrigation may each be intermittent; that aspiration may be intermittent while irrigation may be constant; that aspiration may be constant while irrigation may be intermittent; that aspiration and irrigation may occur simultaneously; and that aspiration and irrigation may occur asynchronously.

Method 3: Maceration, Irrigation, and Aspiration

The present disclosure contemplates various methods of removing a blockage in a patient's blood vessel, which may include cells, debris (e.g., cell debris), emboli, or other such material, either exclusively or in combination. For example, one method includes: introducing a macerating, irrigating catheter and an aspiration catheter into the blood vessel; advancing the macerating, irrigating catheter and the aspirating catheter to the site of the blockage; penetrating the blockage with the macerating, irrigating catheter; macerating the blockage; irrigating the blockage; and aspirating the blockage.

In variations on the disclosed method, it is envisioned: that aspiration, maceration, and irrigation may be constant; that aspiration, maceration, and irrigation may be intermittent; that aspiration may constant while maceration and irrigation may each be intermittent; that aspiration and maceration may be constant while irrigation may be intermittent; that aspiration and irrigation may be constant while maceration may be intermittent; that irrigation may be constant while maceration and aspiration may be intermittent; that two or more of aspiration, irrigation, and maceration may occur simultaneously; and that two or more of aspiration, irrigation, and maceration may occur asynchronously.

It is envisioned that the macerating, irrigating catheter and/or the aspiration catheter may include one or more inflatable members (e.g., balloons) suitable for the intended purpose of intentionally interrupting blood flow through the blood vessel, either partially or completely (e.g., to facilitate the reversal of blood flow reversal within the blood vessel). It is also envisioned, however, that the macerating, irrigating catheter and/or the aspiration catheter may be devoid of any such inflatable member(s).

( ) uses the combination of substantially occluding the vessel together with aspiration and irrigation creates a flow-reversal circuit that facilitates removal of clot and debris.

Method 4: Using Remotely Placed Filters to Capture Emboli Showers at Sites Distant from the Thrombosis The present disclosure contemplates various methods of removing a blockage in a patient's blood vessel, which may include cells, debris (e.g., cell debris), emboli, or other such material, either exclusively or in combination. For example, one method includes introducing a macerating device, optionally with further irrigating components, and a filter-tipped aspiration catheter into the blood vessel, wherein the filter is positioned downstream from the blockage, so that when clot and debris is freed up, optionally aided by additional irrigation, the normal blood flow will direct the pieces of clot and debris toward the filter, which will capture the clot and debris and allow blood to flow therethrough such that the clot and debris can ultimately be removed from the body by applying aspiration to the aspiration catheter and/or recapturing and removing the filter together with the captured clot and debris. The method may also include advancing the macerating device (including the optional irrigating components) to the site of the blockage, penetrating the blockage with the macerating device, macerating the blockage, (optionally) irrigating the blockage, and (optionally) aspirating the captured clot and debris.

In variations on the disclosed method, it is envisioned that aspiration, maceration, and irrigation may be constant or intermittent. It is also envisioned that aspiration may constant while maceration and irrigation may each be intermittent. It is also envisioned that aspiration and maceration may be constant while irrigation may be intermittent. It is also envisioned that aspiration and irrigation may be constant while maceration may be intermittent. It is also envisioned that irrigation may be constant while maceration and aspiration may be intermittent. It is also envisioned that two or more of aspiration, irrigation, and maceration may occur simultaneously. It is also envisioned that two or more of aspiration, irrigation, and maceration may occur asynchronously. It is also envisioned that any component described herein may be operated intermittently and/or continuously and that any component described herein may be synchronous or asynchronous with other components.

Method 5: Combining any Combination of Method 1, 2, 3, and 4 with a Blockage Retrieval Device, a Non-Limiting Example of which is a Retrievable Stent Such a Solitaire (Medtronic) or Trevo (Stryker) Device.

The present disclosure contemplates various methods of removing a blockage in a patient's blood vessel, which may include cells, debris (e.g., cell debris), emboli, or other such material, either exclusively or in combination. For example, one method includes: introducing a first device to the site of the blockage to agitate, break up, macerate, or otherwise fragment the blockage and introducing a second device (e.g., an interventional device) at a site away from the site of the blockage to capture emboli resulting from fragmentation of the blockage.

In variations on the disclosed method, it is envisioned: that debris (e.g., fragments of the blockage) travelling in the direction of blood flow may be collected by a filter element (e.g., a semi-permeable membrane, a net, a mesh, or other such suitable structure) located away from the site of the blockage; that debris may be removed via aspiration at the site of the blockage (e.g., via an aspiration catheter having a filter element embedded or otherwise supported at an end thereof). In such methods, it is envisioned that the system may include irrigation and/or maceration elements positionable at the site of aspiration, either as an additional component of the aspiration catheter or as a separate component. It is also envisioned that aspiration may be applied to clear (clean) the filter element of debris buildup. It is also envisioned that the filter element may be recaptured and removed with captured clot and debris to remove captured clot and debris.

It is also envisioned that an IVUS may be deployed to monitor the rate of blood flow through the filter element. For example, the IVUS may be used to establish a baseline flow rate (e.g., when the filter element is clear of any debris) and subsequently monitor the flow rate as debris buildup occurs during the course of the endovascular procedure. In the event that the flow rate drops below a certain threshold (e.g., approximately 80%), action may be taken to ameliorate or remove the debris buildup (e.g., via the use of an aspirator).

In one particular embodiment, the macerating irrigation catheter (hypotube) 300 (FIGS. 5, 9) may be utilized to simultaneously macerate a blockage B (FIG. 3) (e.g. in a rotating, eggbeater-like manner) while communicating an irrigation fluid into the blood vessel V. The macerating irrigation catheter 300 offers certain advantages over known technology, such as, for example, a sinusoidal cable, in that the macerating irrigation catheter 300 facilitates both maceration and irrigation (e.g., into and beyond the blockage).

As illustrated in FIG. 14, for example, it is envisioned that one or more inflatable members (e.g., balloons) may be mounted to the aspiration catheter and configured for use at the face of the blockage B (FIG. 3) (e.g., an arterial thrombus). For example, it is envisioned that the inflatable member(s) may be configured and utilized to occlude the blood vessel V and facilitate the reversal of blood flow reversal (e.g., by simultaneously aspirating the blood vessel V and irrigating distally of the blockage B).

The present disclosure also envisions the use of vibrational wire(s), balloons, and aspirator elements with or without filters.

Figure 15:
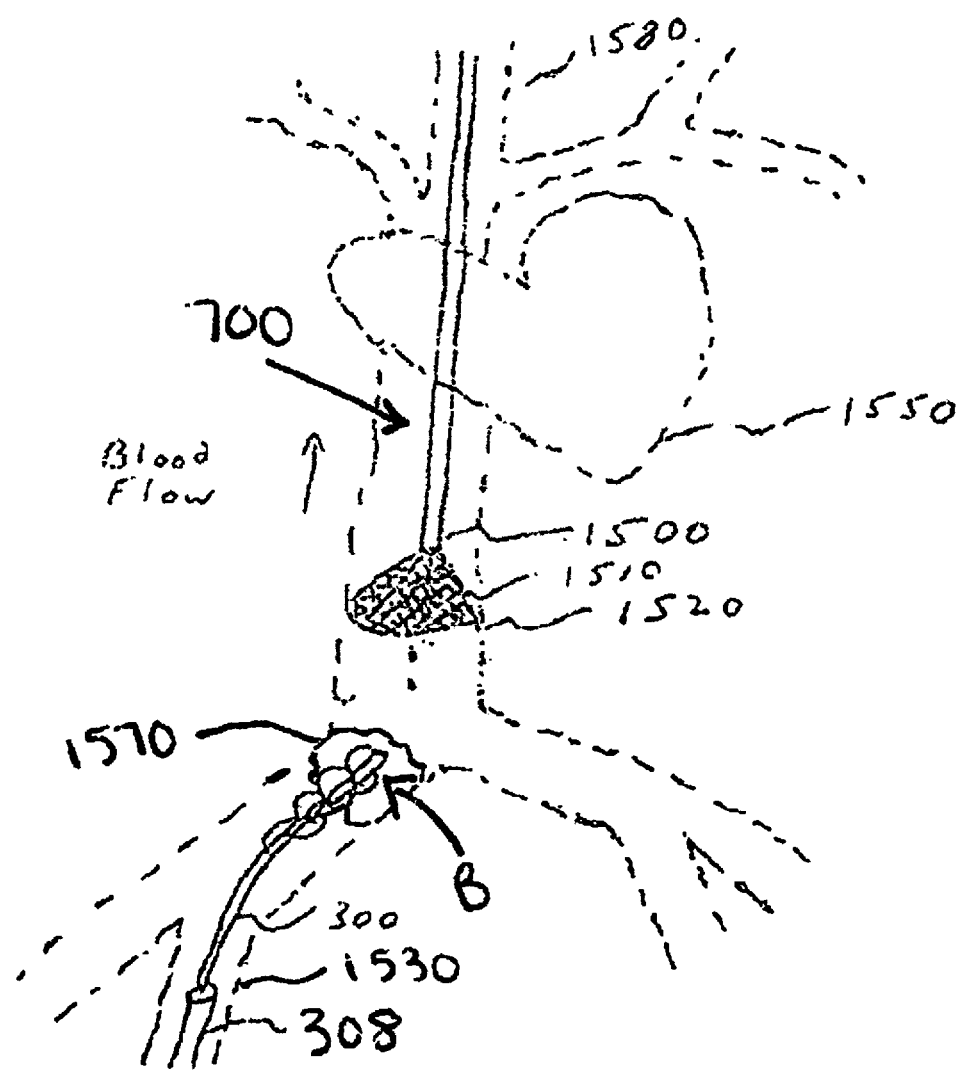
FIG. 15 shows a cross section side view of one embodiment of the simultaneous, irrigating, macerating device/system (e.g., microcatheter) of the present disclosure inserted through the femoral vein disposed at the site of an iliac blockage, further depicting a filter-tip aspiration catheter inserted into the inferior vena cava (IVC) to simultaneously catch thrombi released by the procedure.

Referring now to FIG. 15, the present disclosure contemplates an endovascular system (and corresponding method of use) that includes two separate (endovascular) devices to treatment a blockage B (FIG. 3) within a blood vessel V. For example, FIG. 15 illustrates use of the macerating irrigation catheter 300 in conjunction with a retrieval mechanism 700 which, in the illustrated embodiment, is configured as an aspiration catheter 1500 that includes at least one filter element 1510 disposed at (or adjacent to) a distal end (tip) thereof. Suitable (non-limiting) examples of the aspiration catheter 1500 include the aspiration catheter 800 (FIGS. 7F-7I) and the aspiration catheter 1000 (FIGS. 8, 8A, 8B). In variations on the system (devices) and method seen in FIG. 15, it is envisioned that the retrieval mechanism 700 may instead be configured for direct contact with the blockage B such that the blockage B is withdrawn upon retraction of the retrieval mechanism 700. For example, it is envisioned that the retrieval mechanism 700 may include a grabber, pincer, or the like.

It is envisioned that the aspiration catheter 1500 may define an axial (longitudinal) length that lies substantially within the range of (approximately) 0.5 cm to (approximately) 160 cm and a transverse cross-sectional dimension (e.g., a diameter) that lies substantially within the range of (approximately) 0.1 mm to (approximately) 25 mm. It is also envisioned that the filter element may be configured so as to define a transverse cross-sectional dimension (e.g. a diameter) upon deployment (expansion) that lies substantially within the range of (approximately) 0.1 mm to (approximately) 100 mm.

Although shown as being including (generally) circular outer and inner transverse cross-sectional configurations, it should be appreciated that the particular configuration of the aspiration catheter 1500 may be varied without departing from the scope of the present disclosure. For example, it is envisioned that the aspiration catheter 1500 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the aspiration catheter 1500 may be circular and that the inner transverse cross-sectional configuration of the aspiration catheter 1500 may be non-circular. It is also envisioned that the outer transverse cross-sectional configuration of the aspiration catheter 1500 may be non-circular and that the inner transverse cross-sectional configuration of the aspiration catheter 1500 may be circular.

It is envisioned that the filter element 1510 may be configured for self (automatic) expansion or that the filter element 1510 may be configured for expansion upon the inflation of an inflatable member (e.g., proximal to the filter element 1510).

In the particular method reflected in FIG. 15, the macerating irrigation catheter 300 is introduced into the femoral vein sheath or via a vein lower on the leg (via a first, upstream access point) and advanced to the site of a blockage B (e.g., an iliac clot 1570). To facilitate placement and advancement of the macerating irrigation catheter 300, is envisioned that a delivery member may be utilized. For example, it is envisioned that the delivery member may include the aspiration catheter 400 (FIG. 6), an outer (delivery) catheter (sheath) 308, or any other such suitable device. Alternatively, it is envisioned that a macerating element, with or without an irrigating element, may be advanced directly through aspiration catheter 1500 rather than through a separate vascular access site.

The aspiration catheter 1500 is introduced into the jugular vein 1580 or other vessel (via a second access point such that the filter element 1510 is ultimately placed downstream from the blockage B), through the heart 1550 from a direction opposite to that of blood flow in the inferior vena cava (IVC) 1520 to a position in the inferior vena cava (IVC) 1520 beyond the heart to capture (catch) emboli in the filter element 1510 (subsequent to deployment). Upon deployment, the periphery of the filter element 1510 is located proximal to, and within, the IVC 1520. It is envisioned that the filter element 1510 (e.g., a peripheral or circumferential portion thereof) may contact the walls of the vessel. Blood flows in the direction of the heart 1550, into the filter element 1510 (potentially carrying debris or particulate matter freed up by the simultaneous irrigation into and maceration of the blockage B). In certain embodiments, the filter element 1510 may include a semi-permeable filter membrane that is configured to capture smaller particulate matter than conventional wire structures (such as a traditional Greenfield filter) and, thus, more effectively protects the heart 1550 and other organs from the effect of small and medium sized emboli, in addition to protection against large emboli. Use of the filter element 1510 also eliminates the significant risks of deploying and removing known implant filter devices.

Figure 15A:
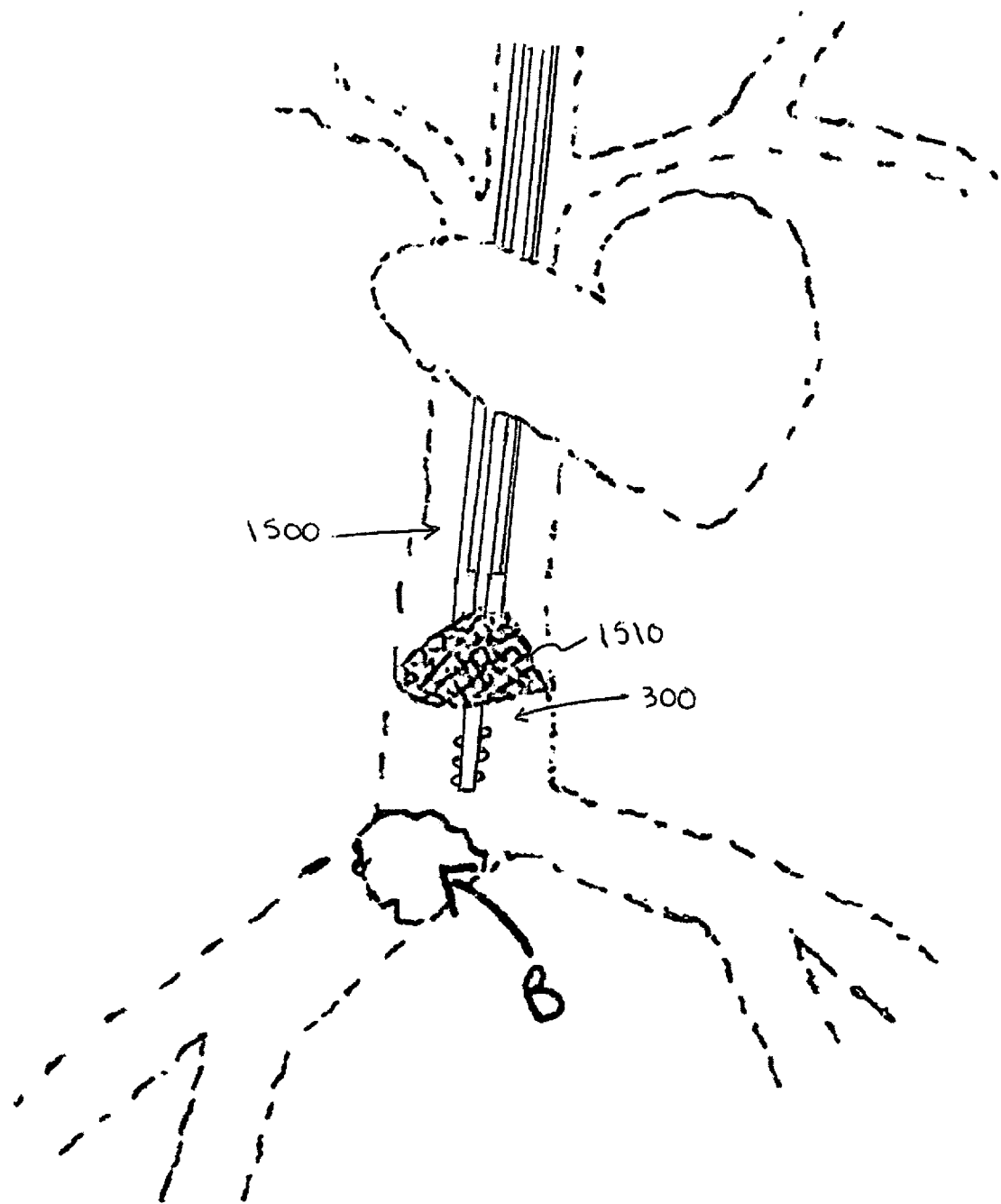
FIGS. 15A and 15B show alternate embodiments and uses of the simultaneous, irrigating, macerating device/system (e.g., microcatheter) seen in FIG. 15.

FIG. 15A illustrates an alternate embodiment of the disclosure in which the macerating irrigation catheter 300 and the aspiration catheter 1500 are each introduced downstream of the blockage B. More specifically, in the illustrated embodiment, the macerating irrigation catheter 300 is introduced through the aspiration catheter 1500 (e.g., through the filter element 1510).

Figure 15B:
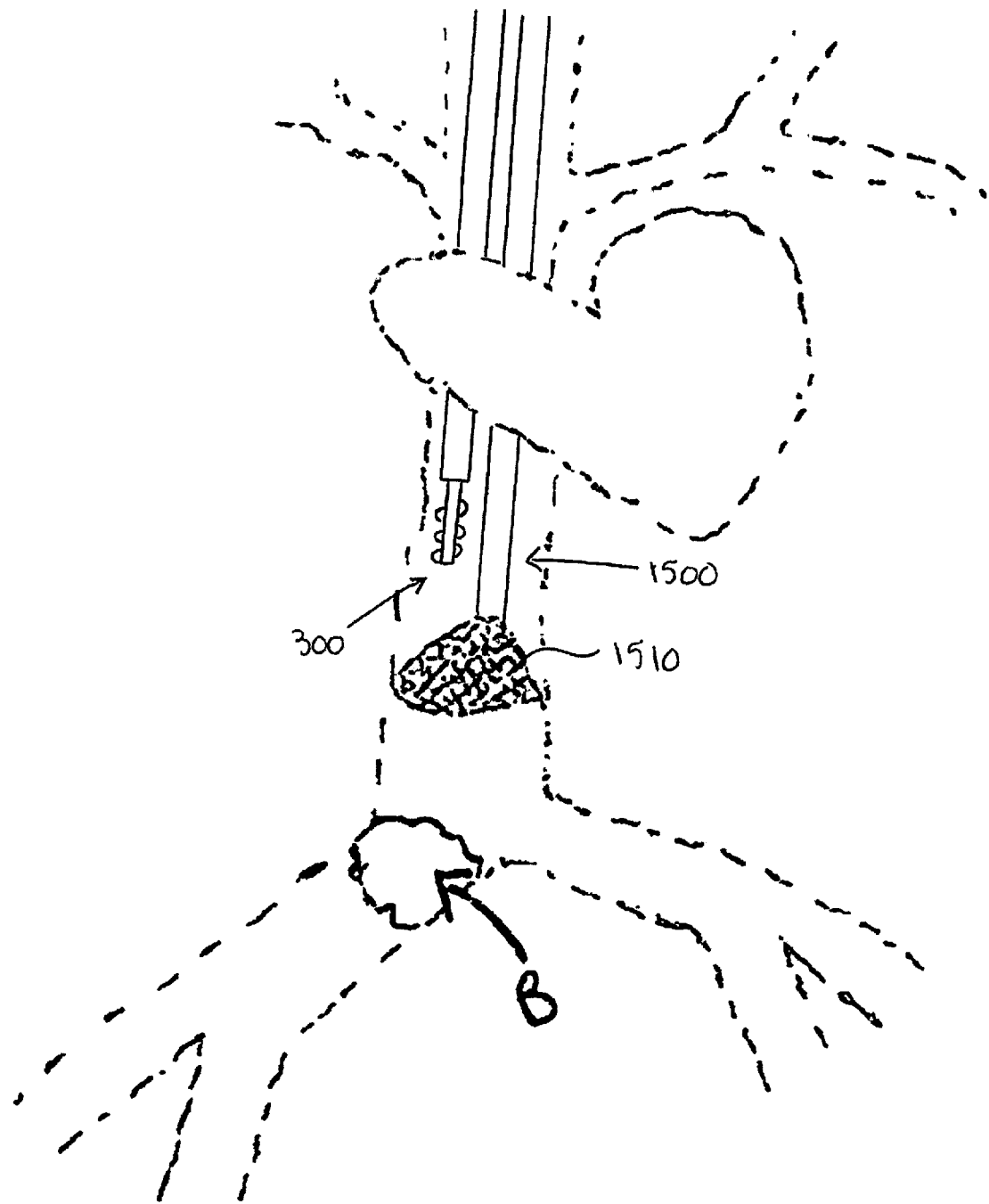

FIG. 15B illustrates a variation on the embodiment seen in FIG. 15A. More specifically, in the embodiment illustrated in FIG. 15B, the macerating irrigation catheter 300 is introduced separately from the aspiration catheter 1500 (e.g., such that the macerating irrigation catheter 300 and the aspiration catheter 1500 are advanced in side-by-side relation in an upstream direction).

With reference to FIG. 16, in an alternate method of use, the aspiration catheter 1500 may be introduced via the descending aorta 1680 and may optionally include a non-linear configuration (in contrast to the embodiment seen in FIG. 15, for example). For example, in FIG. 16, the aspiration catheter 1500 is illustrated as including at least one bend (e.g., a first bend 1700 and a second bend 1701) located proximally of the filter element 1510 (e.g., between the filer element 1510 and the proximal end (not shown) of the aspiration catheter 1500). In one particular embodiment, it is envisioned that the aspiration catheter 1500 may be configured and deployed such that the first bend 1700 is located proximal to the left subclavian artery 1900, but not further than a line defined by the high point of the aortic arch 2000 and the most proximal opening of the left carotid artery 2100 and such that the second bend 1701 is located distally of the line defined by the uppermost point of the aortic arch 2000 and the most proximal opening of the left common carotid artery 2001 and proximal to the innominate artery 1910. Alternatively, or in combination, it is envisioned that the aspiration catheter 1500 may include at least one steerable segment.

In various embodiments of the disclosure, it is envisioned that the aspiration catheter 1500 may be configured and deployed such that the filter element 1510 is disposed within the ascending aorta 1690. For example, the aspiration catheter 1500 may be deployed such that the filter element 1510 is inserted into the patient's ascending aorta 1690 to filter flow downstream toward the patient's descending aorta 1680. It is also envisioned that the aspiration catheter 1500 may be sheathed in a delivery catheter (sheath) 1540. As indicated above, it is envisioned that the aspiration catheter 1500 and the filter element 1510 may be inserted and removed through the outer catheter 1530. To facilitate insertion and removal of the aspiration catheter 1500 and placement of the outer catheter 1530, it is envisioned that the outer catheter 1530 may include one or more bends or curves, a steerable segment, etc.

It is also envisioned that the filter element(s) 1510 may include a hydrogel (not shown) (e.g., about a peripheral edge 1511 thereof). The hydrogel may also be present on those sections of the aspiration catheter 1500 that are likely to contact a wall of the blood vessel when deployed (e.g., the first bend 1700 (FIG. 16)). In such embodiments, it is envisioned that the inclusion of a hydrogel may improve adherence to the wall of the blood vessel (e.g., at the site of the first bend 1700) and may inhibit (if not entirely prevent) "endoleaks" of unfiltered blood between the filter element 1510 and the wall of the blood vessel (as described in claims 10 and 17 of U.S. Pat. No. 9,775,730 B1 [Walzman]). Hydrogel may also be optionally used as a replacement to a balloon in various embodiments of the present disclosure.

In certain methods of use, it is envisioned that the endovascular devices described herein may be used during the course of a heart valve-replacement procedure in which a replacement (first) valve is used and positioned to replace, repair, or supplement a damaged (second) valve. It is envisioned that the replacement valve may include an anatomical (natural) valve (e.g., from a donor or a cadaver) or an artificial valve and that the damaged valve may include an (existing) anatomical valve occurring naturally within the patient, such as the patient's aortic valve, for example, or an (existing) artificial valve. Additional cardiac procedures may also benefit from the embolic protection afforded from the systems and devices described herein (e.g., in the ascending aorta). In order to increase (e.g., maximize) coverage of the origin of the innominate artery while reducing (e.g., minimizing) any potential contact with other devices, it is envisioned that the filter element 1510 may include an irregular or asymmetrical configuration, as seen in FIGS. 5E-5I, for example.

In one particular implementation, it is envisioned that the endovascular devices described herein may be used during a minimally invasive transcatheter aortic valve replacement (TAVR) procedure in which the replacement valve is inserted into the damaged valve and expanded (e.g., via an inflatable member (e.g., a balloon), self-expanding, or any other such suitable mechanism) such that the replacement valve operates in place of the damaged valve (e.g., to regulate blood flood). It is also envisioned that the endovascular devices described herein may further include such a replacement valve R (FIG. 16) and/or its delivery system.

In the method seen in FIG. 16, an endovascular device (e.g., the aspiration catheter 1500) is delivered (e.g., via the femoral artery (not shown)) and over the aortic arch 2000 such that the filter element 1510 and the distal end of the aspiration catheter 1500 face the aortic valve 3000 within the ascending aorta 1690 between the heart and the innominate artery 1910. Thereafter, the filter element(s) 1510 may be deployed and a replacement valve R may be delivered into the patient's heart 1550 (e.g., the aortic valve 3000) through the aspiration catheter 1500 (e.g., through the filter element(s) 1510). In certain embodiments, however, it is also envisioned that the damaged valve (e.g., the aortic valve 3000) may be retrieved (removed), either prior or subsequent to insertion of the replacement valve R into the patient's vasculature, and replaced by the replacement valve R. Alternatively, valvulopasty and/or valve lithotripsy may be performed, with or without subsequent valve procedures. Other left heart devices and procedures may also be delivered and utilized in this manner (e.g., while the filter element 1510 captures emboli).

To facilitate advancement of the replacement valve R through the aspiration catheter 1500, it is envisioned that a separate delivery member 600 (e.g., a delivery catheter 602, a pusher, etc.) may be utilized. More specifically, it is envisioned that the delivery member 600 may carry (or otherwise support) the replacement valve R and that the delivery member 600 and the replacement valve R may be inserted into, and advanced through, the aspiration catheter 1500, to the patient's heart, as seen in FIG. 16.

Although shown as being including (generally) circular outer and inner transverse cross-sectional configurations, it should be appreciated that the particular configuration of the delivery member 600 may be varied without departing from the scope of the present disclosure. For example, it is envisioned that the delivery member 600 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the delivery member 600 may be circular and that the inner transverse cross-sectional configuration of the delivery member 600 may be non-circular. It is also envisioned that the outer transverse cross-sectional configuration of the delivery member 600 may be non-circular and that the inner transverse cross-sectional configuration of the delivery member 600 may be circular.

Figure 16A:
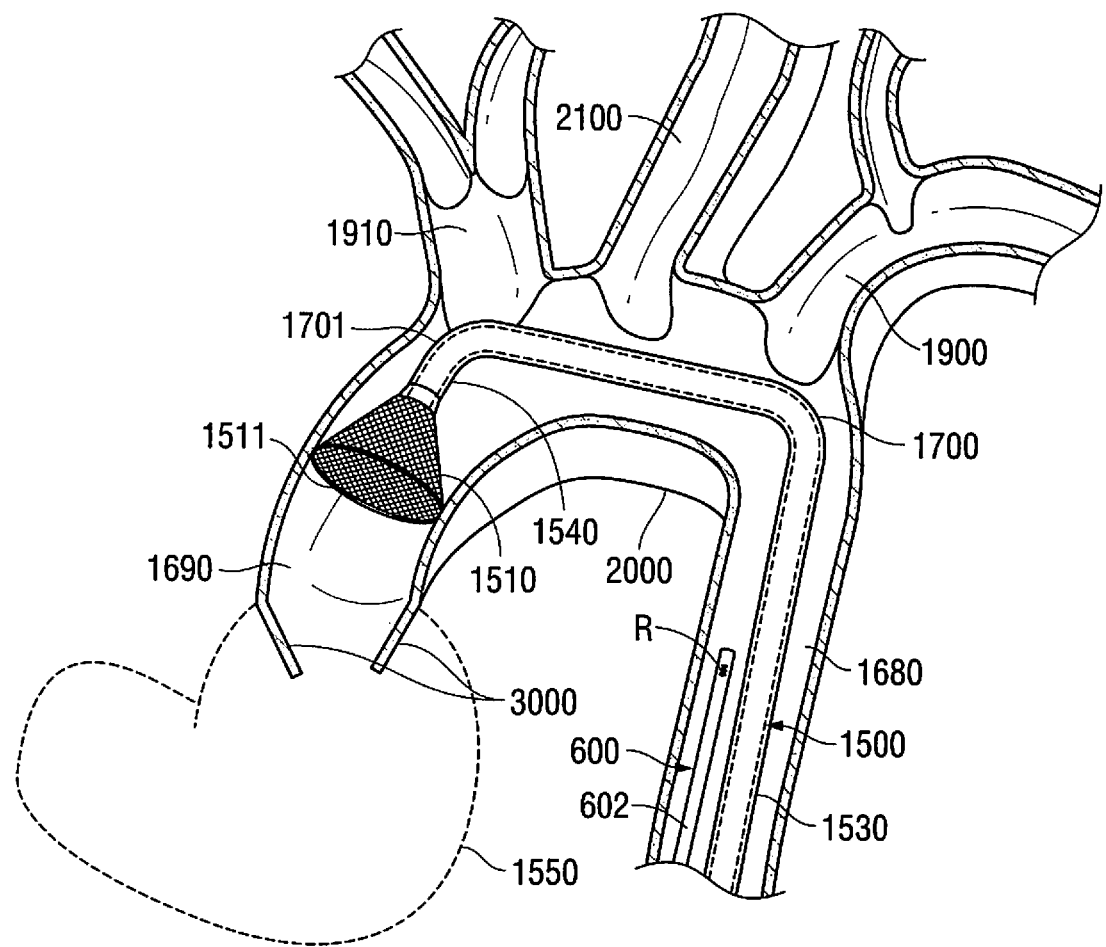
FIG. 16A shows a cross section side view of one embodiment of a replacement valve procedure.
Figure 16B:
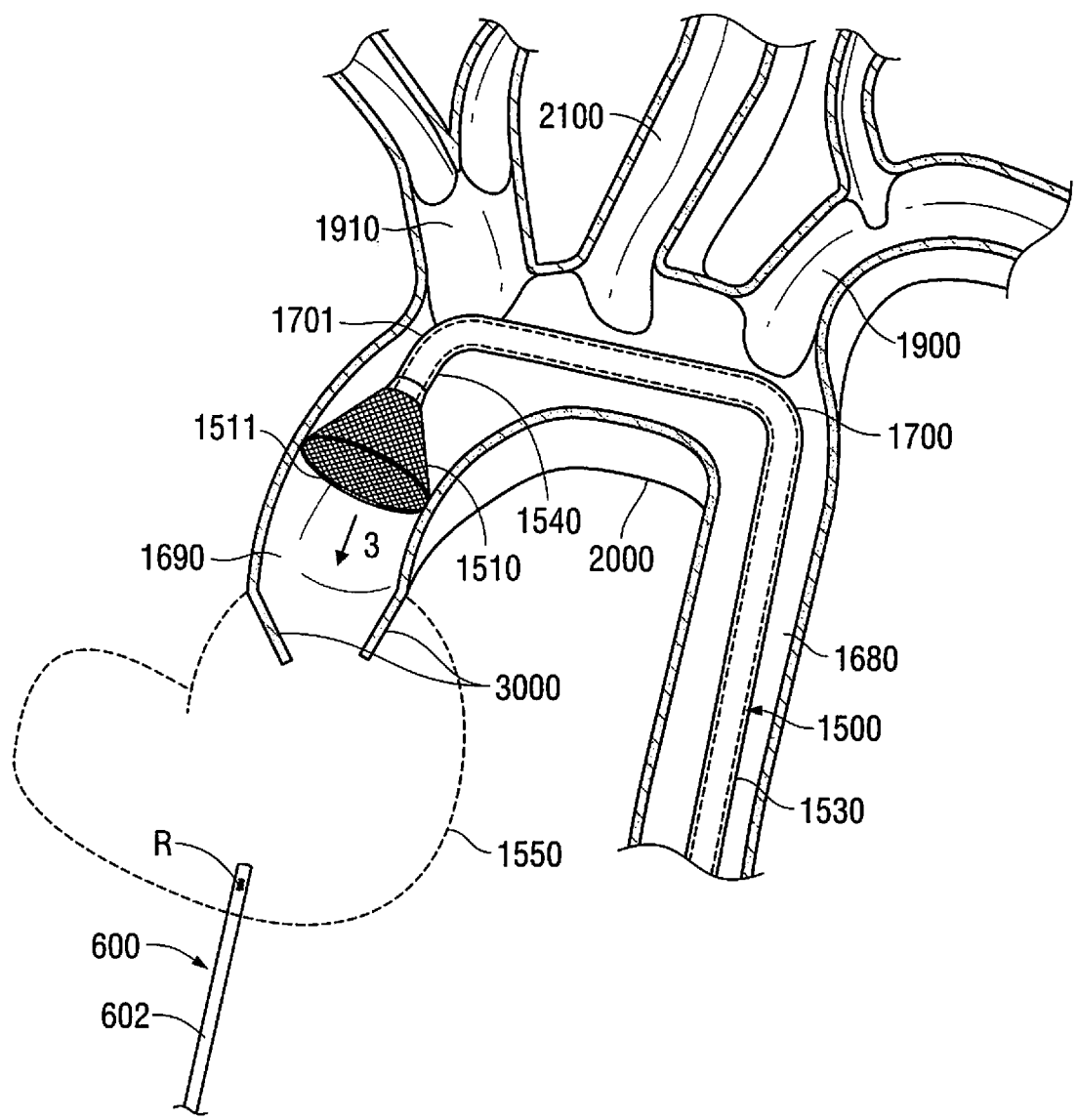
FIG. 16B shows a cross section side view of one embodiment of a replacement valve procedure.

It is also envisioned that the delivery member 600 and the replacement valve R may be advanced to the patient's heart 1550 independently of (separately from) the aspiration catheter 1500 (e.g., such that the delivery member 600 and the replacement valve R are advanced through the patient's vasculature externally of the aspiration catheter 1500), as seen in FIGS. 16A and 16B. In such embodiments, it is envisioned that the aspiration catheter 1500 and the delivery member 600 (and, thus, the replacement valve R) may be advanced through the vasculature in (generally) the same direction 3 (FIG. 16A), whether upstream or downstream, or that the aspiration catheter 1500 and the delivery member 600 (and, thus, the replacement valve R) may be advanced through the vasculature in different directions. For example, as seen in FIG. 16B, it is envisioned that the aspiration catheter 1500 may be advanced through the vasculature in one direction 3 (e.g., upstream or downstream) and that the delivery member 600 (and/or the replacement valve R) may be advanced through the vasculature in the a (generally opposite) direction 4 (e.g., upstream or downstream). One nonlimiting example may include a left atrial or mitral valve procedure performed via a venous approach, utilizing transseptal techniques.

Following insertion of the aspiration catheter 1500, the filter element(s) 1510 may be employed to capture emboli (or other such debris) (e.g., during delivery and/or placement of the replacement valve R). To enhance the capture of emboli, it is envisioned that the filter element(s) 1510 may be configured to (generally) conform to the patient's vasculature (e.g., the patient's ascending aorta 1690), such that the periphery (e.g., the circumference) of the filter element 1510 contacts the vessel walls such that blood flowing through the patient's vasculature travels through the filter element(s) 1510. The present disclosure thus facilities the protection of all three of the "Great Vessels" (e.g., the innominate artery 1910, left common carotid artery 2100, and left subclavian artery 1900, and their distal circulations), as well as the patient's descending aorta and the entire arterial supply to the rest of the body, from such emboli, in contrast to known technology (such as Claret Medical's Sentinel® Cerebral Protection System), which protects only the innominate artery 1910 and the left common carotid artery 2100, thus leaving circulation through the left subclavian 1900 and the entire descending aorta vulnerable.

Following deploying of the replacement valve R, the valve delivery system (when utilized) can be removed and aspiration can (optionally) be applied via the aspiration catheter 1500. The filter element 1510 may be then be collapsed (e.g., via re-sheathing into outer catheter 1530) and the endovascular device(s) can be removed. Hemostasis may then be achieved by the practitioner's method of choice (using standard techniques).

Aortic Arch
Normal Anatomy

The most common aortic arch branching pattern in humans consists of three great vessels originating from the arch of the aorta. The first branch is the innominate artery (brachiocephalic artery), which branches into the right subclavian artery and the right common carotid artery. The second branch in the most common pattern is the left common carotid artery, and the last branch is the left subclavian artery (Layton K. F. Am J Neuroradiol. 2006; 27:1541-1542) (FIG. 3).

Variant Anatomy of the Aortic Arch

Hypoplastic Ascending Aorta

Hypoplasia (underdevelopment or incomplete development) of the ascending aorta usually occurs concomitant with hypoplastic left heart syndrome (HLHS). HLHS comprises a wide spectrum of cardiac malformations, including hypoplasia or atresia (abnormal opening or failure of a structure to be tubular) of the aortic and mitral valves and hypoplasia of the left ventricle and ascending aorta. The great vessels are normally related in this congenital anomaly. HLHS has a reported prevalence of 0.2 per 1000 live births and occurs twice as often in boys as in girls. Left untreated, HLHS is lethal (Kau T. et al. Semin Intervent Radiol. 2007; 24 (2): 141-152).

Coarctation of the Aorta

Coarctation of the aorta accounts for about 5 to 7% of all congenital heart disease. It is defined as a discrete stenosis in the proximal descending thoracic aorta. Only those with the most severe obstruction (e.g., aortic arch atresia or interruption) or associated cardiac defects invariably present in infancy (Jenkins N. P., Ward C. QJM. 1999; 92:365-371). Most other cases are identified because of a murmur or hypertension found on routine examination. Age at presentation is related to the severity rather than the site of obstruction, as a result of cardiac failure or occasionally cerebrovascular accident, aortic dissection, or endocarditis (Jenkins N. P., Ward C. QJM. 1999; 92:365-371). Aortic coarctation may be subclassified into isolated coarctation, coarctation with ventricular septal defect, and coarctation with complex intracardiac anomalies (Backer C. L. et al. Ann Thorac Surg. 2000; 69: S308-S318). An exceedingly rare congenital anomaly is coarctation of a right aortic arch (Maxey T. S. et al. J Card Surg. 2006; 21:261-263).

Interrupted Aortic Arch

Interrupted aortic arch is defined as the loss of luminal continuity between the ascending and descending aorta and is associated with a multitude of lesions ranging from isolated ventricular septal defects to complex ones (Kau T. et al. Semin Intervent Radiol. 2007; 24 (2): 141-152). An interrupted aortic arch may be subclassified into anatomical types based on the location of the interruption (Maxey T. S. et al. J Card Surg. 2006; 21:261-263). Although results have improved, repair of this abnormality is associated with a significant mortality and morbidity (Tchervenkov C. I. et al. Semin Thorac Cardiovasc Surg Pediatr Card Surg Annu. 2005:92-102).

Patent Ductus Arteriosus

A ductus arteriosus Bot211i permits blood flow between the aorta (distal to the left subclavian artery) and the pulmonary artery. In a full-term infant, the ductus usually closes within the first 2 days of life. Persistent patency beyond that point is generally permanent, being two to three times as common in girls as in boys. Most of the cases occur as isolated defects. Typical concomitant findings are left ventricle hypertrophy and pulmonary artery dilation. Persistent ductus arteriosus may also be associated with coarctation of the aorta, transposition of the great vessels, and ventricular septal defect (Campbell M. Br Heart J. 1968; 30:4-13).

Thyroid Ima Artery

The thyroid ima artery is a collateral vessel feeding the thyroid gland (Wolpert S. M. Radiology 1969; 92:333-334). This blood vessel occurs in up to 16.9% of the population (Vasovic L. et al. Ital J Anat Embryol. 2004; 109:189-197). It may be a branch of the aortic arch between the brachiocephalic and left subclavian arteries. However, more frequently it is a branch of the brachiocephalic artery. A further variant of origin is from the right common carotid artery. In the remaining cases, it may originate from the internal mammary, subclavian, or inferior thyroid arteries (Kadir S. In: Kadir S, editor. Atlas of Normal and Variant Angiographic Anatomy. Philadelphia: WB Saunders; 1991. Regional anatomy of the thoracic aorta. pp. 19-54).

Aberrant Right Subclavian or Brachiocephalic Artery

The right subclavian artery is the last branch of the aortic arch in approximately 1% of individuals (Richardson J. V. et al. Ann Thorac Surg. 1981; 31:426-432). It courses to the right behind the esophagus in approximately 80% of these cases, between the esophagus and trachea in 15%, and anterior to the trachea or mainstem bronchus in 5% (Kadir S. In: Kadir S, editor. Atlas of Normal and Variant Angiographic Anatomy. Philadelphia: WB Saunders; 1991. Regional anatomy of the thoracic aorta. pp. 19-54).

Right Aortic Arch

Right aortic arch is an uncommon anatomical anomaly that occurs in <0.1% of the population (Cina C. S. et al. J Vasc Surg. 2004; 39:131-139). It results from the persistence of the right fourth bronchial arch (Kadir S. In: Kadir S, editor. Atlas of Normal and Variant Angiographic Anatomy. Philadelphia: WB Saunders; 1991. Regional anatomy of the thoracic aorta. pp. 19-54). The most common type is the right aortic arch with an aberrant left subclavian artery. The blood vessels originate in the following order: left common carotid, right common carotid, right subclavian, and left subclavian artery. This type is rarely associated with congenital heart disease. However, symptoms may arise from vascular ring formation (Son J. A. et al. J Card Surg. 1999; 14:98-102). The mirror-image type (left brachiocephalic trunk, right common carotid and subclavian arteries) is almost always associated with congenital heart disease, especially the cyanotic type (McElhinney D. B. et al. Pediatr Cardiol. 2001; 22:285291).

Ductus Diverticulum

The aortic isthmus in adults has a variable appearance. Its configuration may show a concavity, a straightening or slight convexity, or a discrete focal bulge. The latter finding represents a ductus diverticulum, present in about 9% of individuals. Representing the most distal segment of the embryonic right arch, the ductus diverticulum is a fusiform dilation of the ventromedial portion of the proximal descending thoracic aorta. At times a prominent ductus diverticulum may resemble a traumatic pseudoaneurysm of the aortic isthmus (Goodman P. C. et al. Cardiovasc Intervent Radiol. 1982; 5:1-4).

Double Aortic Arch

The double aortic arch is a rare anomaly caused by persistence (to varying degrees) of the fetal double aortic arch system (Kadir S. In: Kadir S, editor. Atlas of Normal and Variant Angiographic Anatomy. Philadelphia: WB Saunders; 1991. Regional anatomy of the thoracic aorta. pp. 19-54). The ascending aorta divides into two arches that pass to either side of the esophagus and trachea and reunite to form the descending aorta. Therefore, it is a form of complete vascular ring, resulting in noncardiac morbidity, but rarely associated with intracardiac defects (Alsenaidi K. et al. Pediatrics. 2006; 118: e1336-e1341). The descending aorta is usually on the left side. Most commonly, one arch is dominant, whereas the other may be of small caliber or represented by a fibrous band.

Cervical Aortic Arch

The cervical aortic arch refers to an unusually high location of the aortic arch in the low or midneck region (Kadir S. In: Kadir S, editor. Atlas of Normal and Variant Angiographic Anatomy. Philadelphia: WB Saunders; 1991. Regional anatomy of the thoracic aorta. pp. 19-54). This rare type of aortic arch anomaly is presumed to result from persistence of the third aortic arch and regression of the normal fourth arch. Abnormalities of brachiocephalic arterial branching and arch laterality are common in patients with a cervical aortic arch (McElhinney D. B. et al. Pediatr Cardiol. 2001; 22:285-291). There is no association with congenital heart disease, and the anomaly occurs most frequently in association with a right aortic arch. Most of the patients with this anomaly are asymptomatic, but symptoms of dysphagia and respiratory distress due to the compression by the vascular ring have been reported (Acikel U. et al. Angiology 1997; 48:659-662).

Bovine Aortic Arch

A common brachiocephalic trunk (also known as the innominate artery), in which both common carotid arteries and the right subclavian artery arise from a single trunk off the arch, is the most frequent normal variant of aortic arch branching (Kadir S. In: Kadir S, editor. Atlas of Normal and Variant Angiographic Anatomy. Philadelphia: WB Saunders; 1991. Regional anatomy of the thoracic aorta. pp. 19-54). The innominate artery and the left common carotid artery have a common origin. Therefore, only 2 great vessels originate from the aortic arch (Layton K. F. et al. Am J Neuroradiol. 2006; 27:1541-1542). Overall, this pattern of branching is seen in approximately 13% of patients (Lippert H, Pabst R. Aortic arch. In: Arterial Variations in Man: Classification and Frequency. Munich, Germany: J F Bergmann-Verlag; 1985:3-10). Although the term bovine aortic arch is ascribed to this anomaly, it is not commonly found in cattle (Layton K. F. et al. Am J Neuroradiol. 2006; 27:1541-1542).

Other Variant Branching

Variations in the sequence of branching of the major arch vessels also occur (<0.5%) (Kadir S. In: Kadir S, editor. Atlas of Normal and Variant Angiographic Anatomy. Philadelphia: WB Saunders; 1991. Regional anatomy of the thoracic aorta. pp. 19-54). For example, the left subclavian artery may be the second branch (before the left common carotid), or the internal and external carotid arteries may originate independently from the aortic arch (Nelson M. L., Sparks C. D. Clin Anat. 2001; 14:62-65).

Variant Origin of Vertebral Arteries

Various unusual vertebral artery origins exist (Yamaki K. et al. Anat Sci Int. 2006; 81:100-106; Koenigsberg R. A. et al. Catheter Cardiovasc Interv. 2003; 59:244-250). For example, the left vertebral artery arises from the aortic arch, with reported prevalences of 2.4 to 5.8% (Lemke A. J. et al. Am J Neuroradiol. 1999; 20:1318-1321). The most frequent location is between the left common carotid and subclavian arteries (Kadir S. In: Kadir S, editor. Atlas of Normal and Variant Angiographic Anatomy. Philadelphia: WB Saunders; 1991. Regional anatomy of the thoracic aorta. pp. 19-54). Rarely, the proximal left vertebral artery is duplicated in which one part arises from the arch and the other from the left subclavian, or both originate from the aortic arch. Occasionally, the left vertebral artery is the last branch of the aortic arch, which is rarely true for both vertebral arteries (Goray V. B. et al. Am J Neuroradiol. 2005; 26:93-95).

The existence of aortic and vertebral artery variations inhibits the treatment of diseases that require endovascular intervention via a transfemoral approach. For example, the acute angle at which the left common carotid artery branches from the aortic arch in the bovine arch configuration makes mechanical endovascular neuro-intervention difficult, especially when additional tortuosity (i.e., twists) in the aorta and/or the carotid artery are present. Currently, catheters exist that can access the origin of the left common carotid artery when arterial variations exist. However, when a wire is advanced through these catheters in order to achieve distal access to the artery head, these catheters lack adequate support which results in kickback into the aortic arch of the advancing wire. The lack of adequate support and the resulting kickback of the advancing wire make effective treatment impossible. Even when catheterization is achieved in these situations, the process of arriving at the correct combination of catheters and wires results in long treatment delays. In cases of acute stroke, long delays in obtaining access to arteries often leads to additional irreversible cell death with additional permanent neurologic injury.

Therefore, a need exists for an endovascular device capable of treating diseases that require endovascular intervention in a patient suffering from a blood vessel anomaly. The present disclosure provides a dual lumen endovascular device capable of effectively treating such patients by providing support and thus preventing kickback of an advancing wire, resulting in distal blood vessel access, blockage retrieval, embolization of an aneurysm and/or embolization of an arteriovenous malformation (AVM).

The second component of the present disclosure (e.g., the bypass catheter component) is described in additional detail below. In the various views of the drawings, like reference characters designate like or similar parts.

Additional Method and Optional Variants

Further in accordance with the foregoing, still another stepwise method is provided for preventing thromboembolic injury during a medical vascular procedure. This method comprises the steps of:

(a) advancing a first catheter with a balloon on its external surface into a blood vessel upstream of a procedural site, (b) advancing a second hollow medical tube device into and past said procedural site, (c) inflating said balloon on said first catheter with a balloon on its external surface to obstruct flow upstream, (d) injecting a fluid into said blood vessel at said procedural site and/or downstream to said procedural site via said second hollow tube, (e) simultaneously aspirating through the proximal end of said first catheter and thereby inducing flow reversal in said blood vessel at said procedural site via said simultaneous flow obstruction, injection of said fluid, and aspiration, thereby removing emboli freed during said medical procedure and preventing downstream emboli during said medical procedure.

In an optional alternative, the foregoing method further comprises the steps of passing aspirated blood through a filter and returning said filtered aspirate to the patient.

In an optional alternative, the irrigation fluid may further include thrombolytic agents, coolants, tissue protectants, and/or other drugs.

In an optional alternative, the procedural site is a thromboembolic or thrombotic blockage. Said medical vascular procedure is a procedure to ameliorate said thromboembolic or thrombotic blockage.

In still another alternative, the foregoing method further comprises activating a maceration device/element during the simultaneous flow obstruction, injection of fluid, and aspiration.

In still another alternative, the second hollow medical tube further comprises said maceration device/elements. In another, said maceration element(s) comprise adhered wires on the second hollow medical tube. In yet another, said maceration element(s) comprise adhered loops on the second hollow medical tube.

In still another alternative, the maceration element(s) comprise a sinusoidal shape of the second hollow tube, which is capable of maceration when rotated.

In another, the procedural site is a blockage. The medical vascular procedure is a procedure to ameliorate said blockage. This optionally further includes the step of deploying a balloon and/or a stent.

In still another alternative, the foregoing method further the steps of introducing an angioplasty balloon, inflating said balloon, and removing said balloon. This optionally further includes the step of deploying a stent.

In the foregoing process, where a thromboembolic or other blockage is ameliorated, optionally including the deployment of a stent or balloon, including inflation/deflation and removal, said fluid contains may blood and/or lytic medication.

Additionally, the use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply.

One of the problems associated with using balloons is that although control of the blood flow through a portion of the blood vessel is achieved, including blockage of the blood supply to a targeted site, blood flow is completely interrupted to other sites near the targeted site.

This shortcoming can be tolerated for a short duration because when one blood vessel becomes blocked, the body normally increases the blood flow through other, essentially paralleling blood vessels. However, complex medical procedures may not be achieved during said short duration resulting in injury to said other sites or requiring multiple operations at the same targeted site. Additionally, current bypass catheters are designed to be surgically implanted, which is not practical for immediate relief of progressive ischemia caused by a sudden blockage of a blood vessel, such as from a thrombus or embolus.

The present disclosure surmounts the problem of complete blood interruption that causes ischemia, which if not rapidly reversed will result in permanent injury. The present disclosure combines elements of three prior disclosures by Walzman, namely a temporary bypass catheter and balloon, a single lumen support catheter, and the rotating irrigating and aspirating thrombectomy device.

The present disclosure describes a catheter with at least one distal end hole, and at least one bypass window proximal to said end hole. In various embodiment, the presently disclosed catheter is configured for deployment across a blockage in a blood vessel.

The temporary balloon element, when present on the bypass catheter, is composed of a catheter with at least one distal end hole, at least one bypass window proximal to said end hole and a balloon element between said end hole and said bypass window. It is envisioned that the balloon element may be deployed, before inflation, across a blockage in a blood vessel or proximal to the blockage. There may be one or more additional lumens that extend within the wall of the bypass catheter and are configured to support inflation and deflation of the balloon. In alternative embodiments, one of more balloons may be present on an outer support catheter, through which the bypass catheter may be advanced.

Figure 17:
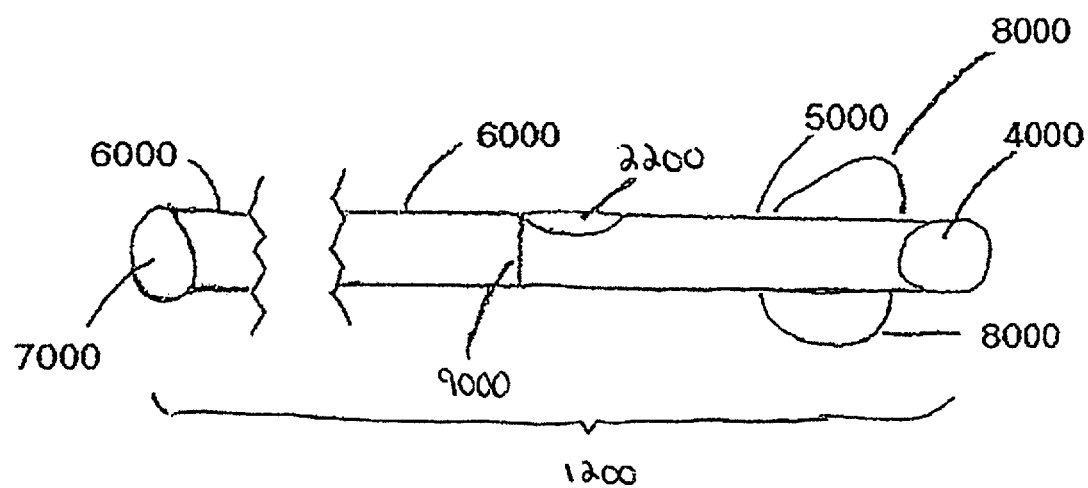
FIG. 17 is a side view of the present disclosure.

Referring now to FIG. 17, in another embodiment, the presently disclosed endovascular system includes a device 1200 (e.g. a bypass catheter) with a distal end hole 4000, one or more side holes 2200, a first segment 5000 defining a distal end hole 4000, and a second segment 6000 defining a proximal end hole 7000. The side hole(s) 2200 are located at (e.g., adjacent to) the juncture of the segments 5000, 6000 such that the side hole(s) 2200 define the distal end of the segment 6000 and the proximal end of the segment 5000.

While the outer transverse cross-sectional dimensions (e.g., the diameters) of the segments 5000, 6000 are illustrated as being (generally) identical in the particular embodiment seen in FIG. 17, it should be appreciated that the transverse cross-sectional dimensions of the segments, 5000, 6000 may differ from each other in alternate embodiments of the disclosure (e.g., it is envisioned that the outer transverse cross-sectional dimension of the segment 5000 may be less than or greater than that of the segment 6000).

Although shown as being including (generally) circular outer and inner transverse cross-sectional configurations, it should be appreciated that the particular configuration of the device 1200 may be varied without departing from the scope of the present disclosure. For example, it is envisioned that the device 1200 may include an outer transverse cross-sectional configuration and/or inner transverse cross-sectional configuration that is non-circular (e.g., oval, square, rectangular, triangular, trapezoidal, diamond, pentagonal, hexagonal, heptagonal, octagonal, nonagonal, decagonal, etc.), either individually or in combination. For example, it is envisioned that the outer transverse cross-sectional configuration of the device 1200 may be circular and that the inner transverse cross-sectional configuration of the device 1200 may be non-circular. It is also envisioned that the outer transverse cross-sectional configuration of the device 1200 may be non-circular and that the inner transverse cross-sectional configuration of the device 1200 may be circular.

It is envisioned that the device 1200 may be configured for insertion through an incision in a patient's blood vessel V (FIG. 3) (or other such percutaneous or surgical opening) and directed to a target site by means of standard endovascular techniques (e.g., with the aid of guidewires and/or other delivery catheters, fluoroscopic guidance, etc.).

The segment 5000 is configured and utilized to anchor the device 1200 within the blood vessel V (FIG. 3) so as to maintain positioning of the side hole(s) 2200 in a desired endovascular location. More specifically, in certain methods of use, it is envisioned that the device 1200 may be oriented such that side hole(s) are positioned to accept and direct blood flow through the segment 5000 and out of the distal end hole 4000, thereby redirecting blood flow around a blockage B (FIG. 3) and establishing a bypass.

In certain embodiments, such as that shown in FIG. 17, it is envisioned that the device 1200 may further include (support) one or more inflatable members 8000 (e.g., balloons) on an outer surface thereof such that, upon expansion, the inflatable member(s) 8000 enhance anchoring of the device 1200. Although shown as including a single inflatable member 8000 that is associated with the segment 5000 (e.g., such that the inflatable member 8000 is located between the side hole(s) 2200 and the end hole 4000) in the illustrated embodiment, it should be appreciated that the number and/or the location of the inflatable member(s) 8000 may be varied without departing from the scope of the present disclosure.

To inhibit (if not entirely prevent) the backflow of blood, it is envisioned that the device 1200 may include an (anti-backflow) valve 9000 that is located at (or adjacent to) the juncture of the section 6000 and the side hole 2200 (e.g., adjacent to a proximal end of the side hole(s) 2200). Once the device 1200 is positioned as necessary or desired in the blood vessel V (FIG. 3), the valve 9000 may be closed by the user to inhibit (if not entirely prevent) blood entering the side hole(s) 2200 from flowing (proximally) into the segment 6000. Rather, blood is directed through the segment 5000 and the distal end hole 4000, thereby bypassing the blockage B (FIG. 3) and perfusing the distal tissues.

Figure 18:
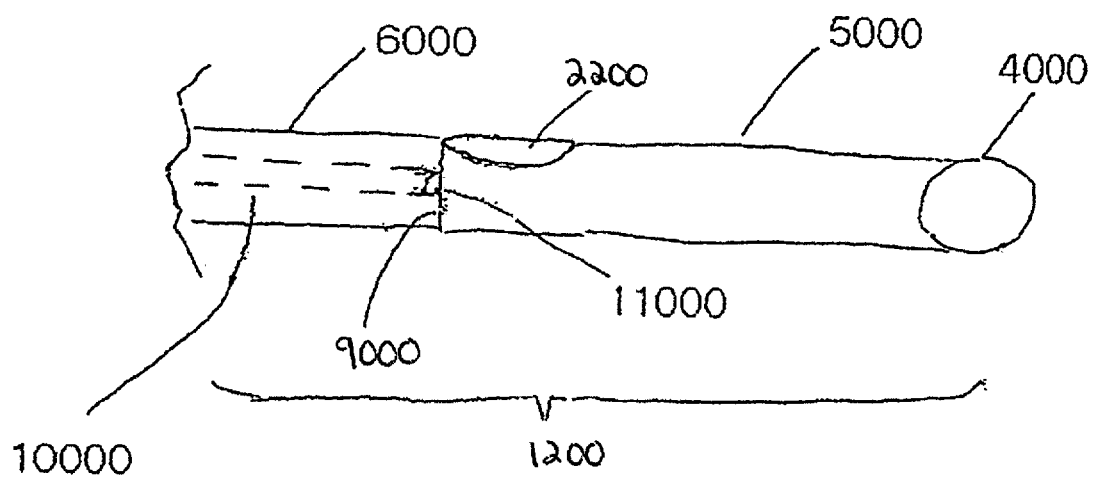
FIG. 18 is a side view of the present disclosure showing the inner segment with dashed lines.

Additionally, or alternatively, it is envisioned that the backflow of blood may be inhibited (if not entirely prevented) by configuring the device 1200 so as to reduce an internal transverse cross-sectional dimension 10000 (e.g., a diameter) of the segment 6000 in relation to that of the segment 5000, as seen in FIG. 18. In the particular embodiment shown, the internal transverse cross-sectional dimension 10000 (e.g., a diameter) of the segment 6000 is reduced so as to define an inner hole 11000 that is more restrictive to blood flow (e.g., smaller) than the end hole 4000, which results in a differential that deters backflow and directs blood through the segment 5000 and the end hole 4000.

Figure 19:
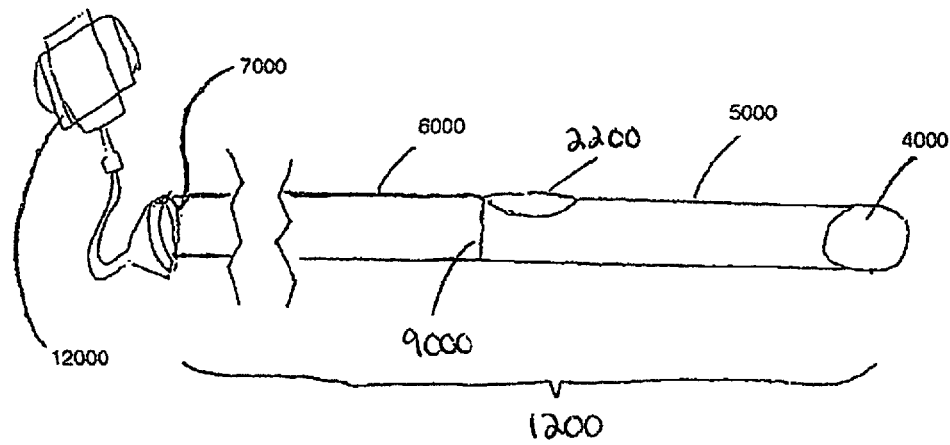
FIG. 19 depicts the first segment of the present disclosure connected to a pressurized fluid column.

Additionally, or alternatively, it is envisioned that the backflow of blood may be inhibited (if not entirely prevented) by introducing pressurized fluid into the segment 6000, as illustrated in FIG. 19. In the particular embodiment shown, the device 1200 is connected to a pressurized fluid source 12000 that is in fluid communication with the end hole 7000 such that pressurized fluid flows through the end hole 7000 and the segment 6000 into the segment 5000. To facilitate control over the flow of the pressurized fluid, it is envisioned that the pressurized fluid source 12000 may be attached to, connected to, or otherwise in communication with a flow regulator or controller (e.g., located externally of the patient).

Embodiments are envisioned in which the valve 9000, the reduced internal transverse cross-sectional dimension 10000 of the segment 6000, and the pressurized fluid source 12000 may be employed individually or in combination with each other. For example, the present disclosure envisions embodiments in which the device 1200 includes the valve 9000, the reduced internal transverse cross-sectional dimension 10000 of the segment 6000, and the pressurized fluid source 12000. Embodiments are also envisioned in which the device 1200 includes the valve 9000 and the reduced internal transverse cross-sectional dimension 10000 of the segment 6000, as are embodiments in which the device 1200 includes the valve 9000 and the pressurized fluid source 12000 and embodiments in which the device 1200 omits the valve 9000 but includes the reduced internal transverse cross-sectional dimension 10000 and the pressurized fluid source 12000.

Figure 20:
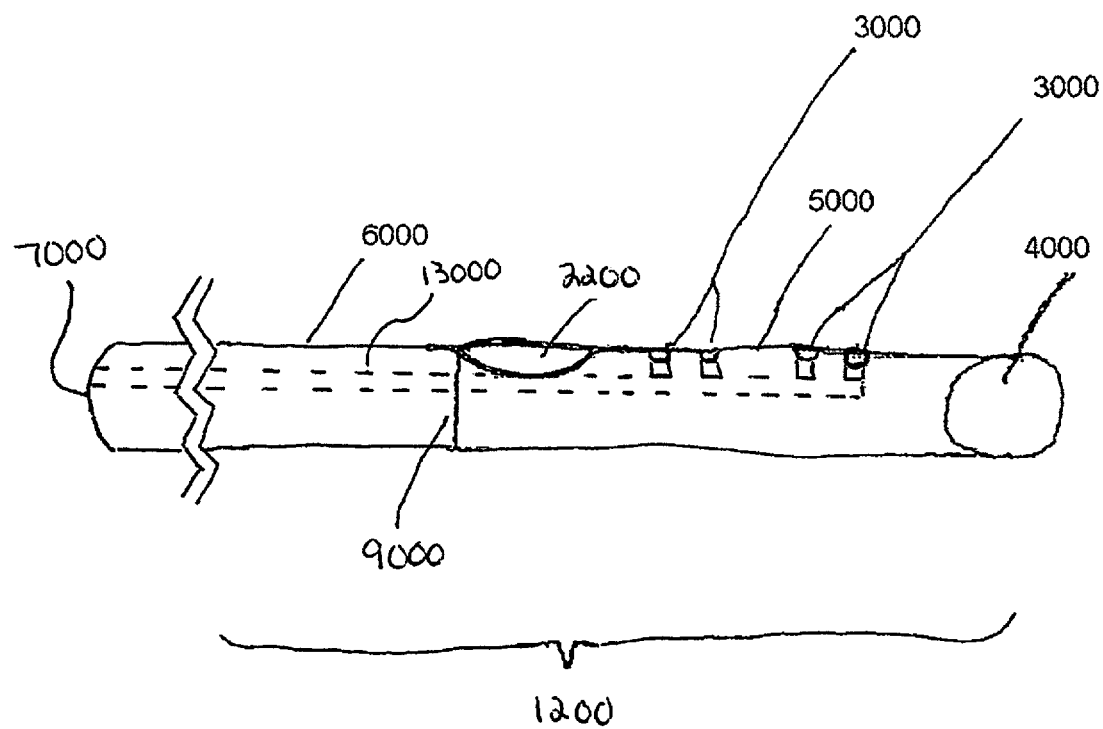
FIG. 20 is a side view of the present disclosure with perforations allowing infusion of medication from the proximal end.

To facilitate irrigation during the course of an endovascular procedure, it is envisioned that the device 1200 may include an irrigation channel 13000 that extends from (is in communication with) the end hole 7000 to one or more perforations (or other such openings) 30000 in the device 1200, as seen in FIG. 20. To facilitate control over the flow of the irrigation fluid, it is envisioned that the irrigation channel 13000 may be attached to, connected to, or otherwise in communication with an irrigation flow regulator or controller (e.g., located externally of the patient). Medications and other fluids may be infused as well.

It is envisioned that the irrigation fluid may be adapted and utilized to dissolve the blockage B (FIG. 3), blood clots, debris or emboli within the blood vessel V, etc. For example, it is envisioned that the irrigation fluid may be a lytic such as Alteplase, which dissolves blockages (such as blood clots, for example). It is also envisioned that the irrigation fluid may be adapted and utilized to softening and/or alter the chemical composition of the blockage B (e.g., proximal to perforations 30000) to facilitate dislocation of the blockage B.

In addition to, or instead of, the irrigation channel 13000, it is envisioned that the device 1200 may include concentric walls defining an irrigation conduit therebetween that extends from the end hole 7000 to the perforations 30000 (e.g., such that irrigation fluid is flowable between an internal surface of the outer wall and an outer surface of the inner wall). Distinct lumen(s) may alternatively extend within the wall of the bypass catheter to service fluid delivery through the perforations.

In such embodiments, it is envisioned that the irrigation conduit may be connected to the aforementioned irrigation flow regulator to again facilitate control over the flow of the irrigation fluid. It is also envisioned that the irrigation conduit may terminate at the distalmost perforation 30000, or that the irrigation conduit may terminate in the segment 5000 (e.g., at or adjacent to the end hole 4000).

Figure 21:
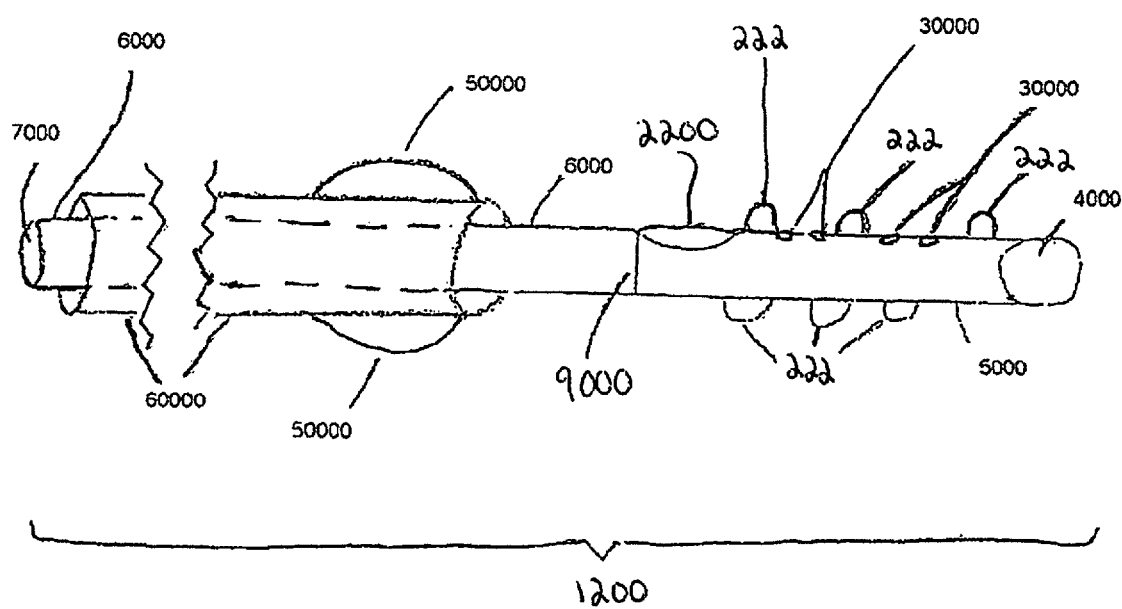
FIG. 21 depicts an alternative embodiment of the device of the present disclosure further including simultaneous rotating, macerating and irrigating elements, a slidable outer support sheath, macerating elements (or loops), and/or perforations that can be used as irrigating elements.

With reference now to FIG. 21, an alternate embodiment of the device 1200 is illustrated that includes one or more of the aforementioned macerating members 222 to agitate, break up, macerate, or otherwise fragment the blockage B (FIG. 3) upon rotation of the device 1200 as well as a slidable outer support sheath 60000.

The sheath 60000 defines an inner transverse cross-sectional dimension (e.g., a diameter) that closely approximates an outer transverse cross-sectional dimension (e.g., a diameter) of the device 1200 (e.g., the segment 5000) such that the sheath 60000 fits snugly around the device 1200 (e.g., such that the sheath 60000 contacts the device 12000 so as to form a fluid-tight seal therebetween). The sheath 60000 and the device 1200 are configured and arranged to permit relative axial (longitudinal) movement therebetween to facilitate reconfiguration of the device 1200 and the sheath 60000 between a first configuration, in which the sheath 60000 covers (closes) the side hole(s) 2200, and a second configuration, in which the side hole(s) 2200 are exposed from the sheath 60000. It is envisioned that reconfiguration of the device 1200 and the sheath 60000 may be achieved via withdrawal of the segment 5000 into the sheath 60000 and/or advancement of the sheath 60000 over the side hole(s) 2200.

Reconfiguration of the device 1200 and the sheath 60000 provides for the redirection of (and control over) blood flow through the device 1200. More specifically, when the device 1200 and the sheath 60000 are in the first configuration (e.g., when the side hole(s) 2200 are covered (closed) by the sheath 60000), blood flows from the distal end hole 4000 to the proximal end hole 7000, which allows for aspiration applied at the proximal hole 7000 to be communicated to the distal end hole 4000 (provided that the valve 9000 (when present) is open). To further facilitate aspiration though the distal end hole 4000 (e.g., such that blood flows from the distal end hole 4000 to the proximal end hole 7000), it is envisioned that the proximal end hole 7000 may be attached to, connected to, or otherwise in communication with an aspiration regulator or controller. When the device 1200 and the sheath 60000 are in the second configuration (e.g., when the side hole(s) 2200 are open (exposed from the sheath 60000)), however, blood flows from the side hole(s) 2200 through the distal end hole 4000, thereby establishing a bypass around the blockage B (FIG. 3).

In certain embodiments, such as that shown in FIG. 21, it is envisioned that the sheath 60000 may include (support) one or more inflatable members 50000 (e.g., balloons) on an outer surface thereof such that, upon expansion, the inflatable member(s) 50000 facilitate anchoring of the sheath 60000 within the blood vessel V and/or flow control (FIG. 3). Although shown as including a single inflatable member 50000 that is located at (e.g., adjacent to) a distal end of the sheath 60000 in the illustrated embodiment, it should be appreciated that the number and/or the location of the inflatable member(s) 50000 may be varied without departing from the scope of the present disclosure.

Various combinations of all devices and methods described above may be utilized in the same procedure, sequentially, and/or simultaneously. It is also envisioned that each of the medical devices (e.g., catheters) described herein may be configured for delivery over, and used in conjunction with, a guidewire that is insertable therethrough.

Balloon Element on Bypass Catheter

In various embodiments of the disclosure, devices are described that are configured for deployment across a blockage in a blood vessel. The disclosed devices include a catheter with at least one distal end hole and at least one bypass window that is located proximally of the distal end hole.

In variations on the device, one or more inflatable members (e.g., temporary balloon elements) may be included. For example, the inflatable member(s) may be positioned between the distal end hole and the bypass window. It is envisioned that such devices may be deployed across the blockage B (FIG. 3) in the blood vessel V prior to expansion of the inflatable member(s). Alternatively, one or more balloon(s) may be located proximally of the side hole, and/or on an outer catheter (sheath) separate from the bypass catheter, through which the bypass catheter may be advanced.

Articulation and Deflection

To facilitate access to various locations within the patient's vasculature (e.g., the blood vessel V (FIG. 3) and/or anchoring (bracing) within the patient's vasculature, it is envisioned that the various devices described herein may be configured for articulation and controlled deflection. Although discussed herein below in the context of the macerating irrigation catheter 300 (FIG. 5), it should be appreciated that the following elements and features may be incorporated into, and adapted for use, with any of the devices (and alternate embodiments thereof) described herein. For example, it is envisioned that one or more of the macerating microwire 200 (FIG. 4), the aspiration catheter 400 (FIG. 6), the aspiration catheter 800 (FIGS. 7F-7I), the aspiration catheter 900 (FIG. 7C), the aspiration catheter 1000 (FIG. 8), the respective first and second members 1050, 1060 (FIGS. 8A, 8B), the outer (delivery) catheter 1100 (FIGS. 12A, 12B), the (bypass catheter) device 1200 (FIG. 17), the aspiration catheter 1500 (FIG. 15), etc., may be configured for articulation (reconfiguration) in the manner described with respect to the macerating irrigation catheter 300. For simplicity and/or clarity, certain elements, components, and/or features of the macerating irrigation catheter 300 may be omitted from the illustration provided in FIGS. 22-24 including, for example, the side hole(s) 330, the macerating member(s) 222, etc. All devices described herein may (optionally) include one or more steerable segments that are deflectable via one or more pull wires that extend within the wall of the device consistent with the discussion below. To vary tension on the pull wires, the device may include or may be connected to any suitable mechanism including, for example, a wheel, a ratchet, etc., thereby curving the device, as descried in further detail below.

Figure 24:
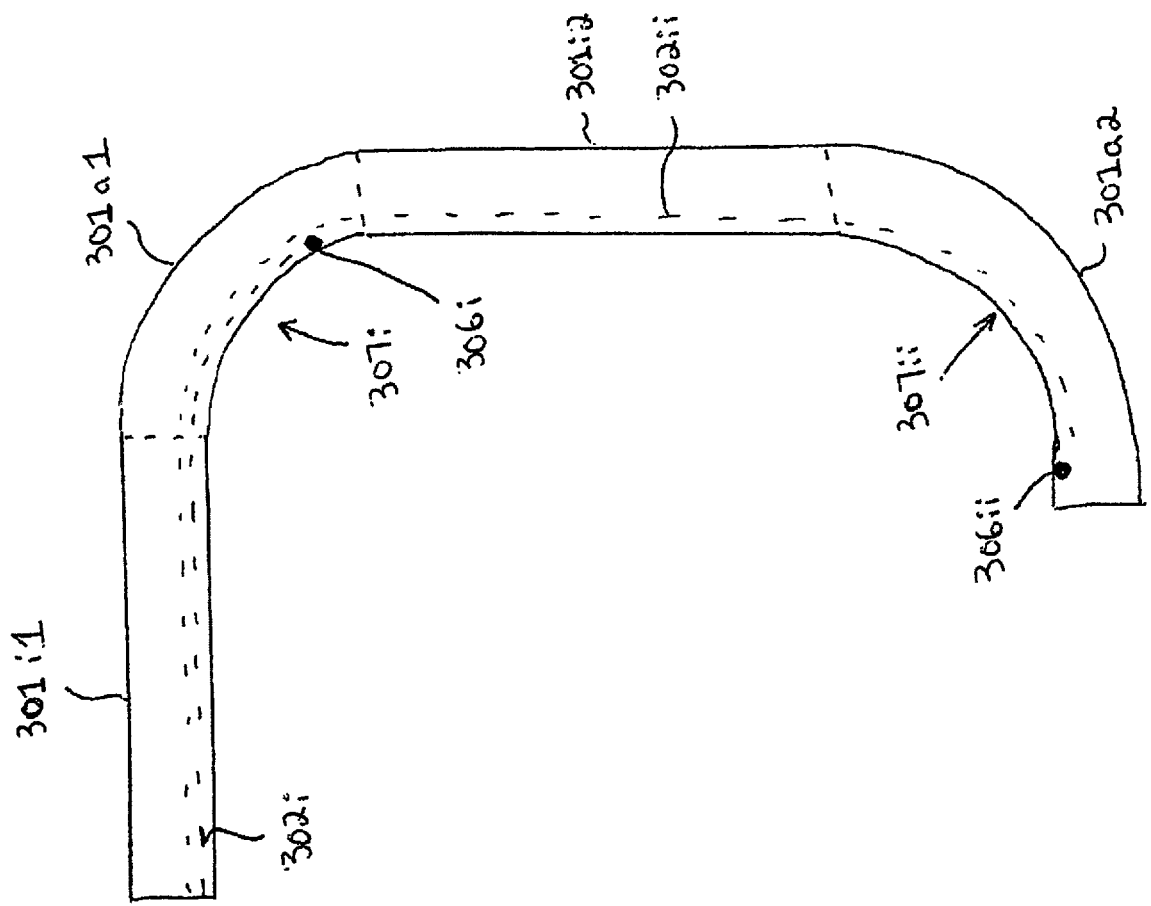
FIG. 24 is a schematic representation of the medical device of FIG. 22 shown in a second (subsequent, deflected) configuration.

With reference now to FIGS. 22-24, to facilitate articulation, the macerating irrigation catheter 300 includes a plurality of segments 301 and a plurality of pull wires 302. More specifically, the macerating irrigation catheter 300 includes a plurality of inactive (passive) segments 301*i* and a plurality of active (steerable, deflectable, articulable) segments 301*a* that are connected to the plurality of pull wires 302 and spaced along a longitudinal axis X of the macerating irrigation catheter 300. The inactive segments 301*i* and the active segments 301*a* are arranged in a staggered pattern such the macerating irrigation catheter 300 alternates between inactive segments 301*i* and active segments 301*a*.

Note the pull wires can in some embodiments be positioned in or built into the wall of the catheter, sheath, inner member and/or outer member of the various embodiments disclosed herein.

In the particular embodiment shown, each active segment 301*a* is connected to a corresponding (single) pull wire 302 that extends through (e.g., within) an outer wall 303 of the macerating irrigation catheter 300 such that the number of pull wires 302 corresponds to the number of active segments 301*a*. Upon the application of an axial (pulling) force to each of the pull wires 302, the corresponding active segment 301*a* is deflected (articulated) to thereby reconfigure (actively steer) the macerating irrigation catheter 300 between a first (initial, normal) configuration (FIG. 22), in which the macerating irrigation catheter 300 includes a (generally) linear configuration, and a second (subsequent, deflected) configuration (FIG. 23), in which the macerating irrigation catheter 300 includes a non-linear configuration.

The use of a single pull wire 302 in connection with each active segment 301*a* reduces the requisite number of pull wires 302, thus reducing complexity in both construction and operation of the macerating irrigation catheter 300. It is also envisioned that multiple, independently movable pull wires 302 may be included in other embodiments. In the particular embodiment illustrated, each pull wire 302 is received within a corresponding channel 304 (FIG. 24) that extends through the outer wall 303 of the macerating irrigation catheter 300 in (generally) parallel relation to the longitudinal axis X (e.g., such that the pull wires 302 are embedded within the macerating irrigation catheter 300).

To facilitate the application of axial force to the pull wires 302, in certain embodiments, the macerating irrigation catheter 300 may include (or may be connected to) a plurality of corresponding activating mechanisms 305 (e.g., such that the number of pull wires 302 corresponds to the number of activating mechanisms 305). In the particular embodiment illustrated, the macerating irrigation catheter 300 includes a (first) activating mechanism 305*i* that is connected to the pull wire 302*i* and a (second) activating mechanism 305*ii* that is connected to the pull wire 302*ii*. The activating mechanisms 305 may include any structure or mechanism suitable for the intended purpose of applying the axial force to the pull wires 302 required to deflect the macerating irrigation catheter 300 as necessary or desired, such as, for example, rotating wheels, pulley systems, or the like. In certain embodiments, it is envisioned that the active segments 301*a*, the pull wires 302, and the activating mechanisms 305 may be configured (and connected) such that each pull wire 302 may be individually acted upon to deflect (steer) the corresponding segment 301a in a single direction only. In other embodiments, it is envisioned that pull wires 302 may be provided on various circumferential surfaces of the macerating irrigation catheter 300 to facilitate steering in various directions.

In the particular embodiment illustrated, the macerating irrigation catheter 300 includes a first inactive segment 301i1; a first active segment 301a1 that is located distally of the segment 301i1; a second inactive segment 30112 that is located distally of the segment 301a1; and a second active segment 301a2 that is located distally of the segment 301i2. Additionally, the macerating irrigation catheter 300 includes respective first and second pull wires 302i, 30ii that are located within the channel 304 (FIG. 24). It is also envisioned, however, that the first and second pull wires 302i, 30ii may be located within separate channels 304 (e.g., such that the number of channels 304 corresponds to the number of pull wires 302).

The pull wires 302i, 30ii are connected to the segments 301a1, 301a2 at connection points 3061, 306ii (in addition to the activating mechanism 34i, 34ii), respectively, so as to facilitate reconfiguration of the macerating irrigation catheter 300 between the first configuration (FIG. 22) and the second configuration (FIG. 23). More specifically, upon reconfiguration of the macerating irrigation catheter 300, the active segments 301ai, 301aii define respective first and second bends 307i, 307ii, which may be either substantially similar (e.g., identical) or dissimilar depending, for example, upon the particular configuration of the segments 301a1, 301a2, the materials of construction used in the macerating irrigation catheter 300, the particular requirements of the macerating irrigation catheter 300 dictated by the endovascular procedure, etc. Although the bends 307i, 307ii are each illustrated as being (approximately) equal to 90 degrees in FIG. 23, depending upon the particular configuration of the segments 301a1, 301a2, the requirements of the endovascular procedure, the particular anatomy of the patient's vasculature, etc., it is envisioned that the bends 307i, 307ii may lie substantially within the range of approximately 0 degrees to approximately 270 degrees. For example, in one particular embodiment, it is envisioned that the segment 301a1 may be configured such that the bend 307i lies substantially within the range of approximately 0 degrees to approximately 180 degrees (e.g., approximately 90 degrees to approximately 180 degrees) and that the segment 301a2 may be configured such that the bend 307ii lies substantially within the range of approximately 0 degrees to approximately 270 degrees (e.g., approximately 90 degrees to approximately 270 degrees).

In the particular embodiment illustrated, the connection points 306i, 306ii are shown as being in (general) angular alignment (e.g., along a circumference of the macerating irrigation catheter 300), which facilitates deflection of the segments 301a1, 301a2 in similar (e.g., identical) directions, as seen in FIG. 23. It is also envisioned, however, that the connection points 3061, 306ii may be angularly offset so as to facilitate deflection of the segments 301a1, 301a2 in dissimilar directions. For example, the connection points 3061, 306ii may be oriented in (generally) diametric opposition such that the bends 307i, 307ii respectively defined by the segments 301a1, 301a2 curve in (generally) opposite directions.

A built in camera can be provided in any of the catheters disclosed herein for visualization during insertion and during the surgical procedure to visualize directly intravascularly.

The filters disclosed herein can be closed in some embodiments by a lasso or snare such as disclosed in US Publication 2019/0262120, the entire contents of which are incorporated herein by reference. The snare or lasso can extend through a lumen of the catheter or can be built into a wall of the catheter to collapse the filter.

As an alternative to the macerators disclosed herein, a clot retrieval device can be inserted through the sheaths and catheters disclosed herein in the same manner as the disclosed macerators.

Note the catheters and/or sheaths disclosed herein can optionally have non-round outer cross-sectional shapes (outer diameters and/or inner diameters), e.g., ellipse, oval, rectangular or other shapes. In some embodiments, the inner member and outer member or catheters or sheaths can have different cross-sections e.g., different shapes such as one being circular and the other non-circular to inhibit rotation between the two members.

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure and it should be understood by those skilled in the art that various changes may be made (and equivalents may be substituted) without departing from the true spirit and scope of the present disclosure. In addition, many modifications may be made to adopt a particular situation, material, composition of matter, process, process step or steps, to the objective spirit and scope of the present disclosure. All such modifications are intended to be within the scope of the claims appended hereto. For example, persons skilled in the art will understand that the elements and features shown or described in connection with one embodiment may be combined with those of another embodiment without departing from the scope of the present disclosure and will appreciate further features and advantages of the presently disclosed subject matter based on the description provided.

Where a range of values is provided, it is understood that each intervening value, to the tenth of the unit of the lower limit unless the context clearly dictates otherwise, between the upper and lower limit of that range and any other stated or intervening value in that stated range is encompassed by the present disclosure. The upper and lower limits of these smaller ranges which may independently be included in the smaller ranges is also encompassed by the present disclosure, subject to any specifically excluded limit in the stated range. Where the stated range includes one or both of the limits, ranges excluding either both of those included limits are also included in the present disclosure.

Unless defined otherwise, all technical and scientific terms used herein have the same meaning as commonly understood by one of ordinary skill in the art. Although any methods and materials similar or equivalent to those described herein can also be used in the practice or testing of the devices and methods described herein, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

Any publications discussed herein are provided solely for their disclosure prior to the filing date of the present application and each is incorporated by reference in its entirety. Nothing herein is to be construed as an admission that the present disclosure is not entitled to antedate such publication by virtue of prior disclosure. Further, the dates of publication provided may be different from the actual publication dates which may need to be independently confirmed.

Throughout the present disclosure, terms such as "approximately," "generally," "substantially," and the like should be understood to allow for variations in any numerical range or concept with which they are associated. For example, it is intended that the use of terms such as "approximately" and "generally" should be understood to encompass variations on the order of 25% (e.g., to allow for manufacturing tolerances and/or deviations in design).

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

Various combinations of all devices and methods described above may be utilized in the same procedure, sequentially and/or simultaneously.

What is claimed is:

1. A method of performing an endovascular procedure on a patient, the method comprising:
    advancing an outer member through the patient's aorta, across the patient's aortic arch, and beyond the patient's innominate artery;
    causing relative longitudinal movement between the outer member and an inner member located within the outer member to deploy and expand a filter element supported by the inner member to capture emboli;
    delivering a replacement valve into the patient's heart while filtering emboli through the filter element; wherein delivering the replacement valve includes delivering the replacement valve through a delivery member separate from the outer member; and wherein advancing the outer member includes advancing the outer member in a first direction and wherein delivering the replacement valve through the delivery member includes advancing the delivery member in a second direction generally opposite to the first direction.

2. The method of claim 1, wherein deploying and expanding the filter element includes locating the filter element between the patient's innominate artery and the patient's aortic valve to protect the patient's innominate artery, the patient's left common carotid artery, the patient's left subclavian artery, and the patient's aorta.

3. The method of claim 1, wherein delivering the replacement valve into a heart of the patient includes placing the replacement valve within an existing valve.

4. The method of claim 3, wherein delivering the replacement valve into a heart of the patient includes placing the replacement valve within a damaged anatomical valve naturally occurring within the patient.

5. The method of claim 1, further comprising retrieving an existing valve from the patient.

6. The method of claim 1, further comprising collapsing the filter element to facilitate removal of the filter element from the patient by withdrawing the inner member and the filter element into the outer member.

7. The method of claim 1, further comprising collapsing the filter element to facilitate removal of the filter element from the patient by advancing the outer member distally over the inner member and the filter element.

8. The method of claim 1, wherein expanding the filter element includes expanding a semi-permeable member of the filter element positioned about a distal end hole of the inner member into a funnel-shaped configuration such that an outer rim of the filter element contacts an inner wall of the patient's aorta.

9. The method of claim 1, further comprising performing a lithotripsy procedure prior to delivering the replacement valve.

10. The method of claim 1, wherein the delivery member has a non-circular outer transverse cross-sectional configuration.

11. The method of claim 1, wherein the delivery member has a non-circular inner transverse cross-sectional configuration.

12. The method of claim 1, wherein the filter element includes a first portion defining a first longitudinal length and a second portion defining a second longitudinal length greater than the first longitudinal length such that the filter element is asymmetrical in configuration.

13. The method of claim 1, wherein one or both of the outer member and inner member includes at least one steerable segment to facilitate reconfiguration thereof.

14. The method of claim 13, further comprising at least one control wire within a wall of the outer member or inner member movable to steer the segment, wherein the wire is movable to steer the segment in a single direction.

15. The method of claim 13, further comprising at least one control wire within a wall of the outer member or inner member movable to steer the segment, wherein the wire is movable to steer the segment in multiple directions.

16. The method of claim 15, wherein a wheel controls the wire.

* * * * *